(12) United States Patent
Zanetti

(10) Patent No.: US 8,372,640 B2
(45) Date of Patent: Feb. 12, 2013

(54) SOMATIC TRANSGENE IMMUNIZATION AND RELATED METHODS

(75) Inventor: Maurizio Zanetti, La Jolla, CA (US)

(73) Assignee: Nevagen LLC, La Jolla, CA (US)

( * ) Notice: Subject to any disclaimer, the term of this patent is extended or adjusted under 35 U.S.C. 154(b) by 391 days.

(21) Appl. No.: 11/640,778

(22) Filed: Dec. 18, 2006

(65) Prior Publication Data

US 2007/0117774 A1   May 24, 2007

Related U.S. Application Data

(63) Continuation-in-part of application No. 09/300,959, filed on Apr. 27, 1999, now Pat. No. 7,279,462.

(60) Provisional application No. 60/083,154, filed on Apr. 27, 1998.

(51) Int. Cl.
*C12N 5/10* (2006.01)
*C12N 5/0781* (2010.01)

(52) U.S. Cl. ............... 435/328; 435/326; 435/372.2

(58) Field of Classification Search ............ 435/328, 435/326, 372.2
See application file for complete search history.

(56) References Cited

U.S. PATENT DOCUMENTS

| | | | |
|---|---|---|---|
| 5,508,386 A * | 4/1996 | Zanetti et al. | 530/387.3 |
| 5,580,859 A | 12/1996 | Felgner et al. | 514/44 |
| 5,583,202 A | 12/1996 | Zanetti | 530/387.3 |
| 5,589,466 A | 12/1996 | Felgner et al. | 514/44 |
| 5,658,762 A * | 8/1997 | Zanetti et al. | 435/69.6 |
| 5,703,055 A | 12/1997 | Felgner et al. | 514/44 |
| 5,891,432 A * | 4/1999 | Hoo | 424/93.21 |
| 5,969,109 A | 10/1999 | Bona et al. | 530/387.3 |
| 6,977,074 B2 | 12/2005 | Kundig | 424/184.1 |
| 7,195,758 B2 * | 3/2007 | Schultze et al. | 424/93.71 |
| 7,279,462 B1 | 10/2007 | Zanetti | 514/44 |
| 2002/0090381 A1 * | 7/2002 | Bottomly et al. | 424/198.1 |
| 2008/0076175 A1 | 3/2008 | Zanetti | 435/375 |

FOREIGN PATENT DOCUMENTS

| | | |
|---|---|---|
| EP | 0 460 076 B1 | 11/1995 |
| WO | WO 00/64488 | 11/2000 |

OTHER PUBLICATIONS

Xiong et al. (1997) Nat. Biotech, vol. 15, 882-886.*
Banerji et al. (1983) Cell, vol. 33, 729-740.*
Munesinghe et al. (1991) Eur. J. Immunol., vol. 21, 3015-3020.*
Gerloni et al. (Feb. 1998) Eur. J. Immunol.*
Gerloni et al. (Jan./Feb. 1998) Vaccine, vol. 16(2/3), 293-297.*
Gerloni et al. (1997) Nature Medicine, vol. 15, 876-881.*
Gerloni et al. (May 1997) DNA and Cell Biology, vol. 16(5), 611-625.*
U.S. Appl. No. 09/300,959, Sep. 19, 2007, Issue Notification.
U.S. Appl. No. 09/300,959, Aug. 30, 2007, Miscellaneous Incoming Letter.
U.S. Appl. No. 09/300,959, Aug. 30, 2007, Drawings-only black and white line drawings.
U.S. Appl. No. 09/300,959, May 25, 2007, Notice of Allowance and Fees Due (PTOL-85).
U.S. Appl. No. 09/300,959, Feb. 2, 2007, Amendment—After Non-Final Rejection.
U.S. Appl. No. 09/300,959, Feb. 2, 2007, Specification.
U.S. Appl. No. 09/300,959, Feb. 2, 2007, Applicant Arguments/Remarks Made in an Amendment.
U.S. Appl. No. 09/300,959, Oct. 4, 2006, Non-Final Rejection.
U.S. Appl. No. 09/300,959, Sep. 7, 2006, Amendment Submitted/Entered with Filing of CPA/RCE.
U.S. Appl. No. 09/300,959, Sep. 7, 2006, Claims.
U.S. Appl. No. 09/300,959, Sep. 7, 2006, Applicant Arguments/Remarks Made in an Amendment.
U.S. Appl. No. 09/300,959, Sep. 7, 2005, Final Rejection.
U.S. Appl. No. 09/300,959, Jun. 22, 2005, Amendment—After Non-Final Rejection.
U.S. Appl. No. 09/300,959, Jun. 22, 2005, Claims.
U.S. Appl. No. 09/300,959, Jun. 22, 2005, Applicant Arguments/Remarks Made in an Amendment.
U.S. Appl. No. 09/300,959, Jun. 6, 2005, Miscellaneous Action with SSP.
U.S. Appl. No. 09/300,959, May 23, 2005, Informal or Non-Responsive Amendment.
U.S. Appl. No. 09/300,959, May 23, 2005, Claims.
U.S. Appl. No. 09/300,959, May 23, 2005, Applicant Arguments/Remarks Made in an Amendment.
U.S. Appl. No. 09/300,959, Nov. 23, 2004, Non-Final Rejection.
U.S. Appl. No. 09/300,959, Sep. 10, 2004, Amendment—After Non-Final Rejection.
U.S. Appl. No. 09/300,959, Sep. 10, 2004, Claims.
U.S. Appl. No. 09/300,959, Sep. 10, 2004, Applicant Arguments/Remarks Made in an Amendment.
U.S. Appl. No. 09/300,959, Mar. 10, 2004, Non-Final Rejection.
U.S. Appl. No. 09/300,959, Mar. 10, 2004, List of references.
U.S. Appl. No. 09/300,959, Oct. 27, 2003, Advisory Action (PTOL-303).
U.S. Appl. No. 09/300,959, Jul. 31, 2003, Transmittal to TC.
U.S. Appl. No. 09/300,959, Jul. 31, 2003, Amendment—After Non-Final Rejection.
U.S. Appl. No. 09/300,959, Jul. 31, 2003, Claims.
U.S. Appl. No. 09/300,959, Jul. 31, 2003, Applicant Arguments/Remarks Made in an Amendment.
U.S. Appl. No. 09/300,959, Apr. 2, 2003, Examiner Interview Summary Record (PTOL-413).
U.S. Appl. No. 09/300,959, Jan. 30, 2003, Final Rejection.
U.S. Appl. No. 09/300,959, Nov. 18, 2002, Amendment—After Non-Final Rejection.

(Continued)

Primary Examiner — Anne Marie S Wehbe
(74) Attorney, Agent, or Firm — Morgan Lewis & Bockius LLP; Richard F. Trecartin

(57) ABSTRACT

The invention provides a method for stimulating an immune response by administering to a lymphoid tissue a nucleic acid molecule comprising an expression element operationally linked to a nucleic acid sequence encoding one or more heterologous epitopes. The heterologous epitope can be inserted into a complementarity-determining region of an immunoglobulin molecule. The invention also provides a nucleic acid molecule comprising a hematopoietic expression element operationally linked to a nucleic acid sequence encoding a heterologous polypeptide. The invention additionally provides a method of treating a condition by administering a nucleic acid molecule comprising a hematopoietic cell expression element operationally linked to a nucleic acid sequence encoding a heterologous polypeptide, wherein the nucleic acid molecule is targeted to a hematopoietic cell.

6 Claims, 37 Drawing Sheets

OTHER PUBLICATIONS

U.S. Appl. No. 09/300,959, Nov. 18, 2002, Claims.
U.S. Appl. No. 09/300,959, Nov. 18, 2002, Applicant Arguments/Remarks Made in an Amendment.
U.S. Appl. No. 09/300,959, Nov. 18, 2002, Miscellaneous Incoming Letter.
U.S. Appl. No. 09/300,959, May 9, 2002, Non-Final Rejection.
U.S. Appl. No. 09/300,959, May 9, 2002, List of references.
U.S. Appl. No. 09/300,959, Feb. 12, 2002, Amendment—After Non-Final Rejection.
U.S. Appl. No. 09/300,959, Feb. 12, 2002, Claims.
U.S. Appl. No. 09/300,959, Feb. 12, 2002, Applicant Arguments/Remarks Made in an Amendment.
U.S. Appl. No. 09/300,959, Jul. 20, 2001, Non-Final Rejection.
U.S. Appl. No. 09/300,959, Jul. 20, 2001, List of references.
U.S. Appl. No. 09/300,959, Apr. 30, 2001, Amendment—After Non-Final Rejection.
U.S. Appl. No. 09/300,959, Apr. 30, 2001, Claims.
U.S. Appl. No. 09/300,959, Apr. 30, 2001, Applicant Arguments/Remarks Made in an Amendment.
U.S. Appl. No. 09/300,959, Oct. 25, 2000, Non-Final Rejection.
U.S. Appl. No. 09/300,959, Oct. 25, 2000, List of references.
U.S. Appl. No. 09/300,959, Jul. 26, 2000, Miscellaneous Incoming Letter.
U.S. Appl. No. 09/300,959, Jul. 26, 2000, Amendment—After Non-Final Rejection.
U.S. Appl. No. 09/300,959, Jul. 26, 2000, Specification.
U.S. Appl. No. 09/300,959, Jul. 26, 2000, Applicant Arguments/Remarks Made in an Amendment.
U.S. Appl. No. 09/300,959, Jul. 26, 2000, CRF Sequence Listing Filed.
U.S. Appl. No. 09/300,959, Jul. 26, 2000, Sequence Listing.
U.S. Appl. No. 09/300,959, Jul. 10, 2000, Change of Address.
U.S. Appl. No. 09/300,959, Jun. 21, 2000, Requirement for Restriction/Election.
U.S. Appl. No. 09/300,959, Apr. 4, 2000, Miscellaneous Incoming Letter.
U.S. Appl. No. 09/300,959, Apr. 4, 2000, Response to Election / Restriction Filed.
U.S. Appl. No. 09/300,959, Apr. 4, 2000, Applicant Arguments/Remarks Made in an Amendment.
U.S. Appl. No. 09/300,959, Feb. 29, 2000, Requirement for Restriction/Election.
2369616, Mar. 20, 2008 Response to Examination.
2369616, Sep. 20, 2007, Office Action.
2369616, Apr. 23, 2007, Response to Examination.
2369616, Oct. 25, 2001, Preliminary Amendment.
2369616, Oct. 23, 2006, Office Action.
00930184.7, Mar. 28, 2008, Annex to the communication.
00930184.7, Mar. 28, 2008, Examination report.
00930184.7, Nov. 19, 2007, Reply to examination report.
00930184.7, Nov. 19, 2007, Claims.
00930184.7, May 9, 2007, Examination report.
00930184.7, May 9, 2007, Annex to the communication.
00930184.7, Oct. 31, 2006, Decision to allow further processing.
00930184.7, Oct. 16, 2006, Request for further processing.
00930184.7, Oct. 16, 2006, Claims.
00930184.7, Dec. 20, 2005, Annex to the communication.
00930184.7, Dec. 20, 2005, Examination report.
00930184.7, Dec. 20, 2005, Annex to a communication.
00930184.7, Dec. 9, 2004, Reply to examination report.
00930184.7, Dec. 9, 2004, Annex.
00930184.7, Dec. 9, 2004, Claims.
00930184.7, Mar. 22, 2004, Examination report.
00930184.7, Mar. 22, 2004, Annex to the communication.
00930184.7, Jul. 11, 2002, The international search report.
00930184.7, Jul. 11, 2002, Corrected international publication (Pamphlet).
00930184.7, Feb. 21, 2002, Amendments received before examination.
00930184.7, Feb. 21, 2002, Claims.
00930184.7, Oct. 23, 2001, The international preliminary examination report.
00930184.7, May 10, 2001, International publication of the international search report.
00930184.7, May 10, 2001, The international search report.
2000-613478, Sep. 13, 2007, Translation of Amended Claims in Response to Examination.
2000-613478, Mar. 14, 2007, Examination (English translation).
2000-613478, Oct. 25, 2001, Translation of Amended Claims.
PCT/US2000/011372, May 28, 2001, International Preliminary Examination Report (IPER).
PCT/US2000/011372, May 10, 2001, International Search Report.
PCT/US2000/011372, Jan. 31, 2001, Written Opinion.
U.S. Appl. No. 10/030,003, May 2, 2006, Final Rejection.
U.S. Appl. No. 10/030,003, Feb. 13, 2006, Amendment—After Non-Final Rejection.
U.S. Appl. No. 10/030,003, Feb. 13, 2006, Specification.
U.S. Appl. No. 10/030,003, Feb. 13, 2006, Claims.
U.S. Appl. No. 10/030,003, Feb. 13, 2006, Applicant Arguments/Remarks Made in an Amendment.
U.S. Appl. No. 10/030,003, Aug. 11, 2005, Non-Final Rejection.
U.S. Appl. No. 10/030,003, Aug. 11, 2005, List of references.
U.S. Appl. No. 10/030,003, Jun. 9, 2005, Amendment—After Non-Final Rejection.
U.S. Appl. No. 10/030,003, Jun. 9, 2005, Claims.
U.S. Appl. No. 10/030,003, Jun. 9, 2005, Applicant Arguments/Remarks Made in an Amendment.
U.S. Appl. No. 10/030,003, Feb. 16, 2005, Response to Election / Restriction Filed.
U.S. Appl. No. 10/030,003, Feb. 16, 2005, Claims.
U.S. Appl. No. 10/030,003, Feb. 16, 2005, Applicant Arguments/Remarks Made in an Amendment.
U.S. Appl. No. 10/030,003, Dec. 16, 2004, Requirement for Restriction/Election.
U.S. Appl. No. 10/030,003, Aug. 5, 2002, Preliminary Amendment.
U.S. Appl. No. 10/030,003, Mar. 6, 2002, Preliminary Amendment.
U.S. Appl. No. 10/030,003, Mar. 6, 2002, Applicant Arguments/Remarks Made in an Amendment.
U.S. Appl. No. 11/713,477, Mar. 1, 2007, Preliminary Amendment.
U.S. Appl. No. 11/713,477, Mar. 1, 2007, Specification.
U.S. Appl. No. 11/713,477, Mar. 1, 2007, Claims.
U.S. Appl. No. 11/713,477, Mar. 1, 2007, Applicant Arguments/Remarks Made in an Amendment.
U.S. Appl. No. 11/869,463, Oct. 9, 2007, Preliminary Amendment.
U.S. Appl. No. 11/869,463, Oct. 9, 2007, Specification.
U.S. Appl. No. 11/869,463, Oct. 9, 2007, Claims.
U.S. Appl. No. 11/869,463, Oct. 9, 2007, Applicant Arguments/Remarks Made in an Amendment.
Anderson, et al, "Immune response in mice following immunization with DNA encoding fragment C of tetanus toxin," Infect. *Immunity* 64:3168-3173 (1996).
Banerji, et al., "A Lymphocyte-specific cellular enhancer is located downstream of the joining region in immunoglobulin heavy chain genes," *Cell* 33:729-740 (1983).
Barry, et al., "Protection against mycoplasma infection using expression-library immunization," *Nature* 377:632-635 (1995).
Bennett, et al., "B cells directly tolerize CD8+T cell" *J. Exp. Med.* 188(11):1977-1983 (1998).
Billetta, et al., "Major histocompatibility complex class I-restricted presentation of influenza virus nucleoprotein peptide by B lymphoma cells harboring an antibody gene antigenized with the virus peptide," *Eur. J. Immunol.* 25:776-783 (1995).
Billetta, et al., "Antigenicity and immunogenicity of antigenized antibodies. Studies on B and T cells," *Intern. Rev. Immunol.* 10:251-263 (1993).
Billetta, et al., "Ligand expression using antigenization of antibody: principal and methods," *Immuno Methods* 1:41-51 (1992).
Boyle, et al., "Enhanced responses to a DNA vaccine encoding a fusion antigen that is directed to sites of immune induction," *Nature* 392:408-411 (1998).
Castiglioni, et al., "CD4 T cell priming in dendritic cell-deficient mice," *International Immunology* 15(1):127-136 (2003).

Castiglioni, et al., "CD8 T cell priming by B lymphocytes is CD4 help dependent," *Eur. J. Immunol.* 35:1360-1370 (2005).
Castiglioni, et al., "Genetically programmed B lymphocytes are highly efficient in inducing anti-virus protective immunity mediated by central memory CD8 T cells," *Vaccine* 23:699-708 (2004).
Chattergoon, et al, "Specific immune induction following DNA-based immunization through in vivo transfection and activation of macrophages/antigen-presenting cells," *J. Immunol.* 160:5707-5718 (1998).
Chen, et al., "Idiotype-cytokine fusion proteins as cancer vaccines. Relative efficacy of IL-2, IL-4, and granulocyte-macrophage colony-stimulating factor," *J. Immunol.* 153:4775-4787 (1994).
Cohen, "Naked DNA points way to vaccines," *Science* 259-1691-1692 (1993).
Condon, et al., "DNA-based immunization by in vivo transfection of dendritic cells," *Nat. Med.* 2:1122-1128 (1996).
Conry, et al., "Immune response to a carcinoembryonic antigen polynucleotide vaccine," *Cancer Res.* 54:1164-1168 (1994).
Cortez-Gonzalez, et al., "TLR9-Independent activation of B lymphocytes by bacterial DNA," *DNA and Cell Biology* 25(5):253-261 (2006).
Cox, et al., "Bovine herpesvirus 1: immune responses in mice and cattle injected with plasmid DNA," *J. Virol.* 67:5664-5667 (1993).
Crystal, "Transfer of genes to humans: early lessons and obstacles to success," *Science* 270:404-410 (1995).
Davis, et, al., "Direct gene transfer into skeletal muscle in vivo: factors affecting efficiency of transfer and stability of expression," *Human Gene. Ther.* 4:151-159 (1993).
Davis, et al., "Direct gene transfer in skeletal muscle: plasmid DNA-based immunization against the hepatitis B virus surface antigen," *Vaccine* 12:1503-1509 (1994).
Davis et al., "Use of plasmid DNA for direct gene transfer and immunization," *Ann. NY Acad. Sci.* 772:21-29 (1995).
Davis et al., "DNA-mediated immunization to hepatitis B surface antigen: longevity of primary response and effect of boost," *Vaccine* 14:910-915 (1996).
Deonarain, "Ligand-targeted receptor-mediated vectors for gene therapy," *Exp. Opin. Ther. Patents* 8(1):53-69 (1998).
Disis, et al., "Granulocyte-macrophage colony-stimulation factor: an effective adjuvant for protein and peptide-based vaccines," *Blood* 88:202-210 (1996).
Doe, et al., "Induction of cytotoxic T lymphocytes by intramuscular immunization with plasmid DNA is facilitated by bone marrow-derived cells," *Proc. Nat'. Acad. Sci. USA* 93:8578-8583 (1996).
Donnelly, et al., "DNA vaccines," *Annu. Rev. Immunol.* 15:617-648 (1997).
Doolan, et al., "Circumventing genetic restriction of protection against malaria with multigene DNA immunization: CD8+ T-cell-, interferon y-, and nitric oxide-dependent immunity," *J. Exp. Med.*, 183:1739-1746 (1996).
Eck, et al, Goodman & Gilman's pharmacological basis of therapeutics, CH 8 McGraw-Hill pp. 77-101 (1999).
Eisenbraun, et al., "Examination of parameters affecting the elicitation of humoral immune responses by particle bombardment-mediated genetic immunization," *DNA Cell Biol.* 12:791-797 (1993).
Filaci, et al., "Spontaneous transgenesis of human B lymphocytes," *Gene Therapy* 11:42-51 (2004).
Fuchs, et al., "B cells turn off virgin but not memory T cells," *Science* 258:1156-1159 (1992).
Fynan, "DNA vaccines: protective immunizations by parental, mucosal and gene-gun inoculations," *Proc. Natl. Acad. Sci. USA* 90:11478-11482 (1993).
Gerloni, et al., "The cooperation between two CD4 T cells induces tumor protective immunity in MUC.1 transgenic mice," *The Journal of Immunology* 175:6551-6559 (2005).
Gerloni, et al., "T cell immunity using transgenic B lymphocytes," *Natl. Acad. Sci. USA* 101(11)3892-3897 (2004).
Gerloni, et al., "Functional cooperation between T helper cell determinants," *PNAS* 97(24):13269-13274 (2000).
Gerloni, et al., "Activation of CD4 T cells by somatic transgenesis induces generalized immunity of uncommitted T cells and immunologic memory" *J. Immunol* 162(7):3782-3789 (1999).

Gerloni, et al., "DNA immunization in re/B-deficient mice discloses a role for dendritic cells in IgM→IgLI switch in vivo," *Eur. J. Immunol.* 28:516-524 (1998).
Gerloni, et al., "Durable immunity and immunologic memory to a parasite antigen induced by somatic transgene immunization." *Vaccine* 16(2/3):293-297 (1998).
Gerloni, et al., "Immunological memory after somatic transgene immunization is positively affected by priming with GM-CSF and does not require bone marrow-derived dendritic cells," *Eur. J. Immunol.* 28:1832-1838 (1998).
Gerloni, et al., "Immunity to *Plasmodium falciparum* malaria sporozoites by somatic transgene immunization," *Nat. Biotech.* 15:876-881 (1997).
Gerloni, et al., Somatic transgene immunization with DNA encoding and immunoglobulin heavy chain, *DNA and Cell Biol.* 16(5):611-625 (1997).
Gilbert, et al., "Tolerogenicity of resting and activated B cells," *J. Exp. Med.* 179:249-258.
Gilkeson, et al., "Modulation of renal disease in autoimmune NZB/NZW mice by immunization with bacterial DNA," *J. Exp. Med.* 183:1389-1397 (1996).
Gregoriadis, "Genetic vaccines: strategis for optimization," *Pharm. Res.* 15:661-670 (1998).
Hsu, et al., "Immunoprophylaxis of allergen-induced immunoglobulin E synthesis and airway hyperresponsiveness vivo by genetic immunization," *Nat. Med.* 2:540-544 (1996).
Hurpin, et al., "The mode of presentation and route of administration are critical for the induction of immune responses to p53 and antitumor immunity," *Vaccine* 16(2/3):208-215 (1998).
Huygen, et al., "Immunogenicity and protective efficacy of a tuberculosis DNA vaccine," *Nat. Med.* 2:893-898 (1996).
Iwasaki, et al., "The dominant role of bone marrow-derived cells in CTL induction following plasmid DNA immunization at different sites," *J. Immunol.* 159:11-14 (1997).
Janeway, et al., "Effects of antigen dose," *Immunobiology* 5, Garland Publishing, New York, p. 616 (2001).
Jones, et al., "Potential role of granulocyte-macrophage colony-stimulating factor as vaccine adjuvant," *Eur. J. Clin. Microbiol. Infect. Dis.*, 13 Suppl. 2:S47-S53 (1994).
Langlade-Demoyen, et al., "Role of T cell help and endoplasmic reticulum targeting in protective CTL response against influenza virus," *Eur. J. Immunol.* 33(3):720-728 (2003).
Maloy, et al., "Intralymphatic immunization enhances DNA vaccination," *PNAS* 98(6):3299-3203 (2001).
Manickan, et al., "Genetic immunization against herpes simplex virus. Protection is mediated by CD4↓ T Lymphocytes1," *J. Immunol.* 155:259-265 (1995).
Maxwell, et al., "Expression of the diphtheria toxin A-chain coding sequence under the control of promoters and enhancers from immunoglobulin genes as a means of directing toxicity to B-lymphoid cells," *Cancer Research* 51:4299-4304 (1991).
McCluskie, et al., "Route and method of delivery of DNA vaccine influence immune responses in mice and non-human primates," *Molecular Medicine* 9:267-300 (1999).
Miller, et al., "Targeted vectors for gene therapy," *FASEB J.* 9:190-199 (1995).
Nakano, et al., "Genetic defect in T lymphocyte-specific homing into peripheral lymph nodes," *Euro. J. Immunol.*,27(1):215-221 (1997).
Pertmer, et al., "Influenza virus nucleoprotein-specific immunoglobulin G subclass and cytokine responses elicited by DNA vaccination are dependent on the route of vector DNA delivery," *J. Virol.* 70:6119-6125 (1996).
Raz, et al., "Preferential induction of a Th1 immune response and inhibition of specific IgE antibody formation by plasmid DNA immunization," *Proc. Natl. Acad. Sci. USA* 93:5141-5145 (1996).
Raz, et al., "Intradermal gene immunization: the possible role of DNA uptake in the induction of cellular immunity to viruses," *Proc. Nat'l Acad. Sci. USA* 91:9519-9523 (1994).
Rizzi, et al., "In utero DNA immunization immunity over tolerance in fetal life," *Vaccine* 23(33):4273-4282 (2005).
Robinson, et al., "Protection against a lethal infueuza virus challenge by immunization with a haemagglutinin-expressing plasmid DNA," *Vaccine* 11:957-960 (1993).

Roman, et al., "Immunostimulatory DNA sequences function as T helper-1-promoting adjuvants," *Nat. Med.*, 3:849-854 (1997).

Sedegah, et al., "Protection against malaria by immunization with plasmid DNA encoding circumsporozoite protein," *Proc. Natl. Acad. Sci. USA* 91:9866-9870 (1994).

Smyth, et al., "An essential role for tumor necrosis factor in natural killer cell-mediated tumor rejection in the peritoneum," *J. Exp. Med.* 188(9)L1611-1619 (1998).

Syrengelas, et al., "DNA immunization induces protective immunity against B-cell lymphoma," *Nature Med.* 2:1038-1041 (1996).

Tang, et al., "Genetic immunization is a simple method for eliciting an immune response," *Nature* 356:152-154 (1992).

Tao, et al., "Idiotype/granulocyte-macrophage colony-stimulating factor fusion protein as a vaccine for B-cell lymphoma," *Nature* 362:755-758 (1993).

Tascon, et al., "Vaccination against tuberculosis by DNA injection," *Nat. Med.* 2:888-892 (1996).

Taubes, "Salvation in a snippet of DNA?" *Science* 278:1711-1714 (1997).

Torres, et al., "Differential dependence on target site tissue for gene gun and intramuscular Can immunizations," *J. Immunol.* 158:4529-4532 (1997).

Townsend, et al., "Abortive proliferation of rare T cells induced by direct or indirect antigen presentation by rare B cells in vivo," *J. Exp. Med.* 187(10)1611-1621 (1998).

Ulmer, et al., "Heterologous protection against influenza by injection of DNA encoding a viral protein," *Science* 259:1745-1749 (1993).

Ulmer, et al., "DNA vaccines," *Curr. Opin. Immunol.* 8:531-536 (1996).

Verma, et al., "Gene therapy—promises, problems and prospects," *Nature* 389:329-242 (1997).

Waisman, et al., "Suppressive vaccination with DNA encoding a variable region gene to the T-cell receptor prevents autoimmune encephalomyelitis and activates Th2 immunity," *Nat. Med.* 2:899-905 (1996).

Wang, et al., "Gene inoculation generates immune responses against human immunodeficiency virus type 1," *Proc. Natl. Acad. Sci. USA* 90:4156-4160 (1993).

Wang, et al., "DNA inoculation induces neutralizing immune responses in mice and nonhuman primates," *DNA Cell Biol.* 12:799-805 (1993).

Whalen, et al., "DNA-mediated immunization to the hepatitis B surface antigen. Activation and entrainment of the immune responses A, D," *Ann. NY Acad. Sci.* 772:64-76 (1995).

Xiang, et al., "Manipulation of the immune response to a plasmid-encoded viral antigen by coinoculation with plasmids expressing cytokines," *Immunity* 2:129-135 (1995).

Xiang, et al., "Vaccination with a plasmid vector carrying the rabies virus glycoprotein gene induces protective immunity against rabies virus," *Virology* 199:132-140 (1994).

Xiong et al., "Engineering vaccines with heterologous B and T cell epitopes using immunoglobulin genes," *Nat. Biotech.* 15(9):882-886 (1997).

Xiong et al., "In vivo role of B lymphocytes in somatic transgene immunization," *Proc. Natl. Acad. Sci. USA*, 94:6352-6357 (1997).

Xu, et al., "Protection against leishmaniasis by injection of DNA encoding a major surface glycoprotein, gp63, of L. *major*," *Immunology* 84:173-176 (1995).

Yankauckas, et al., "Long-term anti-nucleoprotein cellular and humoral immunity is induced by intramuscular injection of plasmid DNA containing NP gene," *DNA Cell Biol.* 12:771-776 (1993).

Zanetti, "Immunization with immunoglobulin genes," *The Antibodies* 4:Chapter 5, 73-79 (2001).

\* cited by examiner

SEQUENCE LISTING

<160> NUMBER OF SEQ ID NOS: 42

<210> SEQ ID NO 1
<211> LENGTH: 27
<212> TYPE: DNA
<213> ORGANISM: Mus musculus

<400> SEQUENCE: 1
aaggcctact ctcatggtat ggactac                                        27

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: mutant
      heavy chain complementarity determining region 3(CDR3)

<400> SEQUENCE: 2
aaggtaccct actctcatgg tatggactac                                     30

<210> SEQ ID NO 3
<211> LENGTH: 48
<212> TYPE: DNA
<213> ORGANISM: Artificial Sequence
<220> FEATURE:
<223> OTHER INFORMATION: Description of Artificial Sequence: mutant
      heavy chain complementarity determining region 3(CDR3)

<400> SEQUENCE: 3
gtacccaatg caaacccaaa tgcaaaccca aatgcaaacc cagtaccc                 48

<210> SEQ ID NO 4
<211> LENGTH: 4
<212> TYPE: PRT
<213> ORGANISM: Plasmodium falciparum

<400> SEQUENCE: 4

Asn Ala Asn Pro
  1

<210> SEQ ID NO 5
<211> LENGTH: 422
<212> TYPE: DNA
<213> ORGANISM: Artificial Sequence
<220> FEATURE:
<223> OTHER INFORMATION: Description of Artificial Sequence: genomic VDJ
      region

<400> SEQUENCE: 5
gacgtgaagc tggtggagtc tgggggaggc ttagtgaagc ttggagggtc cctgaaactc     60
tcctgtgcag cctctggatt cactttcagt aggtattaca tgtcttgggt tcgccagact    120
ccagagaaga ggctggagtt ggtcgcagcc attaatagta atggtggtag cacctactat    180
ccagacactg tgaagggccg attcaccatc tccagagaca tgccaaaaa caccctgtac     240 ctgcaaatga gcagtctgaa gtctgaggac acagccttgt attactgtgc aagaaaggta    300
ccctactctc atggtatgga ctactggggt caaggaacct cagtcaccgt ctcctcaggt    360
aagaatggcc tctccaggtc tttatttttta acctttgtta tggagttttc tgagcattgc   420
ag                                                                  422

<210> SEQ ID NO 6

<211> LENGTH: 422
<212> TYPE: DNA
<213> ORGANISM: Artificial Sequence
<220> FEATURE:
<223> OTHER INFORMATION: Description of Artificial Sequence: genomic VDJ
       region

<400> SEQUENCE: 6

| gacgtgaagc | tggtggagtc | tgggggaggc | ttagtgaagc | ttggagggtc | cctgaaactc | 60 |
| tcctgtgcag | cctctggatt | cactttcagt | aggtattaca | tgtcttgggt | tcgccagact | 120 |
| ccagagaaga | ggctggagtt | ggtcgcagcc | attaatagta | atggtggtag | cacctactat | 180 |
| ccagacactg | tgaagggccg | attcaccatc | tccagagaca | atgccaaaaa | caccctgtac | 240 |
| ctgcaaatga | gcagtctgaa | gtctgaggac | acagctttgt | attactgtgc | aagaaaggta | 300 |
| ccctactctc | atggtatgga | ctactggggt | caaggaacct | cagtcaccgt | ctcctcaggt | 360 |
| aagaatggcc | tctccaggtc | tttatttta | acctttgtta | tggagttttc | tgagcattgc | 420 |
| ag | | | | | | 422 |

<210> SEQ ID NO 7
<211> LENGTH: 419
<212> TYPE: DNA
<213> ORGANISM: Artificial Sequence
<220> FEATURE:
<223> OTHER INFORMATION: Description of Artificial Sequence: genomic VDJ
       region

<400> SEQUENCE: 7

| gacgtgaagc | tggtggagtc | tgggggaggc | ttagtgaagc | ttggagggtc | cctgaaactc | 60 |
| tcctgtgcag | cctctggatt | cactttcagt | aggtattaca | tgtcttgggt | tcgccagact | 120 |
| ccagagaaga | ggctggagtt | ggtcgcagcc | attaatagta | atggtggtag | cacctactat | 180 |
| ccagacactg | tgaagggccg | attcaccatc | tccagagaca | atgccaaaaa | caccctgtac | 240 |
| ctgcaaatga | gcagtctgaa | gtctgaggac | acagccttgt | attactgtgc | aagaaaggcc | 300 |
| tactctcatg | gtatggacta | ctggggtcaa | ggaacctcag | tcaccgtctc | ctcaggtaag | 360 |
| aatggcctct | ccaggtcttt | attttaacc | tttgttatgg | agttttctga | gcattgcag | 419 |

<210> SEQ ID NO 8
<211> LENGTH: 419
<212> TYPE: DNA
<213> ORGANISM: Artificial Sequence
<220> FEATURE:
<223> OTHER INFORMATION: Description of Artificial Sequence: genomic VDJ
       region

<400> SEQUENCE: 8

| gacgtgaagc | tggtggagtc | tgggggaggc | ttagtgaagc | ttggagggtc | cctgaaactc | 60 |
| tcctgtgcag | cctctggatt | cactttcagt | aggtattaca | tgtcttgggt | tcgccagact | 120 |
| ccagagaaga | ggctggagtt | ggtcgtagcc | attaatagta | atggtggtag | cacctactat | 180 |
| ccagacactg | tgaagggccg | attcaccatc | tccagagaca | atgccaaaaa | caccctgtac | 240 |
| ctgcaaatga | gcagtctgaa | gtctgaggac | acagccttgt | attactgtgc | aagaaaggcc | 300 |
| tactctcatg | gtatggacta | ctggggtcaa | ggaacctcag | tcaccgtctc | ctcaggtaag | 360 |
| aatggcctct | ccaggtcttt | attttaacc | tttgttatgg | agttttctga | gcattgcag | 419 |

<210> SEQ ID NO 9
<211> LENGTH: 12
<212> TYPE: PRT
<213> ORGANISM: Plasmodium falciparum

```
<400> SEQUENCE: 9

Asn Ala Asn Pro Asn Val Asp Pro Asn Ala Asn Pro
 1               5                  10

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence:
      complementarity determining region 2 (CDR2)

<400> SEQUENCE: 10
aatgcaaacc caaatgtaga tcccaatgcc aaccca                              36

<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence:
      complementarity determining region 3(CDR3)

<400> SEQUENCE: 11
aatgcaaacc caaatgcaaa cccaaatgca aaccca                              36

<210> SEQ ID NO 12
<211> LENGTH: 62
<212> TYPE: DNA
<213> ORGANISM: Artificial Sequence
<220> FEATURE:
<223> OTHER INFORMATION: Description of Artificial Sequence:
      complementarity determining region 3 (CDR3)

<400> SEQUENCE: 12
aaggtacccg cttccaatga aaatatggag actatggaat caagtacact tgtaccctac   60
tc                                                                  62

<210> SEQ ID NO 13
<211> LENGTH: 14
<212> TYPE: PRT
<213> ORGANISM: Influenza virus

<400> SEQUENCE: 13

Ala Ser Asn Glu Asn Met Glu Thr Met Glu Ser Ser Thr Leu
 1               5                  10

<210> SEQ ID NO 14
<211> LENGTH: 48
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 14
gtacccgctt ccaatgaaaa tatggagact atggaatcaa gtacactt                48

<210> SEQ ID NO 15
<211> LENGTH: 11
<212> TYPE: PRT
<213> ORGANISM: MUC-1 tumor antigen

<400> SEQUENCE: 15

Val Thr Ser Ala Pro Asp Thr Arg Pro Ala Pro
```

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 16

Val Thr Ser Ala Pro Asp Thr Arg Pro Ala Pro
 1               5                   10

<210> SEQ ID NO 17
<211> LENGTH: 12
<212> TYPE: PRT
<213> ORGANISM: MUC-1 tumor antigen

<400> SEQUENCE: 17

Pro Asp Thr Arg Pro Ala Pro Gly Ser Thr Ala Pro
 1               5                   10

<210> SEQ ID NO 18
<211> LENGTH: 24
<212> TYPE: DNA
<213> ORGANISM: Mus musculus

<400> SEQUENCE: 18
ttcgatgtcc ataccatgag agta                                    24

<210> SEQ ID NO 19
<211> LENGTH: 24
<212> TYPE: DNA
<213> ORGANISM: Mus musculus

<400> SEQUENCE: 19
ttcagcacct actatccaga cact                                    24

<210> SEQ ID NO 20
<211> LENGTH: 24
<212> TYPE: DNA
<213> ORGANISM: Homo sapiens

<400> SEQUENCE: 20
ttcctcttct gcgtgtagtg gttg                                    24

<210> SEQ ID NO 21
<211> LENGTH: 24
<212> TYPE: DNA
<213> ORGANISM: Homo sapiens

<400> SEQUENCE: 21
ttcataatgc caagacaaag ccgc                                    24

<210> SEQ ID NO 22
<211> LENGTH: 23
<212> TYPE: DNA
<213> ORGANISM: Mus musculus

<400> SEQUENCE: 22
ttattgagaa tagaggacat ctg                                     23

<210> SEQ ID NO 23
<211> LENGTH: 21

```
<212> TYPE: DNA
<213> ORGANISM: Mus musculus

<400> SEQUENCE: 23
atgctcagaa aactccataa c                                              21

<210> SEQ ID NO 24
<211> LENGTH: 23
<212> TYPE: DNA
<213> ORGANISM: Mus musculus

<400> SEQUENCE: 24
aacagtattc tttctttgca tgg                                            23

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 25
atgctcataa aactccataa c                                              21

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 26
aacagtattc tttctttgca gc                                             22

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 27
gagagtaggg tactgggttt                                                20

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 28
agcacctact atccagacac t                                              21

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 29
```

```
gtagtccata ccatgagagt a                                            21
```

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 30

```
tgggccgccc tagtcacc                                                18
```

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 31

```
cgtttggcct tagggttcag                                              20
```

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 32

```
Asp Glu Asn Gly Asn Tyr Pro Leu Gln Cys
 1               5                  10
```

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 33

```
caagaaaggt accctactct c                                            21
```

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 34

```
agtaatggcc atggtagcac c                                            21
```

<210> SEQ ID NO 35
<211> LENGTH: 42
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 35

```
gtacccaatg caaacccaaa tgcaaaccca aatgcaaacc ca                     42
```

<210> SEQ ID NO 36
<211> LENGTH: 42
<212> TYPE: DNA
<213> ORGANISM: Artificial Sequence
<220> FEATURE:
<223> OTHER INFORMATION: Description of Artificial Sequence: oligonucleotide

<400> SEQUENCE: 36
gtactgggtt tgcatttggg tttgcatttg ggtttgcatt gg                      42

<210> SEQ ID NO 37
<211> LENGTH: 42
<212> TYPE: DNA
<213> ORGANISM: Artificial Sequence
<220> FEATURE:
<223> OTHER INFORMATION: Description of Artificial Sequence: oligonucleotide

<400> SEQUENCE: 37
catggtaatg caaacccaaa tgtagatccc aatgccaacc ca                      42

<210> SEQ ID NO 38
<211> LENGTH: 42
<212> TYPE: DNA
<213> ORGANISM: Artificial Sequence
<220> FEATURE:
<223> OTHER INFORMATION: Description of Artificial Sequence: oligonucleotide

<400> SEQUENCE: 38
catgtgggtt ggcattggga tctacatttg ggtttgcatt ac                      42

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: synthetic peptide

<400> SEQUENCE: 39

Asn Ala Asn Pro Asn Ala Asn Pro Asn Ala Asn Pro
1               5                 10

<210> SEQ ID NO 40
<211> LENGTH: 4
<212> TYPE: PRT
<213> ORGANISM: Artificial Sequence
<220> FEATURE:
<223> OTHER INFORMATION: Description of Artificial Sequence: synthetic peptide

<400> SEQUENCE: 40

Asn Val Asp Pro
1

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: synthetic peptide

<400> SEQUENCE: 41

Ala Ser Asn Glu Asn Met Glu Thr Met

```
<210> SEQ ID NO 42
<211> LENGTH: 48
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 42
gtacaagtgt acttgattcc atagtctcca tattttcatt ggaagcgg           48
```

SOMATIC TRANSGENE IMMUNIZATION AND RELATED METHODS

This application is a continuation-in-part (CIP) application of U.S. patent application Ser. No. 09/300,959, filed Apr. 27, 1999, now U.S. Pat. No. 7,279,462, Issued Oct. 9, 2007 which claims the benefit of provisional U.S. Patent Application No. 60/083,154, filed Apr. 27, 1998, both of which are incorporated herein in their entireties by this reference.

This invention was made in part with government support under grant number PO1 AI33204 and AI36467, awarded by the National Institutes of Health. The government has certain rights in the invention.

BACKGROUND OF THE INVENTION

In recent years, there has been an explosion of information on the new possibility of inducing immunity using nucleic acids, called DNA vaccination. Previous studies have shown that plasmid DNA introduced into an adult immunocompetent host could induce an antibody response (Tang et al., *Nature* 356:152-154 (1992)), it was soon demonstrated using the influenza virus that both humoral and cell-mediated could be induced, and these were sufficient for protection in vivo (Ulmer et al., *Science* 259:1745-1749 (1993); Fynan et al., *Proc. Natl. Acad. Sci. USA* 90:11478-11482 (1993)). It soon became evident that, DNA vaccines, also called genetic vaccines, have gone through a phase of exponential growth and found an application against a large variety of antigens. They have been applied to immunize against cancer (Conry et al., *Cancer Res.* 54:1164-1168 (1994); bacteria (Tascon et al., *Nat. Med.* 2:888-892 (1996); Huygen et al., *Nat. Med.* 2:893-898 (1996)); virus (Ulmer et al., supra, 1993; Fynan et al., supra, 1993; Raz et al., *Proc. Natl. Acad. Sci. USA* 91:9519-9523 (1994); Davis et al., *Vaccine* 12:1503-1509 (1994); Wang et al., *Proc. Natl. Acad. Sci. USA* 90:4156-4160 (1993); and parasites (Sedegah et al., *Proc. Natl. Acad. Sci. USA* 91:9866-9870(1994)).

This basis of DNA vaccination is the introduction into a host of the "blue-print" for vaccine molecules in a way that mimics viral infections without the infectious threat. The use of DNA vaccines can be of particular value in those instances in which vaccines are either ineffective or not yet available.

Genetic vaccines, while conceptually simple in their making, for example, a bacterial plasmid incorporating the coding region of interest, they are still fraught with a number of unresolved issues pertaining mainly to their biology at the site of injection and systemically. Genetic vaccines work along the same lines of recognition of antigen (B cells) and antigen processing and presentation (T cells) known and established for protein antigens or infectious pathogens.

It has been known for many years that eukaryotic DNA is per se scarcely immunogenic whereas prokaryotic (bacterial) DNA possesses properties relevant to immunogenicity. It has been known for some time that bacterial DNA could serve as adjuvant in immunization (Braun et al., *Proc. Soc. Exp. Biol. Med.* 119:701 (1965)). It was subsequently reported that mice immunized with *Escherichia coli* DNA complexed with methylated BSA in adjuvant produce significantly greater amounts of antibodies than mice immunized with calf thymus DNA (Gilkeson et al., *Clin. Immunol. Immunopathol.* 51:362-371 (1989); Gilkeson et al., *J. Immunol.* 142:1482-1486 (1989)). Earlier observations had already shown that bacterial DNA possesses immunostimulatory properties (Tokunaga et al., *J. Natl. Cancer Inst.* 72:955-962 (1984), a fact undisputed today (Messina et al., *Cell Immunol.* 147:148-157 (1993)). These stimulatory properties are apparently linked to a six-base nucleotide motif consisting of an unmethylated CpG dinucleotide (Krieg et al., *Nature* 374:546-549 (1995) expressed nearly twenty times more frequently in bacterial than in vertebrate DNA (Cardon et al., *Proc. Natl. Acad. Sci. USA* 91:3799-803 (1994)). Noncoding, immunostimulatory sequences (ISS)-enriched plasmid DNA or ISS oligonucleotides themselves stimulate immune responses to co-administered antigens (Roman et al., *Nat. Med.* 3:849-854 (1997)) by activating IFN-g, IL-12 and IL-18, all of which promote a Th1 response (Carson and Raz, *J. Exp. Med.* 186: 1621-1622 (1997)).

In 1992, plasmid DNA was shown to immunize against the very antigen it codes for (Tang et al., *Nature* 356:152-154 (1992)). Therefore, it was possible to immunize using foreign DNA controlled by a potent promoter for tissue expression. Inoculation of functional genes into somatic cells of adult immunocompetent animals is a simple way to mimic natural infection and initiate adaptive immunity (Ulmer et al., *Curr. Opin. Immunol.* 8:531-536 (1996)). Plasmid DNA containing antigen-coding sequences and regulatory elements for their expression can be introduced in tissues by parenteral injection (Wang et al., supra, 1993) or by particle bombardment (Tang et al., supra, 1993). Antibody production (B-cell immunity), and cell-mediated immunity of the helper or cytotoxic T cell-type, have been induced against viruses (Ulmer et al., supra, 1993), bacteria (Huygen et al., supra, 1996; Tascon et al., supra, 1996), parasites (Sedegah et al., supra, 1994), tumor antigens (Conry et al., supra, 1994), self antigens (Gilkeson et al., *J. Exp. Med.* 183:1389-1397 (1996); Waisman et al., *Nat. Med.* 2:899-905 (1996)) and allergens (Raz et al., *Proc. Natl. Acad. Sci. USA* 93:5141-5145 (1996)).

Typically, injections of plasmid DNA via the intramuscular or intradermal route yields both antibody and cellular responses with long-lasting immunity preferably induced by multiple DNA inoculations (Sedegah et al., supra, 1994; Xiang et al., supra, 1994). The transgene product is, however, rarely found in the circulation (Davis et al., supra, 1993), and little is known about where and how antigen presentation occurs.

From a practical stand-point, immunization via DNA inoculation relies on in vivo transfection, production and possibly secretion of the transgene product, and antigen presentation by specialized cells. However, in most studies, neither the in vivo transfected cells nor the antigen presenting cells involved in this process have been identified. Expression of foreign DNA under the control of viral promoters (Tang et al., supra, 1992; Ulmer et al., supra, 1993; Davis et al., supra, 1993; Raz et al., supra, 1994; Wang et al., supra, 1993; Huygen et al., supra, 1996; Tascon et al., supra, 1996; Sedegah et al., supra, 1994; Dollan et al., supra, 1996) limit tissue specificity. Therefore, no control of expression is possible other than the site of DNA inoculation.

Although genetic vaccines have been used successfully, there remains a need to develop more effective methods to exploit the immunogenic potential of genetic vaccines. The present invention satisfies this need and provides related advantages as well.

SUMMARY OF THE INVENTION

The invention provides a method for stimulating an immune response by administering to a lymphoid tissue a nucleic acid molecule comprising an expression element operationally linked to a nucleic acid sequence encoding one or more heterologous epitopes. The heterologous epitope can be inserted into a complementarity-determining region of an immunoglobulin molecule. The invention also provides a nucleic acid molecule comprising a hematopoietic expression element operationally linked to a nucleic acid sequence encoding a heterologous polypeptide. The invention also provides a method of treating a condition by administering a nucleic acid molecule comprising a hematopoietic cell expression element operationally linked to a nucleic acid sequence encoding a heterologous polypeptide, wherein the nucleic acid molecule is targeted to a hematopoietic cell.

BRIEF DESCRIPTION OF THE DRAWINGS

FIG. 5 shows the nucleotide sequence of genomic DNA clones corresponding to the productively rearranged VDJ region of γ1WT-TAC DNA. A 520 bp fragment was amplified from (1) genomic DNA extracted from a spleen inoculated 17 days earlier with plasmid DNA γ1WT-TAC, and (2) J558L cells constitutively harboring plasmid DNA γ1WT (Sollazzo et al., supra, 1989). The amplified products were cloned and sequenced using two different primers from opposite directions. The top nucleotide sequence refers to γ1WT-TAC and serves as a reference. SP7-SP12 identify six clones originated from splenic genomic DNA. TR35-TR38 identify four genomic DNA clones derived from transfectoma cells. The CDR and framework regions (FR) are indicated. This study indicates that after injection in vivo the transgene does not undergo somatic mutation.

DETAILED DESCRIPTION OF THE INVENTION

Figure 1:
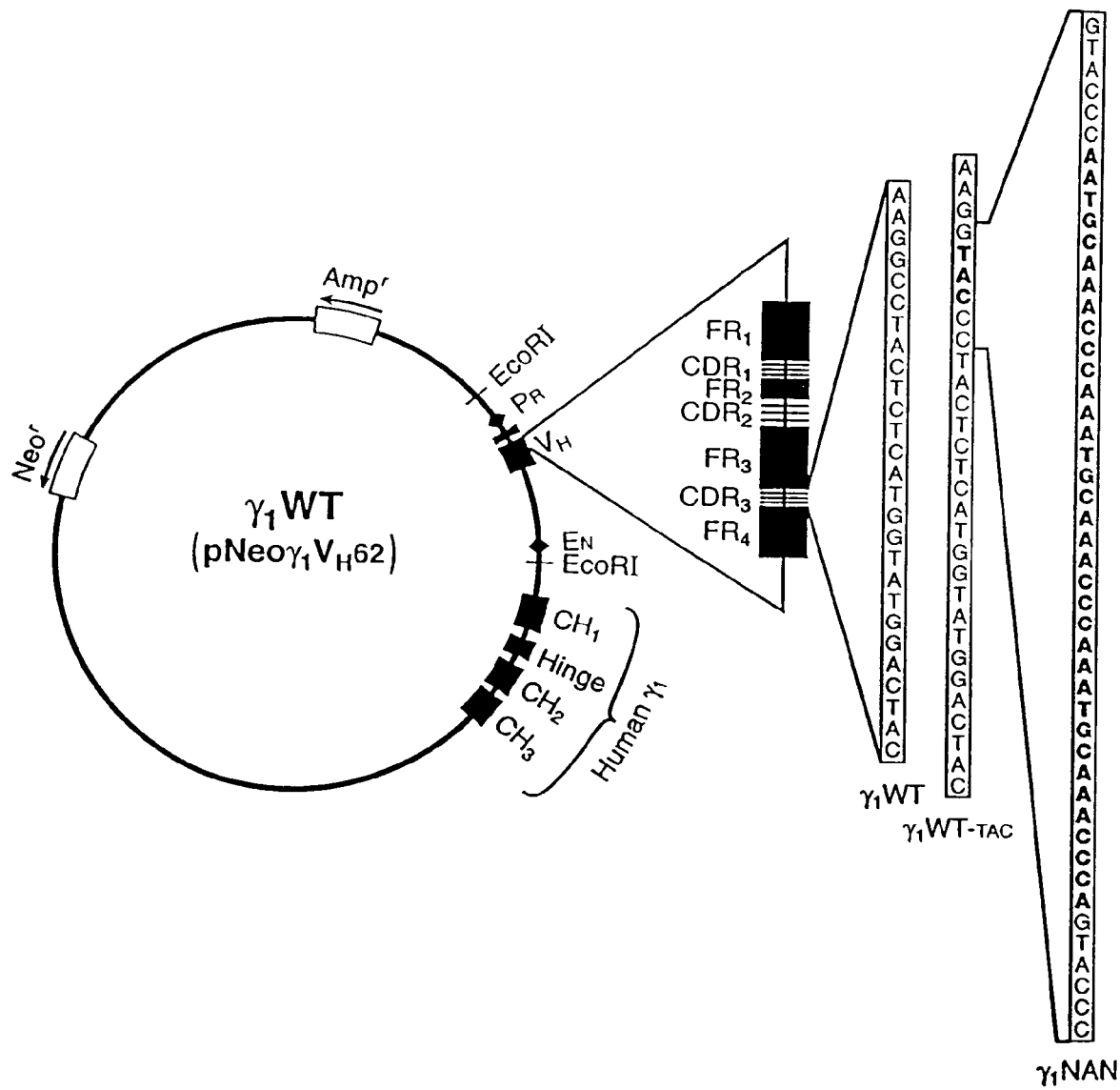
FIG. 1 shows a schematic representation of plasmid DNA γ1WT and its γ1WT-TAC and γ1NANP variants. The γ1WT H chain construct is the product of the fusion between a human γ1 constant (C) region gene present in the plasmid vector pNeoγ1 with the murine $V_H^{62}$ gene (2.3 kb) (Sollazzo et al., supra, 1989). The $V_H$ region gene is productively rearranged and the C region gene is in genomic configuration. Variants γ1WT-TAC and γ1NANP contain the nucleotide insertions shown in bold characters in CDR3. Each plasmid DNA carries the regulatory elements, promoter (Pr) and enhancer (En) needed for tissue-specific expression. In plasmid DNA γ1NANP the human γ1 C region gene is joined to a productively rearranged murine variable (V) region gene modified in the third complementarity determining region (CDR3) by introduction of the nucleotide sequence coding for three Asn-Ala-Asn-Pro repeats. In these plasmids, the promoter and enhancer elements are those constitutively existing in Ig H chain genes. $Neo^r$=neomycin resistance gene; $Amp^r$=ampicillin resistance gene; PR=promoter; EN=enhancer; $C_H$=heavy chain C region; $V_H$=heavy chain variable region; FR=framework region; CDR=complementarity determining region.

The present invention provides a rational and effective approach to immunization and is predicated on the induction of antibody and T cell responses following inoculation of a polypeptide encoded by a nucleic acid molecule, for example, an immunoglobulin H chain gene, targeted to hematopoietic cells such as lymphocytes in a lymphoid tissue. The methods of the invention can be used to initiate immunity, establish immunologic memory and program the immune response in a reproducible way from a single inoculation of a nucleic acid molecule such as plasmid DNA.

The invention provides a method for stimulating an immune response, comprising administering to a lymphoid tissue a nucleic acid molecule comprising an expression element operationally linked to a nucleic acid sequence encoding one or more heterologous epitopes.

The methods of the invention are based on an effective method for delivering a nucleic acid molecule, which can serve as a vaccine, to primarily but not exclusively B cells, which can preferably be in secondary lymphoid organs, and hence program the immune system to produce large amounts of immunogenic molecules. The method for delivering a nucleic acid molecule such as a DNA vaccine is termed somatic transgene immunization (STI). The methods of the invention are effective at stimulating an immune response because the nucleic acid molecule is targeted to hematopoietic cells such as B lymphocytes in lymphoid tissues. The effectiveness of the methods result from the self-renewing property of antigenized antibody genes harbored in B lymphocytes and the constitutive ability of activated B lymphocytes to synthesize many copies of transgene products. STI can be used as a vaccination process that is designed to exploit one of the body's is most efficient and exquisite machineries for protein production.

In one embodiment, the variable region of antibodies can be re-engineered to code for discrete sequences of heterologous antigens to impart the molecule new antigenic and immunogenic properties, called antibody antigenization. This approach allows modification of the complementarity determining regions (CDR) of the variable domain of an immunoglobulin so that, after antigenization, antibodies become structural mimics of antigens in a way that leads to induction of B-cell and T-cell immunity. Consequently, inoculation of antigenized H chain genes and synthesis of transgenic Ig by the host during STI is a way to provide the organism with exogenous B-cell and T-cell epitopes. Methods of generating antigenized immunoglobulins is described, for example, in U.S. Pat. No. 5,583,202, issued Dec. 10, 1996, and U.S. Pat. No. 5,658,762, issued Aug. 19, 1997.

The present invention provides the combined use of STI and antigenized antibody genes as a new method to induce antigen-specific immunity, antibody and T cell mediated. In addition to antigenized antibodies, the methods of the invention for stimulating an immune response can use a nucleic acid molecule expressing one or more heterologous polypeptides. The heterologous polypeptide is operationally linked to an expression element allowing expression of the polypeptide in all targets in a lymphoid tissue. Similar to an antigenized antibody, the methods exploit the polypeptide expression capabilities of hematopoietic cells targeted upon administration of a nucleic acid molecule to a lymphoid tissue. The heterologous polypeptide can encode one or more epitopes capable of eliciting an immune response.

The methods of the invention are useful, for example, for stimulating an immune response against pathogens, tumor antigens and pathological processes. The present invention can be used to stimulate an immune response against infectious agents including, viruses, for example, immunodeficiency virus 1 and 2, hepatitis viruses, papilloma virus, influenza virus, Epstein-Barr virus, cytomegalovirus, Japanese encephalitis virus, Dengue virus, and other retroviruses/lentiviruses; protozoa, for example, parasites causing malaria, leishmaniasis, trypanosomiasis, filariasis, toxoplasmosis, hookworm, tapeworm; yeast, for example, *Candida albicans*; bacteria, in particular pathogenic bacteria such as *Mycobacterium tuberculosis, Mycobacterium leprae*, and bacteria that cause colera, *Mycoplasma/Ureaplasma*, and spirochetes such as treponema pallidum, borrelia, leptospira; toxins, for example, botulinum, anthrax, snake toxins, insect toxins, and warfare-related chemical toxins.

The methods of the invention can also be used to stimulate an immune response to pathological or disease conditions. The pathological or disease conditions can be, for example, tumors, including those expressing antigens such as prostate specific antigen (PSA), Her-2/neu, p53, MUC-1, telomerase, carcinoembryonic antigen (CEA), melanoma associated antigens (MAGE), thyrosinase, gp100; autoimmune diseases, for example, diabetes, myasthenia gravis, multiple sclerosis, rheumatoid arthritis, Crohn's disease, uveitis; allergy, for example, dermatitis and athsma; metabolic disorders, for example, hypertension, diabetes, hypercholesterolemia; endocrine disorders, for example of the thyroid, adrenals, pituitary, ovary, testis; mental disorders, for example, bipolar disorders, schizophrenia; pain, for example, modulation of neurotransmitters and neuropeptides; blood disorders, for example, coagulation, anemias, thrombocytopenia; and dental disorders, for example, caries. The methods of the invention can also be used to control reproduction, for example, contraceptive vaccination. The methods of the invention can additionally be used for treating transplant patients, for example, solid organ by inducing transplantation, and bone marrow transplantation, anti-HLA immunity. The present invention can be used for the production of human and animal vaccines against viruses, parasites, bacteria, allergy, autoimmune disease, and tumors. The methods of the invention are useful for stimulating an immune response to treat or prevent a condition as described above.

The methods of the invention include the step of administering a nucleic acid molecule encoding one or more heterologous epitopes to a secondary lymphoid tissue. The secondary lymphoid tissue can be spleen, lymph nodes, mucosa-associated lymphoid tissue (MALT), including tonsils and Payer's patches, and the nasal-associated lymphoid tissue (NALT) such as the Waldeyer's ring, and the urogenital lymphoid tissue. A variety of methods can be used to administer a nucleic acid molecule to a lymphoid tissue. For example, a nucleic acid molecule can be directly injected into a lymphoid tissue such as a lymph node. A nucleic acid molecule can also be directly injected into the spleen of an individual, for example, using endoscopy-guided fine needle injection. Additional methods include the intravenous injection of DNA encapsulated into (immuno)-liposomes or biodegradable beads of various chemical structure for time-controlled release, for example, hyaluronic acid. Additional methods include the (intra)-nasal delivery of DNA encapsulated into (immuno)-liposomes or biodegradable beads or various chemical structure for time-controlled release such as hyaluronic acid. Additional methods include the oral delivery of DNA encapsulated into (immuno)-liposomes or biodegradable beads or various chemical structure for time-controlled release, for example, hyaluronic acid, in a suitable acid-resistant pharmaceutical vehicle, or engineered in live attenuated bacteria, for example, *Salmonella typhi*.

As used herein, the term "epitope" refers to a molecule or fragment thereof capable of stimulating an immune response. A polypeptide epitope is at least three amino acids in length for antibody responses and at least eight amino acids in length for T cell responses.

As used herein, the term "heterologous polypeptide" when used in reference to a nucleic acid molecule means that the polypeptide is encoded by a nucleic acid sequence operationally linked to an expression element, where the polypeptide is not naturally found linked to the expression element. As such, the polypeptide is heterologous to the expression element.

Similarly, the term "heterologous epitope" refers to an epitope encoded by a nucleic acid sequence operationally linked to an expression element, where the epitope is not naturally found linked to the expression element. When a heterologous epitope is contained in an immunoglobulin, the epitope is not ordinarily found in the immunoglobulin. Hence, the immunoglobulin contains a heterolgous epitope sequence. Such heterologous epitope sequences can include antigenic epitopes as well as receptor-like binding domains or binding regions that function as receptor sites, for example, the human CD4 binding domain for HIV, hormone receptor binding ligands, retinoid receptor binding ligands and ligands or receptors that mediate cell adhesion.

The epitope encoded by the nucleic acid molecules of the invention is operationally linked to an expression element. As used herein, an "expression element" is a nucleic acid regulatory element capable of directing expression of genetic element such as an epitope. An expression element can include, for example, promoters and/or enhancers capable of allowing expression of an operationally linked genetic element such as a genetic element encoding a polypeptide or epitope. Particularly useful promoters and enhancers are those that function in hematopoietic cells, termed "hematopoietic cell expression elements." Such hematopoietic expression elements are capable of allowing expression in a cell of hematopoietic origin, for example, a B cell, T cell or dendritic cell. These promoters and enhancers can be specific for a hematopoietic cell, or they can function in hematopoietic cells as well as other cell types.

The methods of the invention can employ a nucleic acid molecule encoding an epitope expressed as a fusion with a cytokine. The cytokine can be any cytokine, including, for example, granulocyte-macrophage colony-stimulating factor (GM-CSF), interleukin-2 (IL-2), interleukin-4 (IL-4), interferon-$\gamma$ (INF-$\gamma$), interleukin-5 (IL-5), interleukin-6 (IL-6), interleukin-10 (IL-10) and interleukin-12 (IL-12) and the like. Alternatively, a nucleic acid molecule such as plasmid DNA coding for an antigenized H chain gene can be concomitantly administered with a nucleic acid molecule such as plasmid DNA coding for a cytokine. One skilled in the art can select a cytokine for fusion with a polypeptide based on a desired type of immune response which can depend on the type of antigen used to elicit an immune response.

The nucleic acid molecule used in the invention can encode an immunoglobulin molecule containing one or more heterologous epitopes. The epitopes can be inserted into a complementarity-determining region (CDR) of the immunoglobulin molecule (see, for example, Kabat et al., *Proteins of Immunological Interest*, U.S. Department of Health and Human Services, Bethesda Md. (1987)). The epitope can be inserted within CDR1, CDR2 and/or CDR3. Furthermore, one or more epitopes can be inserted within any of the CDRs. Thus, the same epitope can be inserted multiple times within a single CDR or can be inserted multiple times within different CDRs. Different epitopes can also be inserted within the same CDR or can be inserted within different CDRs. Thus, a single CDR can have a single epitope, multiple copies of the same epitope, or two or more different epitopes in the same CDR. It is likely that as many as 6 epitopes, or possibly more, can be inserted into the three CDRs of a variable region. These methods utilize antigenized immunoglobulins which are described in U.S. Pat. Nos. 5,583,202 and 5,658,762.

Generally, when more than one epitope is administered to stimulate an immune response, the multiple epitopes are encoded on the same nucleic acid molecule. When encoded on the same plasmid, the multiple epitopes can be operationally linked to the same expression element and expressed as a fusion polypeptide, or the multiple epitopes can be expressed from multiple copies of the expression element. Multiple epitopes can also be expressed from different expression elements. Furthermore, the same epitope can be administered in different nucleic acid molecules such as different plasmids. Similarly, different epitopes can be administered in one nucleic acid molecule or can be administered in multiple nucleic acid molecules such as on different plasmids. Using different nucleic acid molecules encoding multiple epitopes allows the administration of many more epitopes than could be encoded on a single nucleic acid molecule.

The immunoglobulin molecules useful in the invention can contain the variable region of a heavy or light chain, or a functional fragment thereof. For example, a single CDR can be a functional fragment if the immunoglobulin, as used herein as an antigenized antibody, functions to stimulate an immune response. The immunoglobulin can also comprise two or three CDRs or a variable region as described above. Additionally, the immunoglobulin molecules useful in the invention can be a heavy chain or a light chain. The effector function of the immunoglobulin molecule can be conferred by the constant region of the immunoglobulin molecule. Therefore, the immunoglobulin molecule can include a constant region. The constant region can be derived, for example, from human, primate, mouse, rat, chicken or camel, as desired. However, it is understood that a constant region is not required for the immunoglobulin of the invention if the functional fragment of the immunoglobulin functions to stimulate an immune response.

The invention also provides a nucleic acid molecule comprising an expression element operationally linked to a nucleic acid sequence encoding one or more heterologous polypeptides. The heterologous polypeptide can function as one or more epitopes. Furthermore, the epitope can be expressed as a fusion with a cytokine. When an epitope is expressed as a fusion polypeptide, for example, a fusion with a cytokine, the epitope can be fused proximal to a cytokine, or there can be intervening sequence between the epitope and the cytokine. The cytokine can be, for example, GM-CSF, IL-2, IL-4, INF-$\gamma$, IL-5, IL-6, IL-10 and IL-12. The expression element of the nucleic acid molecules of the invention can be a hematopoietic expression element.

The methods of the invention can be used to stimulate an immune response. The immune response elicited can be an antibody response, a CD4 T cell response or a CD8 T cell response. Two major classes of T cells, termed T helper cells and T cytotoxic cells, can be distinguished. The classification of T cells into T helper cells and T cytotoxic cells is generally based on the presence of either CD4 or CD8 protein, respectively, on the cell surface. The methods of the invention can be used to elicit an antibody response, a CD4 T cell response or a CD8 T cell response, or any combination of two or more of these responses, including all three responses. For example, the methods of the invention can be used to stimulate an antibody response and a CD4 T cell response. The methods of the invention can also be used to stimulate an antibody response and a CD8 T cell response. Additionally, the methods of the invention can be used to stimulate a CD4 T cell response and a CD8 T cell response. Furthermore, the methods of the invention can be used to stimulate an antibody response, a CD4 T cell response and a CD8 T cell response. In addition, the methods of the invention can be used to stimulate multiple CD4 T cell responses, for example, two or more, three or more, or five or more CD4 T cell responses. Similarly, multiple CD8 T cell responses can be stimulated using methods of the invention. Thus, depending on the type of immune response desired for a given type of antigen or condition, one skilled in the art can select the most appropriate immune response, an antibody, CD4 T cell or CD8 T cell response, to provide an optimized immune response for a given condition or potential condition.

The success of DNA vaccination is determined by a series of factors, all of which depend on the efficiency of gene delivery and gene expression in vivo. Strategies have been developed for receptor-mediated gene delivery (Wu et al., *J. Biol. Chem.* 264:16985-16987 (1989)) to exploit specific structures on somatic cells and their mechanisms to internalize macromolecules. Moreover, targeted delivery and expression of DNA can also be gauged through the specificity of regulatory elements such as promoters and enhancers, which allow the transgene to be transcribed and translated in tissues.

The methods disclosed herein were developed keeping in mind factors such as the efficiency of in vivo transfection, including DNA uptake by host cells, the efficiency with which transfected cells utilize the DNA and synthesize the transgene product, and the ability of in vivo transfected cells to serve as antigen-presenting cells. Since during natural infection pathogens activate lymphocytes in lymphoid organs, likewise it was likely that the most effective way to mimic natural infection would be to direct immunization to sites of immune-response induction using transgenes under the control of lymphoid tissue-specific regulatory elements.

As disclosed herein, the inoculation of plasmid DNA coding for a rearranged immunoglobulin (Ig) H chain gene with B cell-specific promoter and enhancer elements can be used to stimulate an immune response, leads to expression of these genes in B lymphocytes. Specifically, this approach reaches two objectives: exploit B lymphocytes as powerful minifactories of antigenic material and use them as antigen-presenting cells (APC). Therefore, efficient utilization of the foreign DNA and antigen presentation by the very cells harboring the transgene is addressed in one operational event. Thus, the targeting of nucleic acid molecules encoding a heterologous epitope to a lymphoid tissue exploits the natural high level expression of immunoglobulins in B lymphocytes.

As disclosed herein, a single inoculation of the H chain gene targeted to spleen lymphocytes is sufficient to initiate immunity (see Example I), establish immunologic memory (see Example V), and program the immune response predictably and reproducibly (see Examples II and IV). Experiments in murine systems, in vitro and in vivo, demonstrate that the H chain polypeptides of the transgene associate with endogenous light chains (Example IV), and transgenic Ig are invariably secreted in amounts between 15 and 30 ng/ml (Example I). The synthesis of transgenic Ig is followed by an immune response consisting in antibodies and T cells specific for antigenic determinants of transgenic Ig by day 5-7. The antibody response remains detectable almost indefinitely. Upon booster injection with an appropriate antigen, a typical secondary immune response is induced. This process is termed somatic transgene immunization (STI) (see Example I).

In its simplest form STI is reflected by a model in which plasmid DNA is injected directly into a lymphoid organ where it reaches follicles and within them, the B lymphocytes. The hypothetical scenario that follows is described hereunder. A first set of B lymphocytes (B1) uptake and immediately begin utilizing the H chain DNA molecule which undergoes transcription and translation into a functional H chain. A fraction of nascent H chain polypeptides is secreted in association with endogenous L chain as transgenic Ig carrying heterologous epitopes (antigenized transgenic Ig). This event sets in motion the immune response. A second set of B lymphocytes (B2) respond to the antigenic determinants of secreted transgenic Ig by producing antibodies. Transgenic Ig also act by activating Th cells. T cell determinant peptides are processed and presented either by B lymphocytes harboring the transgene (direct presentation) or by proximal interdigitating dendritic cells (IDC) (cross-priming). The process of immunity spreads rapidly to other secondary lymphoid organs through secreted transgenic Ig reaching the bloodstream and the lymphatic system. Activated T cells can follow a similar pattern and emigrate from the initial site of activation to encounter the same peptides carried in the form of transgenic Ig in distal lymphoid organs. As the response evolves in time, transgenic Ig alone or complexed with specific antibodies are trapped by follicular dendritic cells (FDC) and stored along the dendrites to be re-utilized during memory responses.

B lymphocytes are the target cell population of STI as demonstrated by PCR-amplification of genomic DNA from purified B cells (see Example II). Although the mechanism of DNA uptake by B cells is not completely understood, it is likely that internalization is mediated either by membrane Ig with anti-DNA reactivity, which exist in the normal B cell repertoire (Holmberg et al., *Immunol. Rev.* 93:147-169 (1986); Glotz et al., *J. Immunol.* 141:383-390 (1988)), by a non-Ig receptor for DNA (Bennett et al., *J. Clin. Invest.* 76:2182-2190 (1985)), or by the class II HLA molecule (Filaci et al., *Eur. J. Immunol.*, 28:3968-3979, (1999)).

The variable region of antibodies can be re-engineered to code for discrete sequences of heterologous antigens to impart the molecule new antigenic and immunogenic properties, antibody antigenization (Zanetti, *Nature* 355:466-477 (1992)). This approach enables one to modify ad hoc the complementarity-determining regions of the variable (V) domain so that, following antigenization, antibodies become structural mimics of antigens in a way that leads to induction of B-cell (Billetta et al., *Proc. Natl. Acad. Sci. USA* 88:4713-4717 (1991); Lanza et al., *Proc. Natl. Acad. Sci. USA* 90:11683-11687 (1993); Rigaudy et al., *DNA Cell Biol.* 13:585-591 (1994); Zaghouani et al., *Proc. Natl. Acad. Sci. USA* 92:631-635 (1995); Cook and Barber, *Vaccine* 13:1770-1778 (1995); Corthesy et al., *J. Biol. Chem.* 271:33670-33677 (1996); Cook and Barber, *Aids Res. Hum. Retroviruses* 13:449-460 (1997)) and T-cell (see Example IV and Zanetti et al., *Immunol. Rev.* 130:125-150 (1992); Zaghouani et al., *J. Immunol.* 148:3604-3609 (1992); Zaghouani et al., *Science* 259:224-227 (1993); Billetta et al., *Eur. J. Immunol.* 25:776-783 (1995) immunity. Consequently, inoculation of antigenized H chain genes and synthesis of transgenic Ig by the host during STI is a way to provide the organism with exogenous B- and T-cell epitopes.

In transgenic Ig, B-cell epitopes are expressed with controlled geometry and spatial characteristics to approximate the shape of native antigens from which they derive. Since the antigen receptor on B lymphocytes recognizes antigens through their three-dimensional structure and binds establishing interactions over large sterically and electrostatically complementary areas, the expression of B cell epitopes in antibody loops induce antibodies cross-reactive with a native structure. It has been demonstrated that heterologous peptides conformationally-constrained within antibody CDR loops have sufficient structure stability and conformation to interact with somatic receptors in a discriminating way (Billetta et al., supra, 1991; Lanza et al., supra, 1993; Rigaudy et al., supra, 1994; Zaghouani et al., supra, 1995; Cook et al., supra, 1995; Corthesy et al., supra, 1996; Cook et al., supra, 1997). Activation of T cells, on the other hand, requires that antigen be presented in the form of small peptides. As disclosed herein, T-cell peptides expressed in CDR loops are easily processed and presented in the context of major histocompatibility complex (MHC) molecules (see Example IV and Zanetti et al., supra, 1992; Zaghouani et al., supra, 1992; Zaghouani et al., supra, 1993; Billetta et al., supra, 1995). Thus, during somatic transgenesis, B cells harboring and synthesizing transgenic Ig become a self-renewing source of T cell peptides. Processing and presentation is mediated by B cells directly or through cross-priming of other antigen presenting cells (APC).

The dual immunogenic potential of transgenic Ig is best understood by analyzing the intracellular journey of nascent antigenized H chain polypeptides. These polypeptides are subject to quality control mechanisms within the endoplasmic reticulum (Sitia and Cattaneo, *Synthesis and assembly of antibodies in natural and artificial environments*, Hardwood Academic Publishers, Luxembourg (1995)). Newly formed H chain polypeptides that are properly folded and associate with the endogenous light chain they proceed through secretion along the secretory pathway. The secreted molecules have direct bearing on the induction of B cell immunity. Alternatively, misfolded H chains are subject to degradation by local proteases (Klausner and Sitia, *Cell* 62:611-614 (1990)), giving origin to peptides, including those in the 9-15 amino acid range, which combine with MHC molecules and are exported to the cell surface. Cumulative data suggest that CDR loops may be sites for preferential proteolytic cleavage within the V region. Neither the position of heterologous peptides relative to the N terminus nor the flanking residues appear to influence this process and overall presentation to T lymphocytes.

When a transgene coding for a strong Th cell determinant is inoculated into mice, a vigorous CD4 T cell response is elicited (Gerloni et al., *J. Immunol.,* 162:3782-3789 (1999)). The activation of Th cells is reproducible and always hallmarked by the concomitant production of large amounts of IL-2 and proportional amounts of IFN-γ and IL-4. Conventional DNA immunization favors Th1 responses (Roman et al., supra, 1997; Chu et al., *J. Exp. Med.* 186:1623-1631 (1997)). Thus, STI activates uncommitted CD4 T cells.

As to class I MHC presentation, earlier studies had shown that B lymphoma cells engineered with a H chain transgene coding for a virus CTL epitope present the class I peptide to a T cell clone specifically (Zanetti et al., supra, 1992; Billetta et al., supra, 1995). In mice inoculated with the same transgene, a specific CD8 T response was measured. The results disclosed herein indicate that STI serves as an endogenous source of T cell peptides and has fulfilled basic requirements for immunogenicity in vivo (see Example IX).

Collectively, the results disclosed herein indicate that STI is an effective system for inciting immunity in vivo. STI induces immunity using B cells for the protracted manufacturing of immunogenic molecules (a B cell can produce $10^3$ molecules of antibody/second (Langman and Cohn, *Mol. Immunol.* 24:675-697 (1987)), without harming the immune system in the process. Moreover, STI can be used to direct the synthesis of heterologous antigenic determinants by B lymphocytes as a self-determined event. STI integrates the immune system itself into the immunization process: B lymphocytes produce immunogenic molecules of predetermined antigenicity and function as APC.

Secreted transgenic Ig can target APC via the Fc receptor for secondary antigen processing and presentation, hence acting as source of antigen peptides for lymphoid tissues distal from the site of initiation of immunity. From this it is easy to see how immunity can spread from the initial site. In fact, cells harboring the transgene do not colonize other lymphoid organs (see Example II). Transgenic Ig emigrate from the organ of inoculation and diffuses to other districts of the lymphoid system through the bloodstream and the lymphatics. There they can promote immunity de novo. Unlike conventional immunization systems, where antigen or antigen peptide in immunologic adjuvant activate T cells only in draining lymph nodes (Kearney et al., *Immunity* 1:327-339 (1994), during STI, mobilization of activated T cells together with the diffusion of soluble transgenic Ig facilitate spreading of T cell immunity throughout the body (see Example VIII).

STI allows one to express in B cells an Ig transgene starting any time during the adult life and involving only a discrete number of B cells (fewer than 0.07%). The results disclosed herein indicate that the physiological machinery provided by STI can be exploited to program immune response in an individual. STI has been exploited to identify cell types and dissect cellular networks during the immune response in vivo without interference by immunologic adjuvants. For instance, the IgM to IgG1 switch can be directed in vivo by inoculating a transgene chimerized with GM-CSF (Example VI) or by including a strong Th cell determinant (Zanetti et al., supra, 1998). The role of STI in the establishment of immunological memory has also been characterized (Example VII).

Most previous studies indicated that expression of the transgene, synthesis of the corresponding gene product, its presentation to immunocompetent cells and induction of immunity occur after repeated inoculations of plasmid DNA (Whalen and Davis, *Clin. Immunol. Immunopathol.* 75:1-12 (1995)). Most previous studies have targeted the muscle, a tissue with low replicative activity, using genes under the control of foreign viral promoters to initiate their transcription. In selected studies, the transgene has been shown to persist in the muscle in a non-integrated, extrachromosomal form for a long time (Nichols et al., Ann. N. Y. Acad. Sci. 772:30-39 (1995); Wolff et al., *Hum. Mol. Genet.* 1:363-369 (1992)), albeit the most efficient gene expression is achieved during active muscle generation (Wells and Goldspink, *Febs Lett.* 306:203-205 (1992)) or regeneration (Davis et al., *Ann. N. Y. Acad. Sci.* 772:21-29 (1995); Davis et al., *Hum. Gene Ther.* 4:151-159 (1993)). Targeting of plasmid DNA using tissue-specific regulatory elements for transcription has been done in a few instances only (Perales et al., *Proc. Natl. Acad. Sci. USA* 91:4086-4090(1994)).

During immunity to natural infection, lymphocytes are in general activated by the pathogen or by APCs in lymphoid organs. Mimicking natural infection through inoculation of genes under the control of tissue-specific regulatory elements directly targeted to a lymphoid tissue can help elucidate the way nucleic acids initiate immunity.

As disclosed herein, DNA inoculation was tested by directly inoculating into a lymphoid organ, the spleen. The plasmid DNA coding for an immunoglobulin heavy (H) chain gene under the control of tissue-specific promoter and enhancer elements was used (Banerji et al., *Cell* 33:729-740 (1983); Gillies et al., *Cell* 33:717-728 (1983); Grosschedl and Baltimore, *Cell* 41:885-897 (1985); Mason et al., *Cell* 41:479-487 (1985)). B lymphocytes, which are able to utilize the transgene physiologically and serve as APCs (Lanzavecchia, *Nature* 314:537-539 (1985)), are the cell type targeted in STI.

The methods disclosed herein can be used for immunization and can be used to study the immunogenicity of immunoglobulins in a way that is independent of the physical state of the protein and of the use of immunological adjuvants.

Immunization by inoculation of somatic cells with nucleic acids offers the possibility to evoke specific and often strong immune responses in the absence of immunological adjuvants (see Example I; Cohen, *Science* 259:1691-1692 (1993)). As disclosed herein, immunization with DNA should be not only possible but likely more effective using a gene possessing tissue-specific regulatory elements directly targeted to cells that can function as antigen-secreting as well as antigen-presenting cells (see Example I and VIII).

As disclosed herein, inoculation of somatic cells with nucleic acids results in tissue-specific targeting. Using STI successful initiation of immunity was achieved with in vivo targeting of a tissue with high replicative activity using a gene under the control of tissue-specific promoter and enhancer elements (Example I). The results presented herein are in contrast to what was previously known about DNA immunization, where DNA under the control of viral promoters inoculated into tissues with low replicative activity, for example, the muscle, from which the transgene or its product need to travel to the draining lymph node(s) in order to initiate an adaptive immune response (Nichols et al., supra, 1995; Wolff et al., supra, 1992).

As disclosed herein, direct targeting of the spleen with a gene under the control of lymphoid tissue-specific promoter and enhancer elements led to detection of transgene mRNA for at least four months, a much longer time compared with the few days reported for transfection of DNA under the control of a viral promoter into actively replicating cells (Sikes et al., *Hum. Gene Ther.* 5:837-844 (1994)).

Hypermutation in the VDJ region of the H chain transgene. Hypermutation usually occurs as the result of affinity maturation of antibodies during the course of the immune response and is localized around the V segment (Griffiths et al., supra, 1984). Nucleotide sequence analysis of VDJ coding regions present in genomic DNA of inoculated spleens showed essentially no mutational event (Example I). Absence of hypermutation during somatic transgene immunization is expected since the transgene lacks the transmembrane domain, making it difficult for antigen or anti-immunoglobulin antibodies to exert selective pressure on the B cells transduced in vivo.

Intraspleen inoculation of DNA containing viral enhancer-promoter sequences failed to induce an immune response (Raz et al., supra, 1994), and most studies on intramuscular inoculation have indicated that multiple DNA injections are needed for a measurable and sustained antibody response (reviewed in (Whalen and Davis, supra, 1995; Whalen et al., *Ann. N. Y. Acad. Sci.* 772:64-76 (1995)). Therefore, it is likely that transfection of spleen B lymphocytes with an immunoglobulin H chain gene under the control of tissue-specific promoter and enhancer elements was crucial to successful initiating and sustaining of the immune response.

As disclosed herein, an endogenous antigen, the transgene H chain product, secreted in low amounts (15-30 ng/ml) is per se immunogenic rather than tolerogenic (see Example I). This is in agreement with earlier experiments (Reth et al., *Nature* 290:257-259 (1981)) showing the enhancing effect of minute amounts (10 ng) of isologous anti-idiotype on the idiotypic response following antigen immunization. The serum concentration of transgene H chain immunoglobulins detected in mice is compatible with the estimated minimum antibody concentration (20 ng/ml) necessary to form antigen:antibody complexes (Langman and Cohn, *Mol. Immunol.* 24:675-697 (1987)). Protein antigens are more immunogenic when administered in aggregated form (Dresser, *Immunology* 5:378-388 (1962); Golub and Weigle, *J. Immunol.* 102:309-315 (1969)) or complexed with antibodies (Klaus, *Nature* 278:354-355 (1979a); Klaus, *Adv. Exp. Med. Biol.* 114:289-294 (1979b)), as this results in a greater uptake by macrophages and dendritic cells (Tew et al., *Immunological Rev.* 53:175-201(1980)). Consequently, the continuous production of anti-immunoglobulin antibodies was likely sustained by immune complexes (H chain transgene immunoglobulins/anti-immunoglobulins) captured and stored by follicular dendritic cells, and subsequently presented to T cells, which are required for anti-immunoglobulin responses in vivo (Coulie and Van Snick, *J. Exp. Med.* 161:88-97 (1985); Nemazee, *J. Exp. Med.* 161:242-256 (1985)).

The results described herein in Example I indicate similarities between the immune response triggered by intraspleen inoculation of DNA and immunity against foreign antigens. Antigens that invade an organism through the skin are sequestered by dendritic cells (Langherans cells) and vehicled to secondary lymphoid organs (lymph nodes and spleen). Antigens that invade the organism via the blood are trapped in the white pulp of the spleen where dendritic cells of the follicular zone capture, process and present antigen to B and T lymphocytes (Anderson, in *Structure and Organization of the Lymphatic System*, Oppenheim and Shevach, eds., Oxford University Press, New York (1990)). Clonal activation and expansion of B and T cells begin following this initial step. STI initiates the process of immunity directly within the anatomical structures which constitute the afferent point of foreign antigen during a conventional immune response. The fact that the transgene is harbored in B lymphocytes (Xiong et al., *Proc. Natl. Acad. Sci. USA* 94:6352-6357 (1997)) insures a protracted synthesis and secretion of transgenic immunoglobulins in quantities and form sufficient for the initiation of immunity and the establishment of immunologic memory.

The type of immunogenic stimulus offered by somatic transgene immunization can persist in the organism as long as B lymphocytes harboring the transgene live and secrete the transgene product. In the mouse, spleen B lymphocytes are distinguished into short-lived (3-4 days) (Rocha et al., *Eur. J. Immunol.* 20:1697-1708 (1990)), representing approximately one third, and long-lived (>6 weeks in the resting state) (Forster and Rajewsky, *Proc. Natl. Acad. Sci. USA* 87:4781-4784 (1990)), representing approximately two thirds of the total population (Osmond, *Curr. Op. Immunol.* 3:179-185 (1991)). After a single intraspleen inoculation, the transgene persisted functionally for four months. Thus, it appears that the cells transfected in vivo were long-lived B lymphocytes (see Example II). The transgene can persist in the host throughout the life span of the host B cell to disappear when the B cell dies. This, together with the "depot effect" played by follicular dendritic cells, may be critical in the induction and maintenance of memory B cells whose half-life in the absence of antigen is estimated in the order of 2-3 weeks (Gray and Skarvall, *Nature* 336:70-73 (1988)).

B lymphocytes are generated in the bone marrow and localize in secondary lymphoid organs and in the blood throughout life (Osmond, *Immunol. Rev.* 93:103-124 (1986); Rajewsky, *Curr. Opin. Immunol.* 4:171-176 (1992); Rolink Melchers *Curr. Opin. Immunol.* 5:207-217 (1993)). Upon activation by antigen, a B cell can produce between $1 \times 10^3$ and $8 \times 10^4$ molecules of immunoglobulin(Ig)/cell/sec (Jerne, *Immunol. Rev.* 79:5-24(1984); Langman and Cohn, supra, 1987). Consequently, B cells are formidable minifactories of proteins in mammals. B lymphocytes can also present antigen to T lymphocytes: (i) antigens internalized via their membrane Ig receptor (Lanzavecchia, supra, 1985), and (ii) peptides of secretory proteins including their own Ig (Weiss and Bogen, *Proc. Natl. Acad. Sci. USA* 86:282-286 (1989); Billetta et al., *Eur. J. Immunol.* 25:776-783 (1995)). Because of these properties, B lymphocytes constitute an ideal substrate for strategies of gene targeting and immunization with plasmid DNA.

The goal of immunization against pathogens (vaccination) is to generate immunity that confers protection (Salk and Salk, *Science* 195:834-847 (1977)). In many instances, both humoral and cellular responses, together with the induction of immunologic memory from the first injection, are needed. Furthermore, the antigenicity and immunogenicity of a candidate vaccine may be enhanced if the relevant epitopes are expressed in an appropriate three-dimensional conformation (Zanetti et al., *Immunol. Today* 8:18-25 (1987)).

The methods of the invention are useful for stimulating an antibody response. Hypervariable loops of immunoglobulins (Ig) can be used to express discrete peptide sequences of antigens, antigenized antibodies (Zanetti, supra, 1992). These antibodies serve as immunogens that focus the immune response on specific B or T cell epitopes (Zanetti et al., supra, 1992). Unlike vaccines produced by synthetic approaches, antigenized antibodies (i) express epitopes with intrinsic tridimensional conformation for immunogenicity at the B cell level (Sollazzo et al., supra, 1990a; Billetta et al., supra, 1991; Lanza et al., supra, 1993; Zaghouani et al., supra, 1995), (ii) target antigen-presenting cells via the Fc receptor, hence maximizing antigen presentation by class II MHC molecules (Zaghouani et al., supra, 1993), and (iii) provide B cells with a continuous source of antigenic peptides for presentation in class I MHC molecules (Billetta et al., supra, 1995). H chain genes under the control of Ig promoter and enhancer elements inoculated into the spleen as plasmid DNA are incorporated into B lymphocytes and initiate immunity against transgene H chain Ig secreted in the serum (see Examples I and II).

The results described herein illustrate the use of STI to induce antigen-specific immunity (see Example III). Immunity against three repeats of the hydrophilic tetrapeptide sequence Asn-Ala-Asn-Pro (NANP), a B-cell epitope expressed on the surface of *Plasmodium falciparum* malaria sporozoites, engineered in the CDR3 of a H chain gene. This amino acid sequence is present in multiple tandem repeats in the central portion of the circumsporozoite (CS) protein (Zavala et al., *Science* 228:1436-1440 (1985)). Antibodies against this epitope develop in people living in endemic areas for malaria (Zavala et al., supra, 1985; Nardin et al., *Science* 206:597-601 (1979)) as well as in volunteers vaccinated with irradiated sporozoites (Clyde et al., *Am. J. Med. Sci.* 266:398-403 (1973); Calle et al., *J. Immunol.* 149:2695-2701 (1992); Egan et al., *Am. J. Trop. Med. Hyg.* 49:166-173 (1993)). This is the only malaria antigen that, when used as a subunit vaccine, has conferred protection against experimental sporozoite challenge in human volunteers (Ballou et al., *Lancet* 1:1277-1281 (1987); Herrington et al., *Nature* 328:257-259 (1987); Edelman et al., *J. Infect. Dis.* 168:1066-1070 (1993)). The results disclosed herein show that STI allows the immune system to be programmed for the production of anti-parasite antibodies and the establishment of immunologic memory against the *P. falciparum* parasite (see Example III).

As disclosed herein in Example III, immunity against the human malaria parasite *Plasmodium falciparum* was induced using somatic transgene immunization, a method to effectively target B lymphocytes in vivo. A single inoculation of plasmid DNA containing an immunoglobulin heavy chain gene coding in the CDR3 for three repeats of, the sequence Asn-Ala-Asn-Pro (NANP), a B-cell epitope of *P. falciparum* sporozoites, induced antibodies against NANP in all mice. Immunologic memory was also established as revealed by booster with an antibody antigenized with the NANP peptide administered in adjuvant or through challenge with *P. falciparum* sporozoites. During the primary response, anti-NANP antibodies were primarily IgM and IgG2a. After booster, all antibody isotypes, including IgG1, developed readily. Thus, immunity to a parasite antigen can be induced by exploiting mechanisms in which B lymphocytes are both the source of the immunogen as well as the effector mechanism of immunity. The results disclosed herein indicate that somatic transgene immunization is an effective approach for vaccination against foreign pathogens.

The methods of the invention can be used to stimulate a T cell response such as a CD4 T cell response and/or a CD8 T cell response. Hypervariable loops of immunoglobulins (Ig) can be used to express discrete peptide sequences of antigens, antigenized antibodies (Zanetti, supra, 1992). These can be the amino acid sequences of epitopes that induce specific responses in T lymphocytes, $CD4^+$ and $CD8^+$.

Encounter with antigen and sufficient co-stimulation transform naive T cells into effector cells, accompanied by clonal expansion and expression of cytokines other than IL-2. Early effector Th cells (Th0 cells) produce both Th1 (IFN-γ) and Th2 (IL-4, IL-5) cytokines. As differentiation progresses through pressure by environmental cytokines and antigen, T cells can be polarized towards the Th1 or Th2 phenotype, but in the absence of such selective pressure remain uncommitted and retain production of all cytokines.

As disclosed herein in Example VIII, cellular immune responses were analyzed in vivo after a single intraspleen inoculation of DNA coding for a 12 residue Th cell determinant associated with a 12 residue B cell epitope, a process termed somatic transgene immunization. As disclosed herein, CD4 T cells are readily activated and produce IL-2, IFN-γ and IL-4, characteristics of an uncommitted phenotype. Although originating in the spleen, T cell responsiveness was found to spread immediately and with similar characteristics to all lymph nodes in the body. A single inoculation was also effective in establishing long term immunologic memory as determined by limiting dilution analysis, with memory T cells displaying a cytokine profile different from primary effector T cells.

These studies provide evidence that by initiating immunity directly in secondary lymphoid organs, one generates an immune response with characteristics that differ from those using vaccines of conventional DNA or protein in adjuvant administered in peripheral sites. Somatic transgene immunization can therefore be used to induce Th cell responsiveness in vivo.

The methods of the invention are also useful for stimulating an antibody response in combination with a T cell response such as a CD4 T cell response. Such a combined response can be termed associative recognition. Inclusion of multiple epitopes from the same antigen or combination of epitopes with different immunogenic function in the same molecule can be used in nucleic acid molecules of the invention. For instance, the antibody response to protein antigens requires the cooperation between B cells and T helper (Th) cells (Mitchison, *Eur. J. Immunol.* 1:18-27 (1971)) with optimal conditions occurring when B and Th cells are specific for different determinants on the same molecule (associative recognition). Based on this principle, synthetic peptide vaccines (Herrington et al., supra, 1987; Tam and Lu, *Proc. Natl. Acad. Sci. USA* 86:9084-9088 (1989); Tam et al., *J. Exp. Med.* 171:299-306 (1990); Munesinghe et al., supra, 1991) or recombinant subunit vaccines (Ballou et al., supra, 1987; Herrington et al. *Vaccine* 10:841-846 (1992)) designed and tested in recent years included both B and Th cell epitopes.

As disclosed herein, an antigenized antibody gene coding for two distinct 12 amino acid long peptides representing a B (Zavala et al., supra, 1985) and a Th (Munesinghe et al., supra, 1991; Nardin et al., *Science* 246:1603-1606 (1989) cell epitope of the circumsporozoite (CS) protein of *P. falciparum* malaria parasite were expressed and tested. Engineering of the CDR3 and the CDR2 of the same $V_H$ domain did not significantly affect secretion in vivo of the antigenized antibody molecules. Mice inoculated into the spleen with this gene mounted an antibody response against the B cell epitope higher than mice receiving the gene coding for the B cell epitope only. In vitro studies established that the two epitope were independently immunogenic in vivo (see Example IV).

Figure 35:
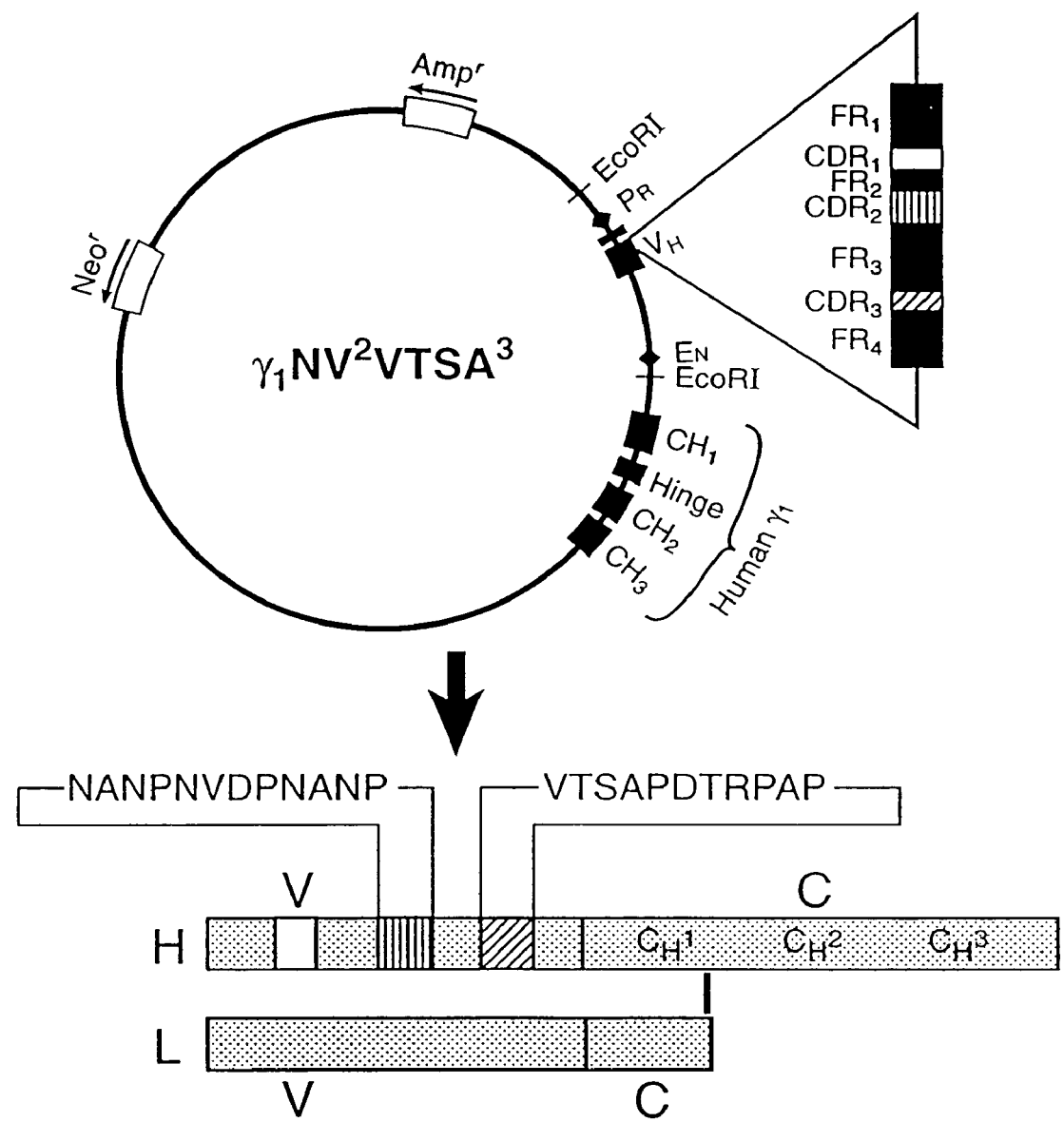

The methods of the invention can similarly by used for associative recognition to stimulate a Th/Th response. While the importance of associative (linked) recognition events in the development of an adaptive immune response are universally accepted, it is not known yet whether or not the same concept applies to a cooperative interaction between Th cell epitopes on the same molecule. Experiments using an antigenized antibody gene in the context of STI revealed that this to be the case (see FIG. 35 and Example X).

Figure 36:
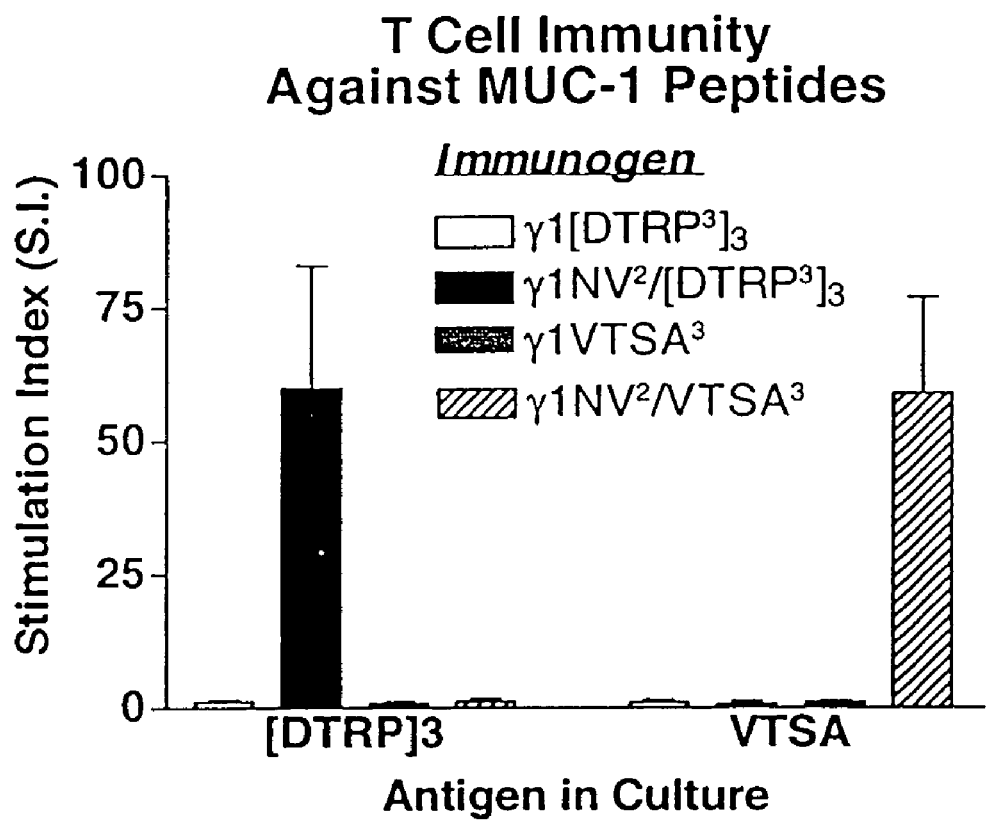

As disclosed herein, two Th cell epitope expressed in the CDR2 and CDR3 of the same gene, respectively, were independently immunogenic in vivo (FIG. 36 and Example X).

The structure of VH domains of Ig has been extensively investigated and it is generally accepted that, while the β-strands of framework regions are conserved and maintain the surface topology between $V_H$ and $V_L$ (Alzari et al., *Ann. Rev. Immunol.* 6:555-580 (1988), CDR loops interconnecting two β-strands vary extensively in amino acid composition (Kabat et al., *Proteins of Immunological Interest*, U.S. Department of Health and Human Services, Bethesda Md. (1987)), hence creating a vast array of binding sites for antigens. Differences exist, however, between the CDR3 and CDR2 with respect to the overall structure of the $V_H$ domain. While CDR3 loops can vary considerably in length (Kabat et al., supra, 1987), CDR2 loops are grouped in few canonical structures (Chothia et al., *Nature* 342:877-883 (1989); Chothia and Lesk, *J. Mol. Biol.* 196:901-917 (1987), possessing key "signature" residues and conserved length to ensure $V_H/V_L$ scaffolding. The results disclosed herein in Example IV stand as an exception to the canonical structure paradigm. As demonstrated, a drastic structural change (both in length and amino acid composition) of the CDR2 loop did not affect folding and pairing of the antigenized VH domain with VL in vivo (see Example IV).

The ability to manipulate Ig V region genes and express multiple heterologous peptides in the CDRs open new possibilities in the design of molecules of complex, predetermined antigen specificity and/or complementary immunogenic function, for example, B/Th, Th/Th or Th/CTL epitopes, depending on the desired effect, for vaccination purposes. The demonstration that the antigenized H chain genes can be easily expressed in vitro and can be used in vivo points to new strategies of vaccination. Because antigenized H chain genes elicit an immune response in vivo, multiple antigen peptides can be used in various combinations to optimize immunogenicity.

The methods of the invention can be used to establish immunological memory. Long-lasting humoral immunity after DNA inoculation has already been documented in few instances (Raz et al., supra, 1994; Davis et al., *Vaccine* 14:910-915 (1996)), although in many reports multiple DNA injections seem to be required (Sedegah et al., supra, 1994; Xiang et al., supra, 1994; Anderson et al., supra, 1996). As disclosed herein, the induction and persistence of specific antibodies was observed at high titers for 18 weeks and at a lower titers for two years (see Example V). These results indicate that specific B cell clonotypes are more easily activated by a prolonged release in the lymphoid microenvironment of minute amounts of the endogenously-synthesized antigen rather than through administration of antigen in adjuvant.

A key feature of STI is the establishment of persistent immunologic memory. Booster injection of the γ1NANP protein in adjuvant 6, 30 or 104 weeks after priming resulted in a bona fide anamnestic response. Specific memory exists when mice are challenged with *P. falciparum* parasites 6 weeks after priming (see Example III). These results indicate that presentation of the NANP epitope through the Ig H chain gene product mimics immunization with the native antigen and that, in turn, NANP-reactive B cells primed via STI are of sufficient affinity to recognize the NANP epitope present in its natural molecular environment at the surface of the parasite.

The observation that a single inoculation of appropriately formulated plasmid DNA establishes persistent immunologic memory is reminiscent of the earlier observation that the immunologic memory that follows a single dose of a suitably potent vaccine increases over time and persists thereafter (Salk, Rev. Infect. Dis., S444-450 (1984)). Similarly, STI triggers, and subsequently maintains, a state of durable immunity and possibly irreversible immunologic memory without the periodic need for reinforcement. Therefore, STI is applicable to those pathogens or conditions which require memory-dependent immunity (Salk and Zanetti, in *Progress in Vaccinology*, Vol. 2, Talwar, ed., Springer-Verlag, New York (1989)).

Specific B cell memory was present long after disappearance of both the transgene product (3-4 weeks) or the transgene itself from the organ of inoculation (~3 months), and was not impeded by circulating antibodies to the transgene product. Conventional views suggested that B cell memory originates from one of two alternative possibilities. One possibility is that the continuous presence of antigen, in this case the transgene product, maintains specific B cells under constant antigen selection and stimulation. The other possibility is that once established, memory B cells hide in lymphoid organs until antigen is re-encountered (Ahmed and Gray, *Science* 272:54-60 (1996)). In the case of STI, immunologic memory appears to be independent of the persistence of the transgene product or even the existence of the transgene in the organ of inoculation. It is possible that, since it is known that follicular dendritic cells play a role as antigen depot (Tew et al., supra, 1980) and this may be relevant to the maintenance of immunologic memory, sufficient amounts of transgene H chain Ig, alone or in the form of complex, could be stored in follicular dendritic cells for a time long enough to provide the stimulus for the maintenance of memory B cells.

Regulation of Ig isotype switch is a complex phenomenon mainly under control of cytokines secreted by $CD4^+$ T cells (TH1 and TH2) activated during presentation of antigen peptides by dendritic cells (DC), B lymphocytes and macrophages. TH1 cells secrete IL-2 and IFN-γ, whereas TH2 cells secrete IL-4, IL-5 and IL-10 (Harriman et al., *Ann. Rev. Immunol.* 11:361-384 (1993)). Although Ig isotype switch is conveniently and clearly regulated in vitro by cytokines (Snapper et al., *J. Immunol.* 140:2121-2127 (1988); Isakson et al., *J. Exp. Med.* 155:734-748 (1982); Coffman et al., J. Immunol. 136:4538-4541 (1986); Snapper et al., *J. Exp. Med.* 167:183-196 (1988)), in vivo regulation using anti-cytokine antibodies is less clear (Finkelman et al., *Int. Immunol.* 3:599-607 (1991)). Reasons for this discrepancy could lie on the fact that, in vivo, CD4$^+$ T cells do not segregate into categories with distinct TH1/TH2 characteristics (Kelso and Gough, *Proc. Natl. Acad. Sci. USA* 85:9189-9193 (1988); Paliard et al., *J. Immunol.* 141:849-855 (1988)). Moreover, isotype switch may be influenced by relative concentrations of cytokines reflecting the avidity of cognate T-B interaction and previous T cell activation (Croft and Swain, *J. Immunol.* 147:3679-3689 (1991)). No previous information has been available concerning the possible influence on isotype switch in vivo by other cell types.

As disclosed herein, the cellular requirements potentially involved in the IgM to IgG1 switch in vivo during priming induced by somatic transgene immunization was investigated (see Example VI).

Inoculation of plasmid DNA in the form of a chimeric gene coding for GM-CSF was able to drive IgG1 class switch readily after priming. Since GM-CSF activates cells of the dendritic lineage, the role of dendritic cells (DC) in regulating the IgM to IgG1 switch was investigated. Bone marrow chimeras were constructed from mice carrying the null mutation for the relB member of the NF-γB/Rel family since these mice lack bone-marrow derived mature DC. RelB (−/−) mice and (−/−) bone marrow chimeras inoculated with DNA/GM-CSF did not produce IgG1 antibodies during the primary immune response. Since relB (−/−) bone-marrow chimeras lack DC of donor origin but possess resident follicular dendritic cells (FDC), these results suggest that Ig class switch in vivo is regulated by the function of interdigitating dendritic cells (IDC). Thus, IDC appears contribute to the qualitative aspects of the emerging immune response.

As disclosed herein in Example VI, isotype switch is likely controlled by T cell-derived cytokines in B cell foci on the edge of T zones of the spleen following the interaction of T cells with B cells and DC. Activation of DC using DNA chimerized with the GM-CSF coding region resulted in a prompt IgM to IgG1 switch, indicating that in vivo, DC are involved in a cellular network which regulates the IgM to IgG1 switch.

The results disclosed herein in Example VI indicate mechanisms of the immune response in vivo. By targeting anatomical structures normally constituting the afferent point of the immune response to foreign pathogens and by injecting DNA of increasing complexity for enhanced immunogenicty and adjuvanticity, it became possible to assign a role to bone marrow derived IDC in controlling the IgM to IgG1 switch (see Example VI). This effect is presumably secondary to other properties of DC such as activation of naive T cells and strengthening the avidity of T-B cell interactions (Steinman, *Annu. Rev. Immunol.* 9:271-296 (1991)). The results disclosed herein indicated that in vivo influence on isotype switch was noted only with respect to IgG1.

Among natural immunologic adjuvants, GM-CSF was shown to increase the potency of immunization against tumor cells and protein antigens. In the course of studies on STI it was realized that GM-CSF affects antibody-mediated memory responses. As disclosed herein in Example VII, GM-CSF given at priming as a DNA/GM-CSF chimeric vaccine enhances the magnitude of the anamnestic response irrespective of the form of antigen used subsequently in the booster immunization. Using mice lacking bone marrow-derived DC, it was also determined that the enhancing effect is not strictly dependent on these cells. These results expand our understanding on the potential utility of GM-CSF in vivo as a modulator of the immune response and immunologic memory induced via STI (see Example VII).

GM-CSF has been used in a variety of systems as immunological adjuvant to increase the potency of immunization. Early reports indicated that tumor cells transfected with GM-CSF induce potent and protective anti-tumor responses (Dranoff et al., supra, 1993; Levitsky et al., supra, 1996). Similarly, an immunoglobulin (Ig) idiotype /GM-CSF chimeric protein was shown to induce higher IgG1 anti-idiotypic response than idiotype alone and to protect against the growth of B lymphoma cells in vivo (Tao and Levy, supra, 1993; Chen et al., *J. Immunol.* 153:4775-4787 (1994)). GM-CSF has also been used to enhance immune responses to DNA vaccination (Xiang and Ertl, supra, 1995). In one instance, mice inoculated with an idiotype/GM-CSF chimeric gene were found to resist growth of B lymphoma cells better than mice vaccinated with the idiotype gene without GM-CSF (Syrengelas et al., supra, 1996).

As disclosed herein, priming with an antigenized antibody /GM-CSF DNA vaccine enhances the magnitude of the anamnestic response against a defined dodecapeptide B cell determinant irrespective of the form of antigen used in the booster immunization (Example VII). Moreover, experiments in mice lacking bone marrow-derived DC indicate that the enhancing effect of GM-CSF is not strictly dependent on these cells. The results disclosed herein define a role for the activity of GM-CSF in vivo as a modulator of the immune response, including immunologic memory.

As disclosed herein in Example VIII, cellular immune responses were analyzed in vivo after a single intraspleen inoculation of DNA coding for a 12 residue Th cell determinant associated with a 12 residue B cell epitope, a process termed somatic transgene immunization. As disclosed herein, CD4 T cells are readily activated and produce IL-2, IFN-γ and IL-4, characteristics of an uncommitted phenotype. Although originating in the spleen, T cell responsiveness was found to spread immediately and with similar characteristics to all lymph nodes in the body. A single inoculation was also effective in establishing long term immunologic memory as determined by limiting dilution analysis, with memory T cells displaying a cytokine profile different from primary effector T cells. These studies provide evidence that by initiating immunity directly in secondary lymphoid organs, one generates an immune response with characteristics that differ from those using vaccines of conventional DNA or protein in adjuvant administered in peripheral sites.

The methods of the invention can be used to administer a nucleic acid molecule encoding one or more heterologous epitopes to a lymphoid tissue. Administration to a lymphoid tissue provides targeting of the nucleic acid molecule to a lymphoid cell. Therefore, the methods of the invention can also be used to administer a nucleic acid molecule to a lymphoid cell. Administration of a nucleic acid molecule to a lymphoid cell allows the protein expression capabilities of the lymphoid cell to be used to express the epitope against which the stimulation of an immune response is desired.

A nucleic acid molecule of the invention can be targeted to a lymphoid cell. The lymphoid cell can be targeted in vivo or ex vivo. For example, as described above, a nucleic acid molecule can be administered to an individual in vivo to target a lymphoid cell. For example, the nucleic acid molecule can be administered to a lymphoid tissue, resulting in targeting of hematopoietic cells, including a lymphoid cell, in the lymphoid tissue. However, it is understood that a nucleic acid molecule of the invention can be administered by any method or route that results in targeting of a hematopoietic cell such as a lymphoid cell for expression of the epitope encoded by the nucleic acid molecule.

A nucleic acid molecule of the invention can also be administered ex vivo. For example, hematopoietic cells, including lymphoid cells, can be obtained from an individual or from an immunologically compatible individual, and a nucleic acid molecule of the invention can be administered to these cells ex vivo. Methods of administering nucleic acid molecules to cells ex vivo are well known in the art and include, for example, calcium phosphate precipitation and electroporation (see, for example, Sambrook et al., *Molecular Cloning a Laboratory Manual* Cold Spring Harbor Press (1989); Ausubel et al., *Current Protocol in Molecular Biology*, Wiley & Sons (1998)) These lymphoid cells, which now contain the nucleic acid molecule and express the encoded epitopes, can then be administered to an individual. The lymphoid cells expressing the epitopes can then stimulate an immune response.

Methods of introducing a gene of interest into a whole organism are well known in the art (see, for example, Kay et al., *Proc. Natl. Acad. Sci. USA*, 89:89-93 (1993); Chowdbury et al., *Science*, 254:1802-1805 (1991); Grossman et al., *Nature Genetics*, 6:335-341 (1994); Malech et al., *Proc. Natl. Acad. Sci. USA*, 94:12133-12138 (1997)).

The invention additionally provides methods of treating a condition by administering a nucleic acid molecule of the invention, where the nucleic acid molecule is targeted to a hematopoietic cell. The administration of a nucleic acid molecule expressing an epitope to stimulate an immune response is useful for treating a condition as described above. The methods of the invention for treating a condition by targeting a hematopoietic cell are useful when a B cell, T cell or dendritic cell. The methods of the invention for treating a condition are particularly useful when a B cell is targeted.

The invention further provides methods of treating a condition by administering a nucleic acid molecule comprising a hematopoietic cell expression element operationally linked to a nucleic acid molecule encoding one or more heterologous polypeptides, where the nucleic acid molecule is targeted to a hematopoietic cell. The targeted hematopoietic cells serve to express a heterologous polypeptide to treat a condition. The methods of the invention are advantageous for administering a therapeutic polypeptide to treat a condition. The methods of the invention can be used, for example, to express a hormone, cytokine, clotting factor or immunoglobulin. For example, if an individual has a condition for which an increase in expression of a hormone or cytokine would be beneficial, such an individual can be treated by administration of a nucleic acid molecule expressing a hormone or cyotokine polypeptide. For example, an individual having a condition characterized by immunodeficiency can be treated by administering a cytokine such as IL-2 or INF-γ, or other cytokine, as disclosed herein, or by administering an immunoglobulin. Similarly, an individual suffering from a condition such as hemophelia can be treated, for example, by administering a nucleic acid molecule encoding a clotting factor such as factor VIII or factor IX. One skilled in the art can readily determine an appropriate polypeptide to express for treating a given condition.

The methods of the invention can be used to treat a condition by expressing a wide variety of disease-associated gene products of interest, which can be employed to treat or prevent the disease of interest. For example, and by way of illustration only, the genes can encode enzymes, hormones, cytokines, antigens, antibodies, clotting factors, anti-sense RNA, regulatory proteins, ribozymes, fusion proteins and the like. The methods can thus be used to supply a therapeutic protein such as Factor VIII, Factor IX, Factor VII, erythropoietin (U.S. Pat. No. 4,703,008), alpha-1-antitrypsin, calcitonin, growth hormone, insulin, low density lipoprotein, apolipoprotein E, IL-2 receptor and its antagonists, superoxide dismutase, immune response modifiers, parathyroid hormone, the interferons (IFN alpha, beta or gamma), nerve growth factors, glucocerebrosidase, colony stimulating factor, interleukins (IL) 1 to 15, granulocyte colony stimulating factor (G-CSF), granulocyte, macrophage-colony stimulating factor (GM-CSF), macrophage-colony stimulating factor (M-CFS), fibroblast growth factor (FGF), platelet-derived growth factor (PDGF), adenosine deaminase, insulin-like growth factors (IGF-1 and IGF-2), megakaryocyte promoting ligand (MPL, or thrombopoietin). The therapeutic polypeptides can be useful, for example, for the treatment and prevention of genetic disorders such as coagulation factor disorders, glycogen storage disease, and alpha-1-antitrypsin deficiency. The methods of the invention can also be used to express ligands of adhesion molecules such as integrins, for example, to block adhesion function such as angiogenesis.

The invention also relates to pharmaceutical compositions comprising a pharmaceutically acceptable carrier and a nucleic acid molecule of the invention. The methods of the invention can therefore utilize pharmaceutical composition comprising a nucleic acid molecule of the invention encoding an epitope. Pharmaceutically acceptable carriers are well known in the art and include aqueous or non-aqueous solutions, suspensions and emulsions, including physiologically buffered saline, alcohol/aqueous solutions or other solvents or vehicles such as glycols, glycerol, oils such as olive oil or injectable organic esters.

A pharmaceutically acceptable carrier can contain physiologically acceptable compounds that act, for example, to stabilize the nucleic acid molecules to be administered or increase the absorption of the nucleic acid molecules. Such physiologically acceptable compounds include, for example, carbohydrates, such as glucose, sucrose or dextrans, antioxidants such as ascorbic acid or glutathione, chelating agents, low molecular weight polypeptides, antimicrobial agents, inert gases or other stabilizers or excipients. Nucleic acid molecules can additionally be complexed with other components such as peptides, polypeptides and carbohydrates. Nucleic acid molecules can also be complexed to particles or beads that can be administered to an individual, for example, using a vaccine gun. One skilled in the art would know that the choice of a pharmaceutically acceptable carrier, including a physiologically acceptable compound, depends, for example, on the route of administration of the expression vector. As described above, the route of administration will generally be direct injection into a secondary lymphoid tissue.

The following examples are intended to illustrate but not limit the present invention.

EXAMPLE I

Somatic Transgene Immunization with DNA Encoding an Immunoglobulin Heavy Chain

This example describes immunization with plasmid DNA by direct injection into the spleen.

The methods for preparation of plasmid DNA and immunization by injection into the spleen are described below (Gerloni et al., *DNA Cell Biol.* 16:611-625 (1997)).

Eight to ten week old C57BL/6 (H-2$^b$) mice were purchased from the Jackson Laboratories (Bar Harbor, Me.) or Harlan Sprague-Dawley (San Diego, Calif.). Mice were maintained in the animal facility of the University of California, San Diego, throughout the duration of the experiments.

Four plasmid vectors utilized for in vivo inoculation. γ1WT defines plasmid pNeogγ$_1$62 (Sollazzo et al., *Eur. J. Immunol.* 19:453-457 (1989)) which contains the 2.3 Kb EcoRI DNA fragment carrying the genomic murine V$_H^{62}$ rearrangement at the unique EcoRI site of the pNγ1 vector (Morrison et al., *Proc. Natl. Acad. Sci. USA* 81:6851-6855 (1984)). γ1WT encodes a genomic human γ1 gene and contains a neomycin resistance gene under the control of the SV40 promoter for the selection of stable transformant cells. γ1WT-TAC is a modified version of the γ1WT plasmid in which the three base pairs of TAC were introduced by oligonucleotide-directed mutagenesis in the CDR3 as a genetic marker. This was used uniquely to study gene integration. γ1NANP is a modified version of the γ1WT plasmid where the third hypervariable region was modified to encode three repeats of the tetrapeptide Asn-Ala-Asn-Pro (NANP) sequence (et al., *Prot. Engng.* 4:215-220 (1990a)). This plasmid was used for mRNA analysis of the V$_H$ region. pSV2Neo is the original plasmid forming the backbone of the pNeoγ1 vector without the human γ1 C region gene (Mulligan and Berg, *Proc. Natl. Acad. Sci. USA* 78:2072-2076 (1981)). This plasmid was used as a control in the immunization experiments. These three plasmids are illustrated in FIG. 1. γ2bV$_H^{36-65}$ defines a plasmid containing the V$_H^{36-65}$ gene (Sharon et al., *J. Immunol.* 142:596-601 (1989)) joined to a murine γ2b C region gene. All plasmid DNAs were prepared from DH5γ *Escherichia coli* according to standard procedures (Sambrook et al., *Molecular Cloning. A Laboratory Manual.*, 2nd ed., Cold Spring Harbor Laboratory Press (1989)). The purity of the DNA was monitored using the following equation: % N=(11.1R−6.32)/(2.16−R) where R=260 nm/280 nm, % N=% of Nucleic Acid (Glasel, *BioTechniques* 18:62-63 (1995)).

Engineered antibodies γ1WT, γ2bWT and γ2bV$_H^{36-65}$ were prepared by electroporation (Billetta and Zanetti, *ImmunoMethods* 1:41-51 (1992) of the γ1WT, γ2bWT (Sollazzo et al., supra, 1989) and γ2bV$_H^{36-65}$ (Sharon et al., supra, 1989) plasmid DNAs into the murine J558L cell line, an H chain-defective variant of the J558 myeloma cell (Morrison, *Science* 229:1202-1207 (1985)). Transfectant cells were screened for immunoglobulin production by ELISA and the immunoglobulins were purified by affinity chromatography on a Protein A column (Billetta and Zanetti, supra, 1992).

Mice were inoculated with 100 µg of plasmid DNA per inoculation. All DNA inoculations were done in the absence of immunological adjuvants. Four basic routes of inoculation were used. a) Intramuscular. The plasmid DNA was injected in the quadriceps in 30 µl volume in sterile saline. Thereafter, mice received three booster injections at weekly intervals for a total of four injections. b) Subcutaneous. The plasmid DNA was injected in the back in 25-50 µl volume of sterile saline. Thereafter, mice received three booster injections at weekly intervals for a total of four injections. c) Intravenous. The plasmid DNA was injected in 50-100 µl volume of sterile saline solution via the tail vein. Thereafter, mice received three booster injections at weekly intervals for a total of four injections. d) Intraspleen. The plasmid DNA was injected in 30 µl volume of sterile saline solution. For the intraspleen inoculation mice were anesthetized with a cocktail of Ketamine, Xylazine and Acepromazine. Anesthetized mice were shaved locally and a small incision (3-4 mm) was made with a scalpel in the upper left portion of the abdomen under the diaphragmatic line. By pulling gently the fat of the ventral part of the spleen the organ was exposed through the small incision and injected with DNA using a 28 gauge needle. The abdomen was immediately sutured using 4-0 sterile, non-absorbable surgical suture thread. Mice inoculated via this route were injected only once. In one experiment (Table 1) mice received three booster injections of 100 γg of DNA intravenously. Mice were bled via the retro-orbital route on day 0 and subsequently at 7 days intervals.

Mice were immunized with affinity-purified γ1WT protein adsorbed on alum (50 µg per mouse) intraperitoneally. Mice that were boosted with the γ1WT protein received 50 µg of the protein emulsified in incomplete Freunds' adjuvant subcutaneously.

The detection of antibodies to γ1WT, γ2bWT and γ2bV$_H^{36-65}$ proteins was performed by direct ELISA on 96-well polyvinyl microtiter plates (Dynatech; Gentilly Va.) coated (2.5 µg/ml) by drying at 37° C. After coating wells were blocked with 1% bovine serum albumin (BSA) in phosphate buffered saline (PBS), pH 7.3. Wells were incubated overnight at 4° C. with mice sera diluted in 1% BSA-PBS, containing 0.05% Tween-20 (PBSA). The bound antibodies were revealed using a goat antibody to mouse γ-globulins absorbed with human γ-globulins and conjugated with horseradish peroxidase (HP) (Pierce; St. Louis Mo.). The bound peroxidase was revealed by adding o-phenylenediamine dihydrochloride and H$_2$O$_2$. Plates were read after 30 minutes in a micro-plate reader (Vmax, Molecular Devices) at 492 nm. Tests were done in duplicate.

The presence of γ1WT H chain transgene polypeptide in the serum of mice was detected by ELISA capture assay (Billetta and Zanetti, supra, 1992). Briefly, 1:10 dilution of individual mouse sera in PBSA were incubated on 96-well plate coated with a goat antibody to human γ-globulin (10 µg/ml). To determine the concentration of the immunoglobulin H chain transgene product in the serum O.D. values were plotted against a standard curve constructed with known amount of human γ-globulins diluted in PBSA containing 10% normal mouse serum. The bound antibodies were revealed using a HP-conjugated goat antibody to human γ-globulins (H chain specific) absorbed with murine immunoglobulins (Sigma; St. Louis Mo.). The bound peroxidase activity was revealed by adding o-phenylenediamine dihydrochloride and H$_2$O$_2$. The test was continued as detailed above.

The kinetics of synthesis of the transgenic mRNA was studied by reverse RT-PCR in the spleen of mice inoculated via the intrasplenic route. Briefly, spleens were harvested 3, 10, 20, 127 days after the initial inoculation, frozen at −170° C., and the cells were prepared by gentle teasing. Typically, PolyA$^+$ mRNA was isolated from 11 mg of spleen tissue using the Micro-FastTrack mRNA isolation kit (Invitrogen; San Diego Calif.). cDNA was synthesized by reverse transcription using the cDNA Cycle Kit (Invitrogen, San Diego). Specific PCR primers for the murine V$_H$, TTCGATGTCCAT-ACCATGAGAGTA and TTCAGCACCTACTATCCAGA-CACT and the human γ1 C region genes TTCCTCTTCT-GCGTGTAGTGGTTG and TTCATAATGCCAAGACAAAGCCGC were designed using Oligo 4.0 Primer Analysis Software (NBI, Inc.; Plymouth Minn.) from the sequences of the murine V$_H^{62}$ and human γ1 C region genes obtained from the National Center for Biotechnology Information (NCBI) GenBank (Bethesda Md.). Primers for the β-actin gene (FIG. 4) were used to control for the extraction and reverse transcription of spleen mRNA. The PCR reaction with Taq polymerase (Gibco BRL; Gaithersburg, Md.) was performed according to the following conditions: 1 min at 92 γC followed by 2 min at 40° C. and 3 min at 72° C. This cycle was repeated 30 times. cDNA amplification and size determination ($V_H^{62}$=198 bp; human γ1 C region gene=466 bp) were checked by electrophoresis using 4% NuSieve 3:1 agarose gel (FMC; Rockland Me.).

All DNAs analyzed by Southern blot were separated by electrophoresis on a 1% agarose gel and transferred to Hybond-N nylon membrane (Amersham; Cleveland, Ohio). Blots were hybridized with oligonucleotide probes labeled using T4 polynucleotide kinase forward reaction in presence of ($\gamma$-$^{32}$P ATP).

For extraction of genomic DNA from spleen tissue and genomic DNA sequencing, spleens were harvested 17 days after DNA inoculation, frozen at −170° C. and the cells were prepared by tissue grinding in liquid nitrogen. Typically the genomic DNA was extracted from 10 mg of spleen tissue using the QIAamp Tissue Kit (Qiagen Inc.; Chatsworth Calif.). Two specific primers, TTATTGAGAATAGAGGA-CATCTG and ATGCTCAGAAAACTCCATAAC for the murine $V_H^{62}$ were used to amplify by PCR a segment of 520 bp from genomic DNA. The PCR conditions were as follows: 45 sec at 94° C., 45 sec at 54° C. and 45 sec at 72° C. for 30 times. The PCR products were cloned in pGEM-T vector (Promega; Madison Wis.). Six clones from the genomic DNA of the spleen inoculated 17 days earlier and four clones from the genomic DNA of tranfectoma B cells (Sollazzo et al., supra, 1989) were sequenced on both strands by dideoxy termination method with Sequenase 2.0 DNA sequencing kit (USB; Cleveland Ohio) using two primers, AACAGTAT-TCTTTCTTTGCAGG and TTATTGAGAATAGAGGA-CATCTG, annealing 10 bp before the first codon of the FR1 and at the 3' end of the FR4, respectively.

The DNA of a chimeric immunoglobulin H chain gene consisting of a murine rearranged $V_H$ region joined with a genomic human γ1 C region was inoculated into the spleen of mice. This gene is under the control of tissue-specific regulatory elements (promoter and enhancer). The configuration of the plasmid DNA γ1WT containing the H chain gene is shown in FIG. 1. Mice were inoculated via the intrasplenic route once. A first pilot experiment compared the intraspleen route with other routes of inoculation, for example, intramuscular, subcutaneous, and intravenous, to verify the correctness of the hypothesis and to control for tissue-specificity. Table 1 shows the anti-immunoglobulin response determined by an ELISA method in mice inoculated through the various routes with the number of injections in each case. A marked antibody response was seen only in mice inoculated once via the intrasplenic route (group I). Mice inoculated once via the intrasplenic route and boosted intravenously three times (group V) also responded but because the three additional intravenous injections yielded a substantially similar antibody titer, a logical conclusion is that the antibody response seen in group V reflects mainly the effect of intraspleen inoculation. The subcutaneous route yielded a weak response in two mice only (group III). No antibody response was detected in mice inoculated four times intramuscularly or intravenously (groups II and IV). Thus, the use of an immunoglobulin H chain gene under the control of tissue specific regulatory elements yielded immunity only after intraspleen inoculation.

TABLE 1

Production of Antibodies Reacting with the γ1WT Protein in C57B1/6 Mice Inoculated with γ1WT DNA: Effect of the Route of Inoculation

| Group | Route of Inoculation | Injections (no.) | Mice (no.) | Responders (no.) | Antibody titer[a] (log) |
|---|---|---|---|---|---|
| I | i.s. | 1 | 4 | 4/4 | 3.1 ± 0.4 |
| II | i.m. | 4 | 4 | 0/4 | ≦2.3[b] |
| III | s.c | 4 | 4 | 2/4 | 2.6 |
| IV | i.v | 4 | 4 | 0/4 | ≦2.3 |
| V | i.s + i.v. | 1 + 3 | 4 | 4/4 | 3.2 ± 0.3 |

[a]Values of antibody titer were measured and calculated on sera collected 21 days after the first inoculation.
[b]The preinoculation value of a large pool of mice was 2.3(log). The end-point positive serum dilution on which the titer was calculated was an OD value ($A_{492}$) ≧0.200.

Figure 2:
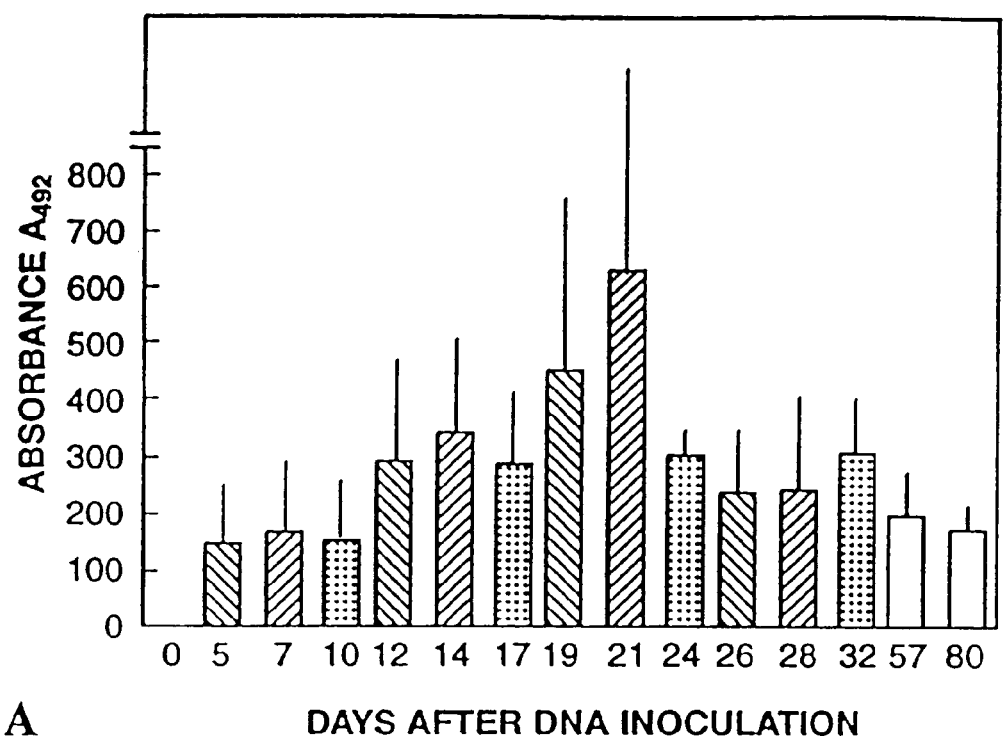
FIG. 2 shows a kinetic analysis of the anti-immunoglobulin response and immunoglobulin heavy (H)-chain transgene immunoglobulin production in mice inoculated intraspleen with plasmid DNA γ1WT. Panel A shows antibody response. Each column corresponds to a group of six individual C57Bl/6 mice. All mice were inoculated at the same time. They were bled at refracted time intervals to separate two consecutive bleedings on the same animal in compliance with regulations for humane animal care. Therefore, an identical pattern identifies the same group of mice. The columns referring to day 57 and 80 are the mean value of mice from all three groups (18 mice). Values represent means±SD of absorbances±($A_{492}$) obtained by ELISA. Tests were done in duplicate at 1:1, 600 dilution. Panel B shows the production of transgenic immunoglobulin. Each symbol corresponds to individual determinations (single mouse) at the time indicated on the abscissa. Groups of individual C57Bl/6 mice were inoculated at the same time. Mice were bled at refracted time intervals to separate two consecutive bleedings on the same animal in compliance with regulations for humane animal care. Values represent the absorbance ($A_{492}$) obtained by a capture ELISA as detailed in the Material and Experimental Procedures. Symbols define single mice from the same group of mice. Tests were done on sera diluted 1:10.
Figure 2:
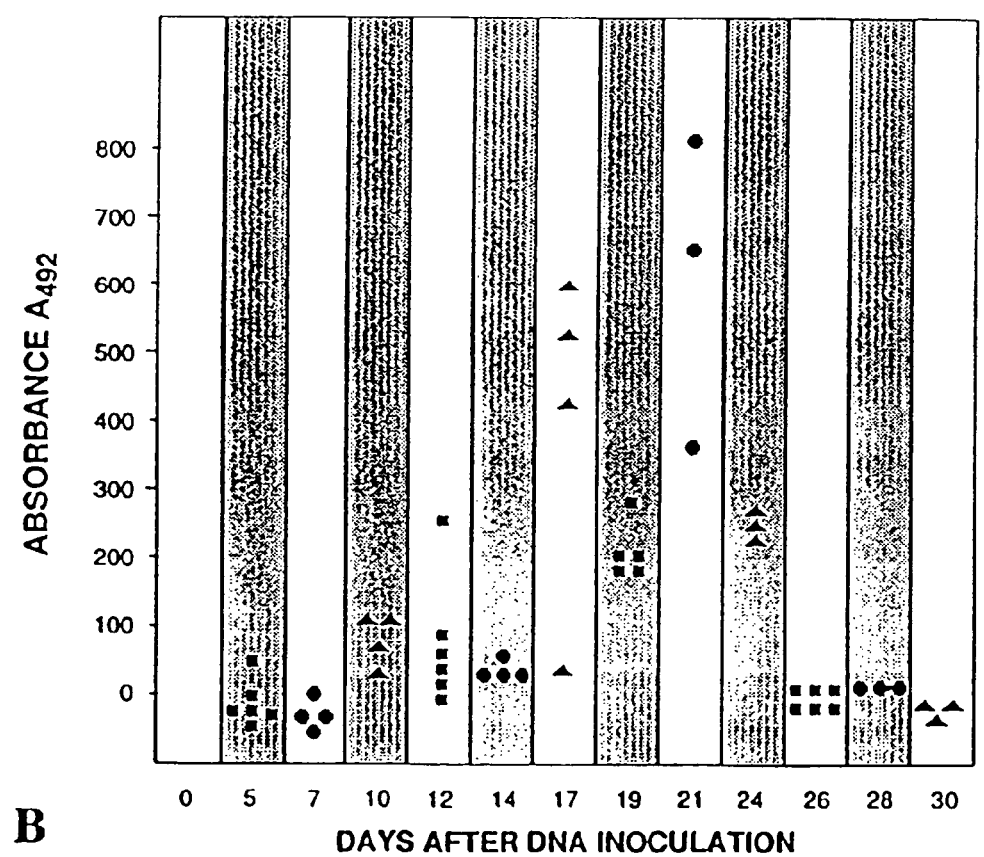
Figure 3:
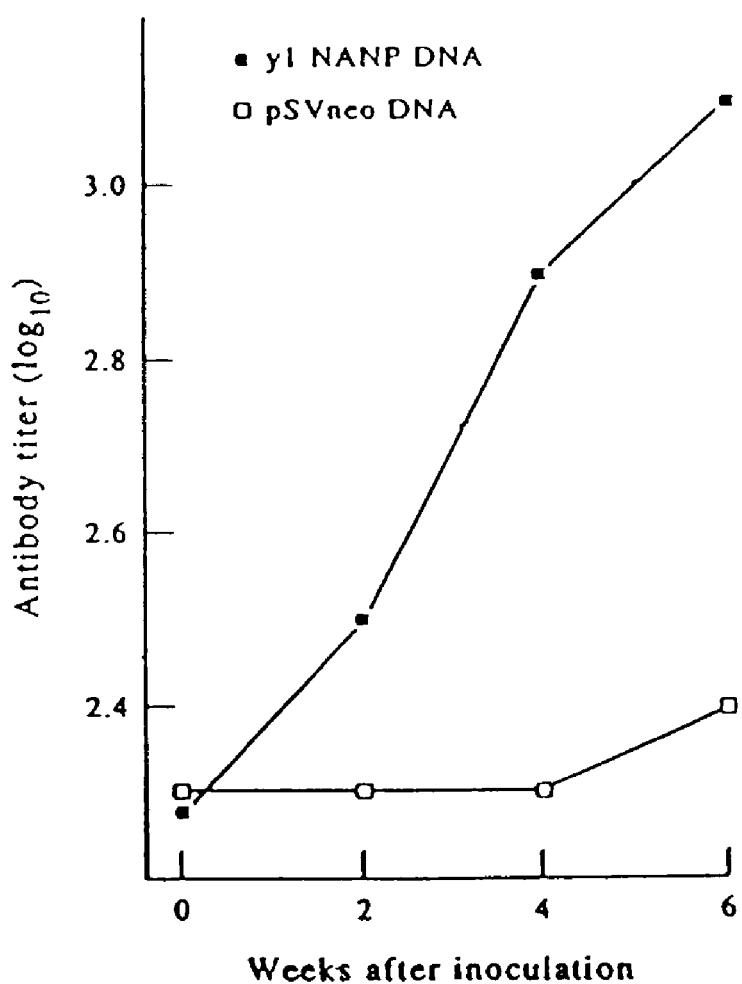
FIG. 3 shows the effect of different routes of inoculation on the primary antibody response against the γ1NANP immunoglobulin following plasmid DNA injection. Each group is composed of four mice. Antibody titers ($Log_{10}$) were determined by ELISA. Data shown represent the mean of individual titers which were determined on the basis of the last value with an absorbance ≧ of 0.200 ($A_{492}$).

The kinetics of the antibody response was determined. In repeated experiments, intraspleen inoculation is reproducibly effective in initiating the immune response. The mean average antibody (log) titer ranged from 3.2 to 4.4, depending on the experiment (Table 2). The anti-immunoglobulin response was not merely due to a non-specific, polyclonal activation since mice injected with plasmid pSV2Neo, which lacks the immunoglobulin coding region of plasmid DNA γ1WT, failed to mount any detectable antibody response (Table 2). The time course of the anti-immunoglobulin response was further analyzed. Antibodies were detectable as early as day 5 with a peak on day 21 (FIG. 2A). Thereafter, the antibody response dropped progressively but did not disappear. Circulating antibodies were still detectable 200 days after a single DNA inoculation.

TABLE 2

Production of Antibodies Reacting with the γ1WT Protein in the Serum of C57B1/6 Mice After a Single Intraspleen Inoculation of DNA

| Experiment number | Material inoculated | Mice (no.) | Responders (no.) | Antibody titer (log)[a] Mean ± SD | Range |
|---|---|---|---|---|---|
| 1 | γ1WT | 14 | 14/14 | 3.6 ± 0.2[b] | 3.2-3.8 |
| 2 | γ1WT | 7 | 7/7 | 3.6 ± 0.2 | 3.2-3.8 |
| 3 | γ1WT | 9 | 9/9 | 4.1 ± 0.2 | 3.8-4.4 |
| 4 | pSB2neo | 7 | 0/7 | ≦2.3 | — |
| 5 | Saline | 3 | 0/3 | ≦2.3 | — |

[a]Values of antibody titers were measured and calculated on sera collected 21 days after the first inoculation.
[b]The preinoculation value of each mouse was ~2.3(log). The end-point positive serum dilution on which the titer was calculated was an OD value (A492) ≧0.200. Sera were tested in duplicate. The experiments and the ELISA were done independently and at different times.

The kinetics of transgene H chain immunoglobulin production were determined. Using an ELISA capture assay specific for the human γ1 C region we detected the H chain transgene product in the serum of all mice inoculated with plasmid DNA γ1WT (Table 3). Mice injected with control plasmid pSV2Neo were consistently negative. Using a titration curve constructed with known amounts of human γ-globulins we estimated that at their highest detection value the concentration of the transgene product ranged between 7.3 and 32.1 ng/ml (minimal and maximal means of independent experiments) (Table 3). Values in individual mice varied between 1 and 72 ng/ml. A kinetic survey showed that the transgene H chain immunoglobulin product became detectable starting from day 10 (FIG. 2b). Over numerous detections and several experiments we found that maximal detection, which varied from animal to animal, ranged between day 17 and 21. The H chain transgene product could not be detected beyond day 26 possibly due to the formation of immune complexes with anti-immunoglobulin antibodies. Thus, inoculation of an immunoglobulin H chain DNA via the intrasplenic route yielded a measurable secretion of the transgene immunoglobulin product in 100 percent of cases until the day 26.

TABLE 3

Detection of the Transgene Immunoglobulin Product in the Serum of C57B1/6 Mice After a Single Intraspleen Inoculation of DNA

| Experiment number | Material inoculated | Mice (no.) | Producers (no.) | Production (ng/ml) Mean ±± SD | Range |
|---|---|---|---|---|---|
| 1 | γ1WT | 14 | 14/14 | 7.3 ± 7.6$^a$ | 1.0-21.1 |
| 2 | γ1WT | 7 | 7/7 | 32.1 ± 22.7 | 10.3-72 |
| 3 | γ1WT | 9 | 9/9 | 9.3 ± 5.1 | 5.1-15 |
| 4 | pSV2neo | 7 | 0/7 | — | — |
| 5 | Saline | 3 | 0/3 | — | — |

Values of transgene product in the serum represented correspond to the day of maximal detection for each individual mouse. Determination of circulating transgene immunoglobulins was done as detailed in Materials and Methods. The experiments and the ELISA were done independently and at different times.

The synthesis of transgene mRNA in the spleen of immunized mice was determined. In vivo transcription of the transgene was studied in spleen tissues of mice at various times after inoculation with plasmid DNA γ1WT. The poly A($^+$) mRNA was prepared and reverse-transcribed, and the cDNA was amplified by polymerase chain reaction (PCR). Because the γ1WT gene is a chimeric gene, we used primers specific for the human γ1 C and the murine $V_H$ regions, respectively. A 466 bp DNA segment from the human γ1 C region and a 198 bp DNA segment from the murine $V_H$ region were amplified independently (FIG. 4A) mRNA was detected starting from day 3 until day 127. Whereas amplification of the human γ1 C region in a naive mouse was negative, not surprisingly the murine $V_H$ was readily amplified as WT $V_H^{62}$ (FIG. 1) is a seemingly germline gene of the $V_H^{7183}$ gene family (FIG. 4A) (Sollazzo et al., supra, 1989). To verify the specificity, a Southern blot was performed on the DNA. As shown in FIG. 4B, the amplified human γ1 C segment co-migrated with the segment amplified from the pNeoγ1 plasmid used as a positive control. To specifically probe for the $V_H$ region, an experiment was performed in which the DNA used for inoculation was modified in the CDR3 to contain the coding sequence for three repeats of the tetrapeptide Asn-Ala-Asn-Pro (γ1NANP) as a nucleotide marker (Sollazzo et al., supra, 1990a) (FIG. 1). The 240 bp DNA fragment amplified from cDNA gave a strong and specific hybridization band using a probe specific for the modified CDR3 segment (FIG. 4C). No hybridization was observed in the amplified product from an unmanipulated spleen (FIG. 4C). Taken together, these results demonstrate that following a single intraspleen inoculation, the H chain transgene is taken up by spleen lymphocytes and transcribed.

Figure 5:
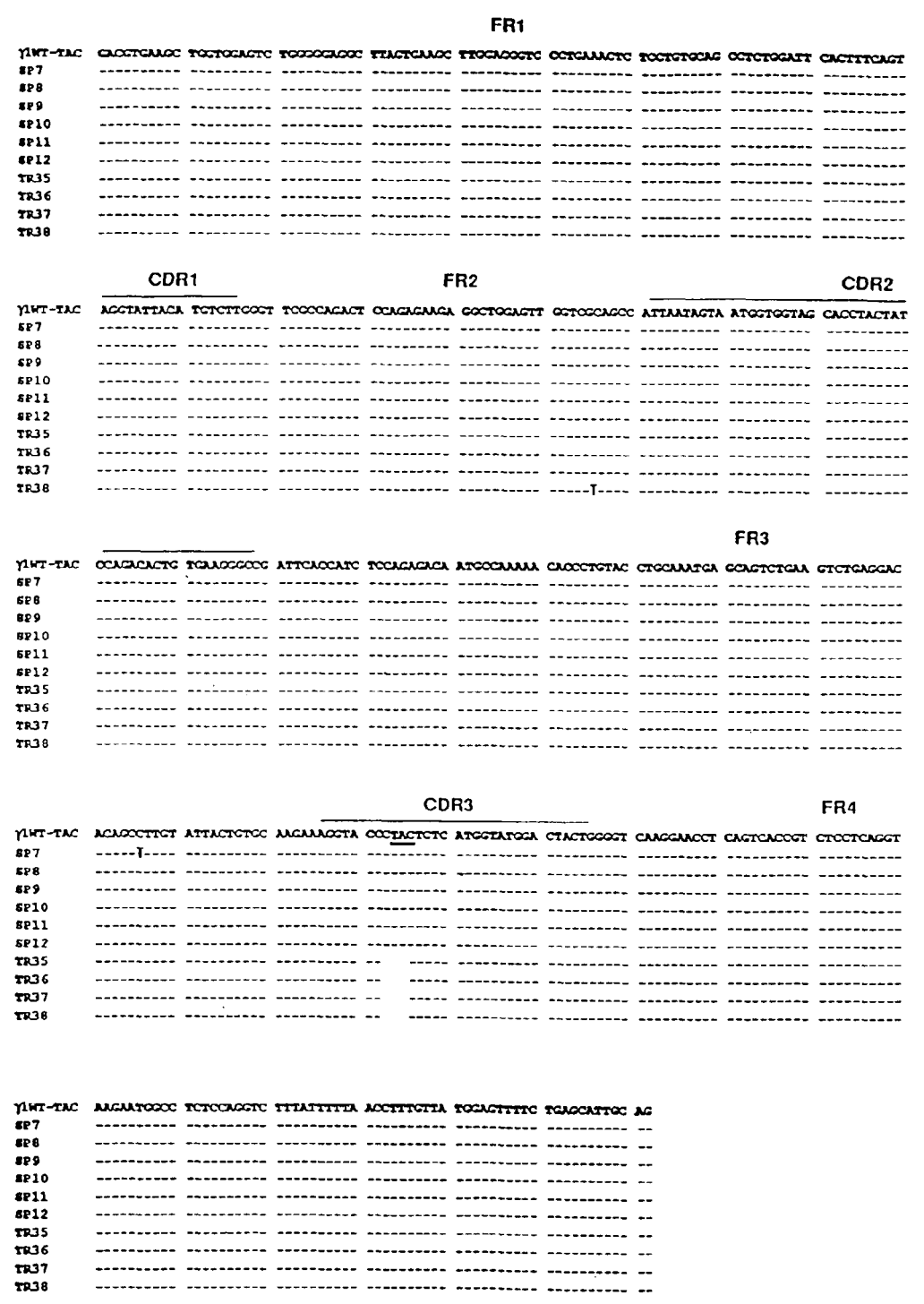

Somatic mutations were determined. DNA sequencing was used to determine whether persistence in vivo in the host cell DNA would cause the transgene to undergo somatic mutation. Because somatic mutation is property of the VDJ coding region (Griffiths et al., Nature 312:271-275 (1984)), this region only was characterized. The VDJ coding region (520 bp) was amplified from genomic DNA using specific primers as described above. Altogether, sequencing was done in six clones from genomic DNA of an inoculated spleen and four clones from genomic DNA of transfectoma B cells which served as reference. The nucleotide sequence of the six clones showed no mutation with the exception of a single conservative (C to T) mutation in framework 3 in clone SP7. A single (C to T) mutation was also observed in framework 2 in clone TR38 from transfectoma B cells DNA (FIG. 5). Thus, the VDJ coding region of the transgene retrieved in an integrated form 17 days after intraspleen inoculation did not show evidence of hypermutation. Thus, a lack of somatic mutation in the transgene in vivo was observed.

Figure 6:
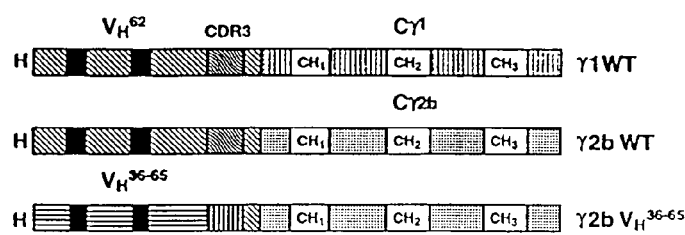
FIG. 6 shows anti-immunoglobulin antibodies produced by C57Bl/6 mice inoculated intraspleen with plasmid DNA γ1WT react with the V region. Panel A shows representation of the engineered antibodies used to study the ELISA reactivity. $V_H^{62}$ and $V_H^{36-65}$ are two unrelated murine $V_H$ region gene products. γ1 and γ2b refer to human IgG1 and murine IgG2b C region, respectively. Panel B shows ELISA reactivity. Values represent the means of a group of four mice. The antigen used was as follows: γ1WT (black square); γ2bWT (open square); and γ2b$V_H^{36-65}$ (black circle). Tests were done in duplicate on sera used at 1:800 dilution.
Figure 6:
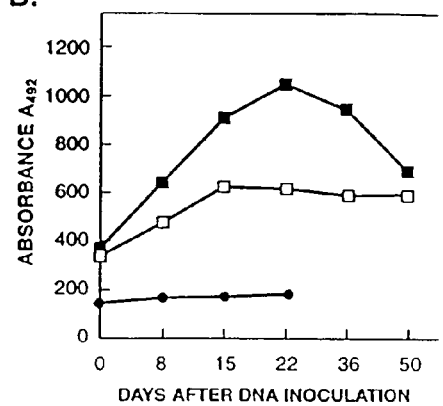

Anti-immunoglobulin antibodies were found to react with the V region of the H chain transgene. Polyclonal anti-immunoglobulin responses are predominantly directed against antigenic determinants of the C region. However, antibodies to V region determinants, for example, idiotypes and allotypes, are also usually produced. To determine whether the antibody response following inoculation of plasmid DNA γ1WT was also directed at V region determinants of the H chain transgene product, the sera of four tested mice for binding to a panel of engineered antibodies to delineate specific reactivities. FIG. 6A illustrates the composition of the H chain of the three immunoglobulin molecules used in the mapping experiment. γ1WT is the prototype immunoglobulin encoded by the γ1WT plasmid, as described in FIG. 1; γ2bWT is an antibody possessing the WT $V_H$ region joined to a murine γ2b C region; and γ2b$V_H^{36-65}$ is an antibody possessing the murine $V_H^{35-65}$ region joined to a murine γ2b C region. In all three instances, the L chain was γ1. Serum anti-immunoglobulin antibodies from immunized mice bound in ELISA γ1WT and γ2bWT but not γ2b$V_H^{36-65}$ (FIG. 6B), suggesting that, following somatic transgene immunization, mice also produced antibodies against the V region of the H chain transgene product.

These results demonstrate that a nucleic acid molecule can be administered to a lymphoid tissue, the spleen, to elicit an immune response.

EXAMPLE II

In Vivo Role of B Lymphocytes in Somatic Transgene Immunization

This example describes the role of B lymphocytes in somatic transgene immunization.

The preparation of plasmids and immunization are described below (Xiong et al., Proc. Natl. Acad. Sci. USA 94:6352-6357 (1997)).

Plasmid γ1NANP (Sollazzo et al., supra, 1990a) carries a chimeric H chain gene in which a productively rearranged murine V region gene is joined to a human γ1 C region gene. The V region of this H chain gene was modified in the third complementarity determining region (CDR3) by introduction of the nucleotide sequence coding for three Asn-Ala-Asn-Pro repeats (Sollazzo et al., supra, 1990a). The promoter and enhancer elements in this plasmid are those constitutively existing in Ig H chain genes and have been described previously (Sollazzo et al., supra, 1989). Plasmid pSVneo is the original plasmid vector that lacks the murine V region and the human γ1 C region genes (Mulligan and Berg, supra, 1981).

The plasmid DNA was prepared from transformed DH5γ Escherichia coli according to Example I. For DNA inoculation, eight to ten week old C57BL/6 (H-2b) female mice (Jackson Laboratories; Bar Harbor Me.) were inoculated with plasmid DNA (100 γg in 30 γ1 of sterile saline solution) directly into the spleen (see Example I).

Antibodies to γ1NANP were detected on 96-well polyvinyl microtiter plates coated with affinity-purified antibody γ1NANP (2.5 μg/ml). Sera were diluted in PBSA. The bound antibodies were revealed using a HP-conjugated goat antibody to mouse γ-globulins absorbed with human γ-globulins (Pierce; St. Louis Mo.). The bound peroxidase was revealed by adding o-phenylenediamine dihydrochloride and $H_2O_2$. Tests were done in duplicate.

The presence of transgene H chain immunoglobulins in the serum was detected using a capture ELISA (see Example I; Billetta and Zanetti, supra, 1992).

Ten milligrams of the tissue were digested in the presence of protease and the cell lysates were loaded onto the QIAamp spin column (Qiagen, Inc.; Chatsworth Calif.). After washing twice by centrifugation, the DNA was eluted from the column with distilled water and quantitated on a 1% agarose gel. PCR was performed with a total of four sets of primers, pCL and pCD; pSE and pNAD; pNEL and PNED; and pγA1 and pγA2. pCL (from −107 nt to −85 nt: 5'-TTATTGAGAATAGAGGA-CATCTG-3'; and pCD (from 459 nt to 439 nt: 5'-ATGCT-CATAAAACTCCATAAC-3'; were used to amplify the whole VDJ region of the transgene. pSE (from −32 nt to −11 nt: 5'-AACAGTATTCTTTCTTTGCAGC-3'; and pNAD (from 352 nt to 333 nt: 5'-GAGAGTAGGGTACTGGGTTT-3'; were specific for amplification of the genetic marker, $(NANP)_3$ in CDR3. pNEL (from 169 nt to 189 nt: 5'-AGCAC-CTACTATCCAGACACT-3'; and pNED (from 366 nt to 346 nt: 5'-GTAGTCCATACCATGAGAGTA-3'; were the inner primers for nested PCR. pγA1 (from 184 nt to 201 nt: 5'-TGGGCCGCCCTAGTCACC-3'; and pγA2 (from 427 nt to 408 nt: 5'-CGTTTGGCCTTAGGGTTCAG-3'; were designed to amplify the murine β-actin gene according to the sequence indicated in (Harris et al., Gene 112:265-266 (1992)). The PCR consisted of 30 cycles at 94° C. for 45 sec, 58° C. for 45 sec, and 72° C. for 45 sec; 0.3 µM each primer; 0.2 mM each deoxynucleotide; 1.5 mM $MgCl_2$ in 20 mM Tris-HCl, pH 8.4 and 50 mM KCl; and 1 unit of Taq DNA polymerase (Gibco BRL; Gaithersburg Md.). PCR products for Southern blot analysis were resolved in 1% w/v agarose gel and blotted onto HYBOND-N nylon membrane (Amersham; Cleveland, Ohio). The membranes were hybridized with the oligonucleotide pNAD labeled using T4 polynucleotide kinase forward reaction in presence of ($\gamma^{32}$P-ATP).

For DNA sequencing, a 566 bp DNA fragment containing the whole VDJ coding region was amplified from splenic genomic DNA using two primers (pCL and pCD) specific for the rearranged murine $V_H$. This fragment was subcloned into the pGEM-T vector (Promega; Madison Wis.). The plasmid DNA was extracted from transformed DH5γ *Escherichia coli* and sequenced by dideoxy termination method with SEQUENASE 2.0 DNA Sequencing Kit (USB; Cleveland, Ohio) using two primers (pSE and pCD) annealing in front of the FR1 and at the end of FR4 from opposite directions (see FIG. (11) 7B).

For fluorescence-activated cell sorting (FACS), spleen cells were prepared by grinding the spleen tissue harvested 15, 21 and 28 days after inoculation, or from naive mice. The cell suspension was washed twice with 0.5% PBSA and the red blood cells were removed by treatment with lysing buffer (Sigma; St. Louis Mo.). The lymphocytes were differentially stained with phycoerythrin (PE)-conjugated rat anti-mouse Ly-5 (B-220) Pan B-cell (Caltag; San Francisco Calif.), fluorescein isothiocyanate (FITC)-conjugated rat anti-mouse CD4 (Caltag) and FITC-conjugated rat anti-mouse CD8 (Caltag) for 20 min at 4° C. The cell suspension was washed twice in 0.5% PBSA and resuspended at the concentration of $5\times10^6$ cells/ml in DMEM (Irvine Scientific; Irvine Calif.). The cells were sorted on a FACSTAR (Becton & Dickinson; San Jose Calif.) at the Flow Cytometry core facility of UCSD Cancer Center. Genomic DNA was extracted from $1\times10^6$ B or T lymphocytes using the QIAAMP Blood kit (Qiagen). The DNA fragments were amplified by PCR and run on a 1% agarose gel. They were subsequently transferred to a nylon membrane for Southern blot hybridization using the (32P)-labeled pNAD oligonucleotide.

The experiments resulted in vivo production of transgene H chain immunoglobulins and a humoral response. Plasmid DNA γ1NANP (FIG. 1) was inoculated into the spleen of adult C57Bl/6 mice. Following a single intraspleen inoculation, transgene H chain immunoglobulins were detected (~12 ng/ml) in the serum of all mice inoculated with plasmid DNA γ1NANP but not in mice inoculated with the plasmid control pSVneo lacking the coding region for the H chain (Table 4). In all mice, antibodies against the γ1NANP, protein were also detected starting from week 2 (Table 4). This is in agreement with the results described in Example I.

TABLE 4

Detection of transgene H chain immunoglobulins and antibodies. to γ1NANP after intraspleen inoculation of plasmid DNA.

| Inoculum (plasmid) | No. of mice | Transgene H-chain Ig* (ng/ml) | Antibodies to γ1NANP** | | | |
|---|---|---|---|---|---|---|
| | | | 0 wk | 2 wk | 4 wk | 6 wk |
| γ1NANP | 10 | 11.9 | ≦2.3 | 2.8 ± 0.3 | 2.9 ± 0.4 | 3.0 ± 3.0 |
| pSVneo | 4 | 0 | ≦2.3 | ≦2.3 | ≦2.3 | 2.4 ± 0.2 |

*Presence of transgene H chain immunoglobulins was determined at 2 wk after a single DNA inoculation. Detection was performed using a capture ELISA.
**Antibodies are expressed as a Log titer. Titer determined as the last serum dilution giving an OD reading >0.200 ($A_{492}$).

Figure 7:
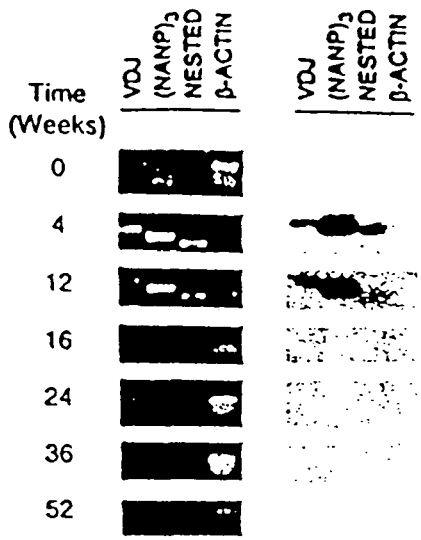
FIG. 7 shows PCR amplification and Southern blot hybridization to detect the presence of the transgene H chain in vivo. Panel A shows the presence of the transgene in splenic genomic DNA at various times after DNA inoculation. Spleens were harvested 4, 12, 16, 24, 36 and 52 weeks after DNA inoculation. The spleen of a naive mouse served as a negative control and is referred to as time 0. Detection of the transgene in the genomic DNA was performed by PCR amplification using three sets of primers (pCL/pCD, pSE/pNAD and pNEL/pNED) specific for three different DNA fragments of plasmid DNA γ1NANP and confirmed by Southern blot hybridization using the ($^{32}$P)-labeled PNAD oligonucleotide. The location and size of the PCR fragments (VDJ, (NANP)$_3$ and NESTED) are illustrated in Panel B. A PCR fragment identified as β-actin (for the murine β-actin gene) served as an internal control. Left, the results of PCR amplification. Right, the results of Southern blot hybridization. Panel B is a schematic representation of the $V_H$ gene contained in plasmid DNA γ1NANP. The annealing sites of the primers, the predicted amplification fragments and their molecular size, are identified: FR, framework region; VDJ refers to a fragment that is inclusive of the coding region for the rearranged VDJ gene segments; (NANP)$_3$ refers to a 384-bp fragment containing in the CDR3 of the $V_H$ region the sequence coding for three repeats of the tetrapeptide Asn-Ala-Asn-Pro between nucleotides 304 and 340; NESTED refers to a 198-bp fragment inclusive of the coding region for FR3 and the CDR3. +1 refers to the first nucleotide in the coding region of FR1. Any other position in the gene is numbered in reference to nucleotide +1. Panel C shows tissue distribution of the transgene in vivo. Genomic DNA was extracted from the tissues listed. Tissues were obtained at various times from DNA inoculation. Tissues from a naive mouse refers to time 0. Left, PCR amplification of the VDJ fragment of the transgene using the primers of pCL/pDC. Right, results of Southern blot hybridization using the ($^{32}$P)-labeled pNAD oligonucleotide.
Figure 7:
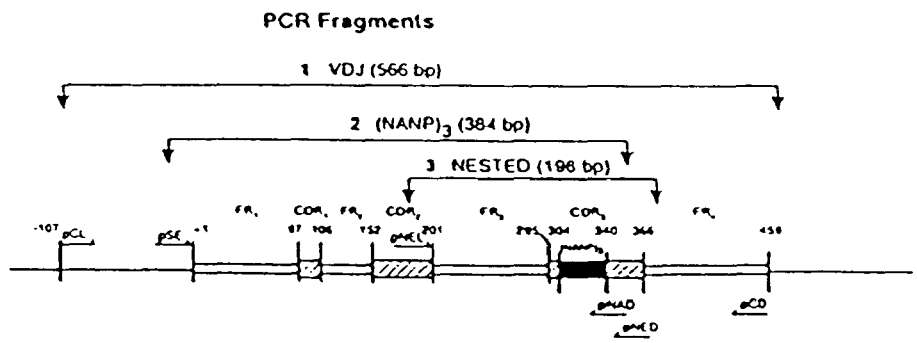
Figure 7:
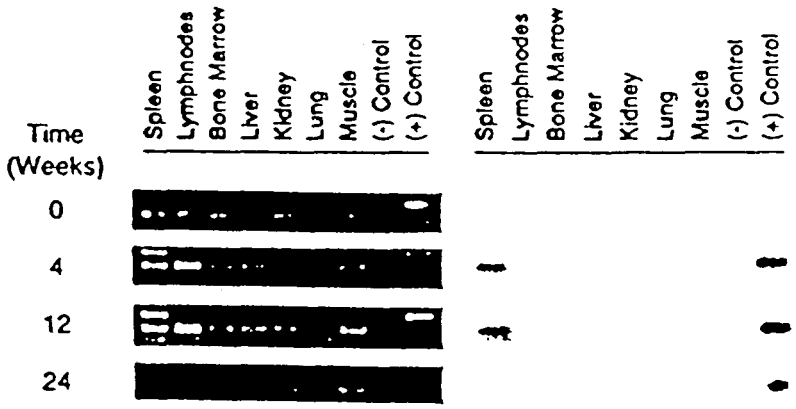

Kinetics and tissue distribution of the transgene in vivo were determined. To monitor the kinetics of detection of the transgene in vivo, genomic DNA extracted from the spleen of inoculated mice was analyzed by PCR and Southern blot hybridization at various times after inoculation. As shown in FIG. 7 (A, left panels), amplification of the transgene VDJ region was visible up to 12 weeks after a single DNA inoculation. No amplification was seen in the subsequent time points (16, 24, 36 and 52 weeks). To control for specificity and increase the sensitivity of the reaction, two additional PCR assays were performed using primers designed to anneal to sites within the VDJ region. One set of primers (pSE/pNAD) specifically amplified the $(Asn-Ala-Asn-Pro)_3$ coding sequence, and another (inner primers: pNEL/pNED) served for nested PCR (see FIG. 7B). The results confirmed those obtained with VDJ amplification. Southern blot analysis using a probe specific for the NANP-coding region further confirmed the PCR results (FIG. 7A, right panels). Thus, the transgene H chain persisted in vivo for a period of 3 months. To determine tissue distribution of the transgene in vivo, genomic DNA was extracted from various lymphoid, for example, spleen, lymph nodes and bone-marrow, and non-lymphoid, for example, liver, kidney, lung and muscle, tissues explanted at different times, and analyzed for specific amplification of the transgene VDJ by PCR. Whereas an amplification product was readily visible in splenic genomic DNA, no specific amplification occurred in any of the other tissues. This did not vary at any of the time points analyzed (FIG. 7C, left panels). Southern blot analysis confirmed the PCR results (FIG. 7C, right panels).

Figure 8:
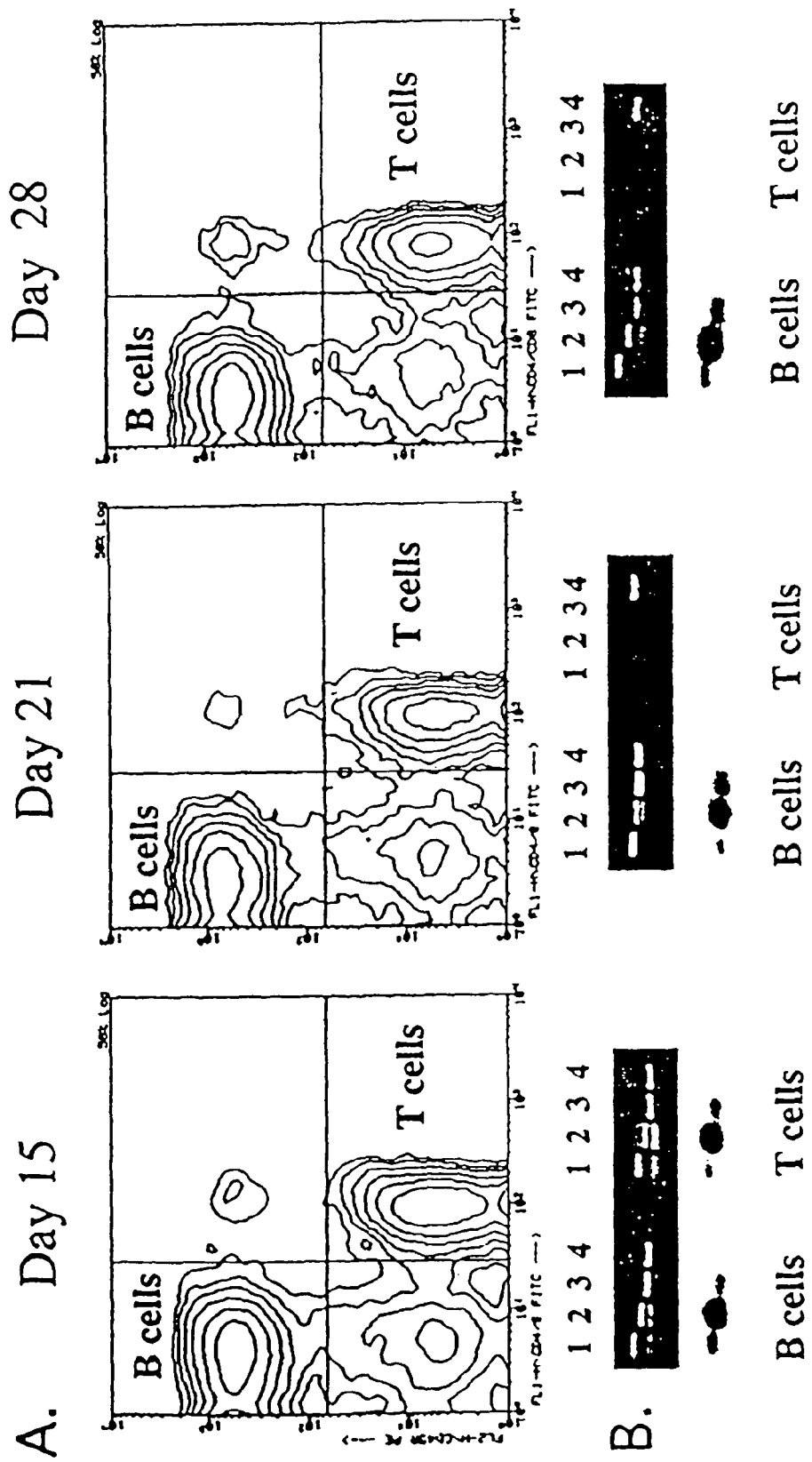
FIG. 8 shows isolation of splenic B and T lymphocytes and detection of the transgene H-chain in the purified lymphocyte populations. B and T lymphocytes from the spleen of DNA-inoculated mice were sorted and purified on a fluorescence-activated cell sorter at the times indicated. Lane 1, fragment amplified with the primers pCL/pCD(VDJ); lane 2, fragment amplified with the primers pSE/pNAD ((NANP)$_3$); lane 3, fragment amplified with the primers pNEL/pNED (NESTED); lane 4, fragment amplified with the primers pβA1/pβA2(β-actin).

To formally demonstrate that B lymphocytes were in fact the target cell population in vivo for the transgene, the following experiment was performed to detect the transgene in splenic lymphocytes. Starting from the second week after plasmid DNA inoculation, splenic B and T lymphocytes were isolated to a high degree of purity (97-99%) by FACS sorting (FIG. 8). The genomic DNA was extracted from the two cell populations and amplified by PCR using the same sets of primers as in FIG. 7. At the 15 day time point, distinct amplification products were readily detectable in both B and T lymphocytes (FIG. 8, left panel). However, at both the 21 and 28 day time points, specific amplification was observed only in B cells (FIG. 8, middle and right panels). Southern blot hybridization confirmed the specificity of the amplification products. These results suggested that B lymphocytes in the spleen are the target cell population in which the transgene persists for a long time. Together with the fact that the transgene could not be amplified from peripheral blood lymphocytes, these results indicate that the likely destiny of spleen B lymphocytes harboring the transgene is to remain localized in the tissue in which they were transfected.

The transgene was sequenced from genomic DNA. The immunogenic potential of a transgene-encoded product depends on the fact that no sense somatic mutation will affect the nucleotide sequence of the transgene while harbored in vivo. Hypermutation is of frequent occurrence in the VDJ region of Ig, and in particular in the CDRs, a fact in agreement with the notion that hypermutation takes place during antigen selection and affinity maturation of the antibody response (Griffiths et al., supra, 1984). Although the transgene used in this study lacks a transmembrane domain, rendering cell surface anchoring unlikely, experiments were nevertheless performed to assess the accumulation of mutations as a result of protracted in vivo persistence in integrated form. The transgene VDJ region was amplified from splenic genomic DNA, subcloned and sequenced by the dideoxy termination method. No evidence of hypermutation was found in the VDJ region of the transgene even after 3 months in vivo (Table 5).

TABLE 5

Lack of transgene mutations in PCR-generated clones from splenic genomic DNA.

| Time (wk) | No. of clones sequenced | No. of clones mutated | No. of nucleotides mutated | Rate of mutation* (%) |
|---|---|---|---|---|
| 2 | 6 | 1/6 | 1** | $2.9 \times 10^{-4}$ |
| 4 | 3 | 0/3 | 0 | |
| 12 | 3 | 0/3 | 0 | |

*Number of mutations per total number of base pairs sequences.
**A silent (C to T) mutation in FR3.

These results demonstrate that in vivo inoculation with plasmid DNA resulted in expression of the transgene in B cells of the spleen for at least three months.

EXAMPLE III

Immunity to *Plasmodium falcilarum* Malaria Sporozoites by Somatic Transgene Immunization This example describes administration of a nucleic acid molecule encoding a B-cell epitope of *P. falciparum* malaria parasite to induce an immune response against the parasite antigen.

The protocols used are described below (Gerloni et al., Nature Biotech. 15:876-881 (1997)).

Eight to ten week old C57BL/6 ($H-2^b$) mice were purchased from the Jackson Laboratories (Bar Harbor Me.). Mice were maintained in the animal facility of the University of California, San Diego, and were handled according to UCSD and NIH regulations.

γ1NANP is described in Example I. pSV2Neo is the original plasmid forming the backbone of the pNγ1 vector without the human γ1 C region gene. This plasmid was used as a control in the immunization experiments. Plasmid DNA was prepared from DH5α *Escherichia coli* and purified according to standard procedures.

The antigenized antibody γ1NANP was produced and purified as described previously (Billetta et al., supra, 1991) and stored at −20° C. until use. The recombinant antigen R32LR consisting of 30 repeat of the tetrapeptide NANP fused to 32 amino acids derived from the $tet^r$ region of the PAS1 plasmid was prepared as described (Wirtz et al., Exp. Parasitol. 63:166-172 (1987)). A synthetic peptide containing multiple repeats of the NANP sequence, (NANP)n. Control peptide DENGNYPLQC is from the sequence of the human invariant chain. *P. falciparum* sporozoites were produced in *Anopheles freeborni* mosquitos infected as described (Wirtz et al., supra, 1987).

The detection of antibodies to synthetic peptide (NANP)n was done as described in Example II. Antibodies to intact γ1NANP protein and R32LR antigen were detected on plates coated (2.5 μg/ml) with the corresponding substrate by drying at 37° C. After coating, wells were blocked with 1% bovine serum albumin (BSA) in phosphate buffered saline (PBS) 0.15 M, pH 7.3. Wells were incubated overnight at 4° C. with mice sera diluted in 1% BSA-PBS, containing 1% TWEEN-20 (PBSA). The bound antibodies were revealed using a goat antibody to mouse immunoglobulin absorbed with human immunoglobulin and conjugated with horseradish peroxidase (HP) (Sigma; St. Louis Mo.). The bound peroxidase activity was revealed by adding o-phenylenediamine dihydrochloride and $H_2O_2$. Plates were read after 30 min in a micro-plate reader (VMAX; Molecular Devices) at 492 nm. Control plates coated (2.5 μg/ml) with synthetic peptide DENGNY-PLQC were coated similarly to plates coated with the synthetic peptide NANP.

The presence of the transgene H chain immunoglobulins in the serum of mice was detected using a capture ELISA assay (Billetta and Zanetti, supra, 1992) as in Example I. Ig class determination of anti-(NANP)n and anti-γ1NANP antibodies was done by ELISA using isotype-specific rabbit antibodies (Mouse Typer Sub-isotyping kit; Bio-Rad; Hercules Calif.). Microtiter wells were coated with synthetic peptide (NANP)n (2.5 μg/ml) at 4° C. in 0.1 M carbonate buffer, pH 8.6, or with γ1NANP protein (2.5 μg/ml) in 0.9% NaCl by drying at 37° C. Plates were blocked with 1% BSA. Pooled mouse sera diluted in PBSA were incubated overnight at 4° C. After washing, 100 μl of anti-isotype antibodies at the dilution recommended by the manufacturer were incubated for 3 hrs at room temperature. The bound antibodies were revealed by adding (100 μl/well) of HP-conjugated goat antibody to rabbit Ig diluted 1:3,000 in PBSA for one hr at room temperature. The test was continued as described above. Tests were done in duplicate.

Sera diluted 1:50 were assayed for immunofluoresence reactivity with air dried *P. falciparum* sporozoites at various dilutions (1:25 to 1:800). The assays were performed as previously described (Wirtz et al., supra, 1987). Fluorescence intensity was graded from 0 to 4+, with 0 indicating no fluorescence detectable and 4+ indicating intense fluorescence over the entire surface of the sporozoites. Sample with ≧+ fluorescence intensity were considered positive.

Mice were inoculated with 100 μg of plasmid DNA in 30 μl of sterile saline solution intraspleen as detailed under Example I. In the experiment described in Table 6 mice, were boosted with 100 μg of plasmid DNA γ1NANP in saline administered intravenously via the tail vein. Inoculation of DNA via other routes was performed as described (see Example I).

TABLE 6

Titers (log₁₀) if antibodies reacting with NANP peptide after priming and booster immunizations.

| Group | Priming* | Booster | No. of mice | Primary immune response (days) | | | | Secondary immune response (days) | | |
|---|---|---|---|---|---|---|---|---|---|---|
| | | | | 0 | 14 | 28 | 53 | 200 | 214 | 228 |
| I | γ1NANP DNA | γ1NANP DNA | 4 | ≦2.3 | 2.6 | 2.8 ± 0.2 | 2.8 ± 0.2 | 2.9 ± 0 | 2.9 ± 0 | 2.9 ± 0 |
| II | γ1NANP DNA | γ1NANP protein | 4 | ≦2.3 | 2.6 | 2.9 | 2.8 ± 0.2 | 3 ± 0.2 | 3.6 ± 0.3 | 3.7 ± 0.4 |
| III | pSVneo DNA | γ1NANP protein | 4 | ≦2.3 | ≦2.3 | ≦2.3 | ≦2.3 | ≦2.3 | ≦2.3 | ≦2.3 |
| IV | γ1NANP protein | γ1NANP protein | 4 | ≦2.3 | ≦2.3 | ≦2.3 | ≦2.3 | 2.4 ± 0.3 | 2.5 ± 0.4 | 2.6 ± 0.6 |
| V | OVA protein | OVA protein | 4 | ≦2.3 | ≦2.3 | ≦2.3 | ≦2.3 | ≦2.3 | ≦2.3 | ≦2.3 |

*All priming injections were done through the intraspleen route. Booster injections were done on day 200. In all but one group (group 1, which was done intravenously) booster injections were done subcutaneously.

Mice were inoculated i.s. with affinity-purified γ1NANP protein in sterile saline solution. The surgical procedures were as described above. Mice were immunized with affinity-purified γ1NANP protein emulsified in complete Freunds' adjuvant (50 μg per mouse) subcutaneously. Mice that were boosted with the γ1NANP protein received 50 μg of the protein emulsified in incomplete Freunds' adjuvant subcutaneously or 50 μg of the protein adsorbed on alum intraperitoneally. $10^5$ irradiated sporozoites in incomplete DMEM were injected intraperitoneally in a 0.4 ml volume. Mice were bled via the retro-orbital route.

Figure 9:
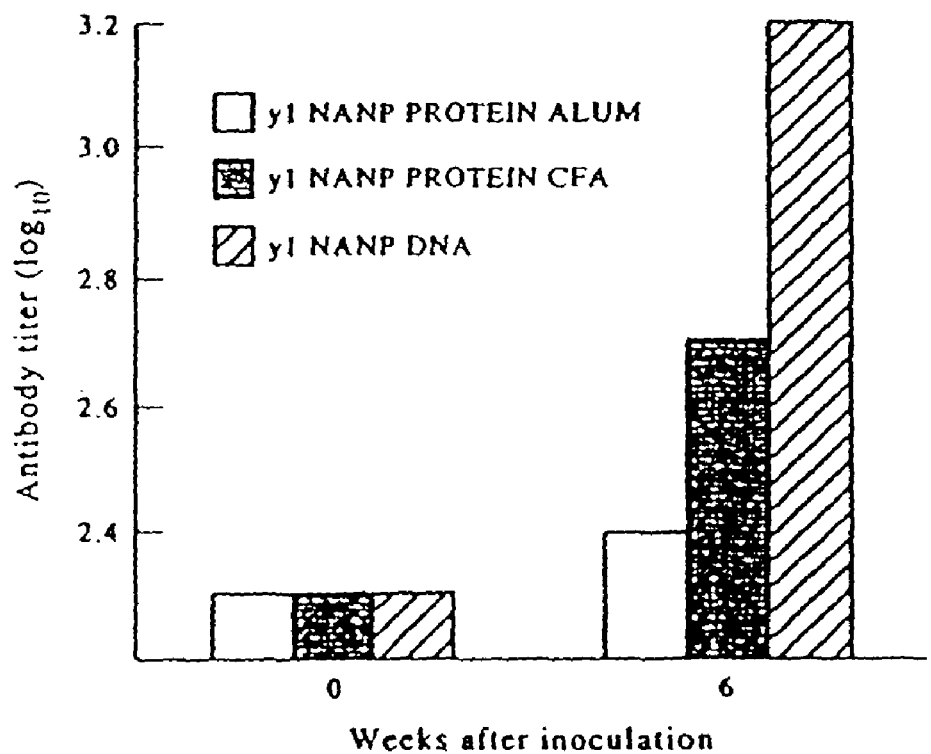
FIG. 9 shows the specificity of the primary anti-NANP peptide response after intraspleen inoculation of plasmid DNA. Mice were inoculated with γ1NANP DNA (12 animals) or with control plasmid pSVneo DNA (four animals). Sera were tested by ELISA on synthetic peptide (NANP)n. Data shown represent the mean of individual titers which were determined on the basis of the last value with an absorbance $\geq$ of 0.200 ($A_{492}$).

Inoculation of plasmid γ1NANP DNA γ1NANP induces a primary response against the peptide NANP. Previously, immunization was demonstrated with an antibody antigenized with three NANP repeats in the CDR3 of the heavy (H) chain (γ1NANP) induced antibodies that recognized the CS repeat epitope in mice and rabbits (Billetta et al., supra, 1991). These antibodies also reacted with P. falciparum sporozoites by indirect immunofluorescence. To determine whether a similar antibody response against (NANP)3 peptide could be induced, immunocompetent C57/Bl6 mice were inoculated with plasmid DNA coding for the γ1NANP gene (FIG. 9). These experiments were based on the work showing that an immunoglobulin H chain transgene could induce immunity if inoculated directly into the spleen (i.s.) (see Example I) but not if introduced using other routes of immunization (intramuscular, intravenous, intradermal and subcutaneous)

Table 6 summarizes the ELISA antibody responses in which anti-NANP peptide antibodies were found in mice primed with the H chain transgene (γ1NANP DNA) (groups I and II). Antibodies appeared by day 14 and reached a plateau by day 28 (log 2.8) (Table 6). Circulating antibodies persisted through day 200 when mice received a booster injection. The antibody response against the intact antigenized antibody γ1NANP paralleled the response against the synthetic peptide. Mice inoculated intrasplenically with 50 μg of the γ1NANP protein (group IV) failed to mount any measurable anti-peptide response, although a modest elevation in titer against the intact γ1NANP antibody was measured. Control groups injected with either the pSVneo plasmid or with ovalbumin failed to develop any antibody response above background titers higher than the pre-immunization values. No binding was observed when the same sera were tested on the synthetic peptide DENGNYPLQC used as a control.

Memory response against the NANP peptide was induced by γ1NANP DNA. A single intrasplenic inoculation of plasmid γ1NANP DNA γ1NANP was sufficient to induce immunologic memory against the (NANP)3 peptide expressed in the CDR3 of the H chain transgene. Table 6 shows the secondary anti-peptide response following a subcutaneous booster injection of the γ1NANP protein in incomplete Freunds' adjuvant (groups II and IV). The antibody titer against the synthetic NANP peptide rose in all animals in group II, and paralleled the response against the intact γ1NANP protein. In contrast, no anamnestic response occurred in mice boosted with a second intravenous injection of γ1NANP DNA (group I) perhaps because of the rapid degradation of plasmid DNA by plasma DNAses. The antibody response in mice primed by i.s. inoculation with soluble γ1NANP protein and boosted with γ1NANP protein subcutaneously (group IV) was similar to that seen with primary immunizations using the recombinant protein alone. No antibody responses against NANP were detected in control mice (groups III and V).

Transgenic H chain immunoglobulins were detected in the serum of all mice inoculated with plasmid DNA γ1NANP DNA (FIG. 15D) with a concentration ranging between 4.8 and 30.1 ng/ml (average 11.9±6.2 ng/ml).

Figure 10:
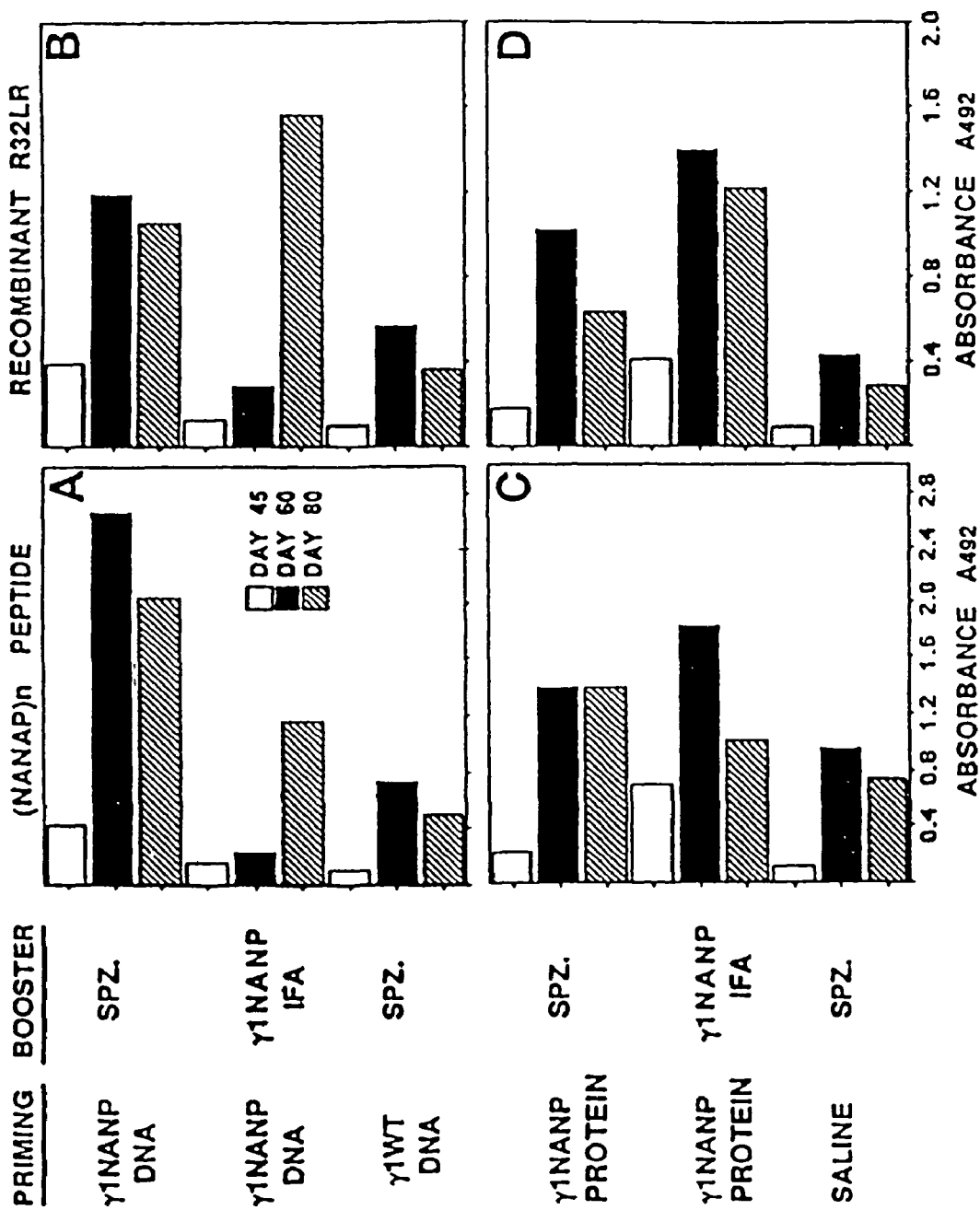
FIG. 10 shows the anamnestic response elicited with plasmid γ1NANP DNA following challenge with *P. falciparum* sporozoites. Mice were primed with plasmid DNA γ1NANP or antigenized antibody γ1NANP or antigenized antibody γ1NANP in CFA as indicated. Control groups were inoculated with plasmid γ1WT DNA or saline. On day 45 mice were given a booster immunization with either *P. falciparum* sporozoites or antigenized antibody γ1NANP (50 μg) in IFA subcutaneously as indicated. *P. falciparum* sporozoites were inoculated (10$^9$) in incomplete DMEM intraperitoneally. Blood samples were collected on day 45 (before the booster injection) and subsequently 15 and 35 days after booster. Antibodies reactive with the synthetic peptide (NANP)n (panels A and C) and antibodies reactive with the recombinant protein R32LR (panels B and D) were detected by ELISA. Values represent the absorbance ($A_{492}$) of pooled sera (four mice/group) tested at 1:1600 dilution.

Immunization with γ1NANP DNA induced immunologic memory response against P. falciparum sporozoites. To verify whether somatic transgene immunization could prime for immunologic memory upon encounter with the native CS protein of the parasite, mice were boosted by a single injection of P. falciparum sporozoites. The resulting antibody response was measured by ELISA. For comparison, mice were divided into two groups. One group was primed i.s. with plasmid DNA γ1NANP (or its control γ1WT). A second group was primed subcutaneously with antigenized antibody γ1NANP in complete Freunds' adjuvant. Forty-five days after priming, mice were boosted with a single intraperitoneal injection of $10^5$ P. falciparum sporozoites or with antigenized antibody γ1NANP in incomplete Freunds' adjuvant by subcutaneous injections. Control groups included mice primed with plasmid γ1WT DNA or saline, and subsequently boosted with sporozoites. Mice primed with γ1NANP DNA and boosted with sporozoites (FIG. 10) mounted a secondary response against NANP that was absent in mice primed with control plasmid DNA or with saline alone. Moreover, the anamnestic responses to sporozoites were greater in mice primed with γ1NANP DNA than in mice primed with the antigenized antibody γ1NANP in complete Freunds' adjuvant (CFA) (FIGS. 10A and 10C). Similar results were obtained when the sera were tested by ELISA on recombinant R32LR as capture antigen (FIGS. 10B and 10D).

Figure 11:
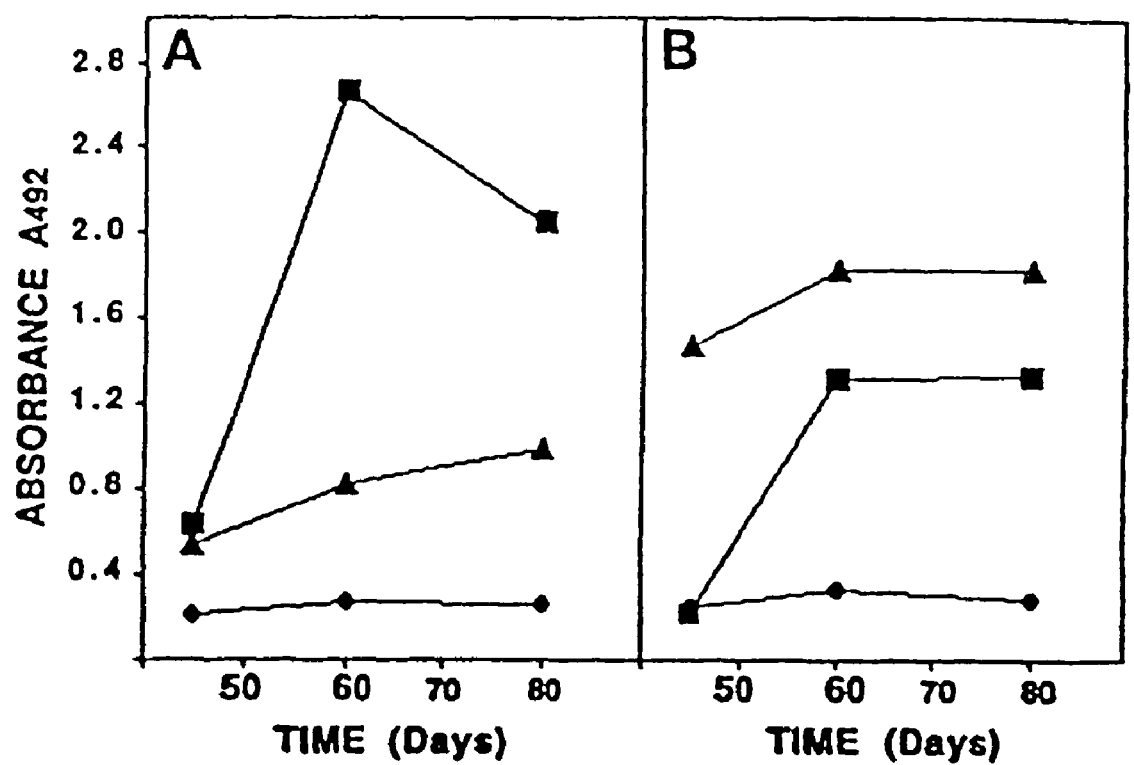
FIG. 11 shows challenge with *P. falciparum* sporozoites selectively restimulates clonotypes producing anti-NANP antibodies. Panel A shows the antibody response of mice primed with plasmid γ1NANP DNA. Panel B shows the antibody response of mice primed with antigenized antibody γ1NANP. In both instances serum antibodies were detected on microtiter wells coated with synthetic (NANP)n peptide (black boxes), antigenized antibody γ1NANP (black triangles), or control synthetic peptide (black circles). Values represent the absorbance ($A_{492}$) of pooled sera (four mice/group) tested at 1:1600 dilution.

FIG. 11 further demonstrates that γ1NANP DNA primed antibody responses to the native protein as found on the sporozoite surface. Anti-CS repeat antibodies were boosted in mice primed with γ1NANP DNA (FIG. 11A), that received sporozoites on day 45. Antibody responses against the NANP repeat were substantially higher than those against the γ1NANP protein. Similarly, mice primed with antigenized antibody γ1NANP (FIG. 11B) also responded to the booster injection with sporozoites, although less dramatically than did the mice primed with the transgene vaccine. These results indicate that STI primed for immunologic memory and resulted in a strong secondary anti-sporozoite response.

These sera also reacted strongly with the surface of air-dried sporozoites by indirect immunofluoresence assay (Table 7), confirming that the DNA-immunized mice had been primed with a B cell epitope with a conformation that was substantially similar to that present on the surface of the target pathogen.

TABLE 7

Antibodies reacting with *Plasmodium falciparum* sporozoites by IFA.

| Priming* | Booster* | IFA reactivity Titer[r] |
|---|---|---|
| γ1NANP DNA | — | 25 |
| γ1NANP DNA | Sporozoite | 400 |
| γ1NANP DNA | γ1NANP protein | 50 |
| γ1NANP protein | — | 0 |
| γ1NANP protein | Sporozoite | 50 |
| γ1NANP protein | γ1NANP protein | 800 |

Figure 4:
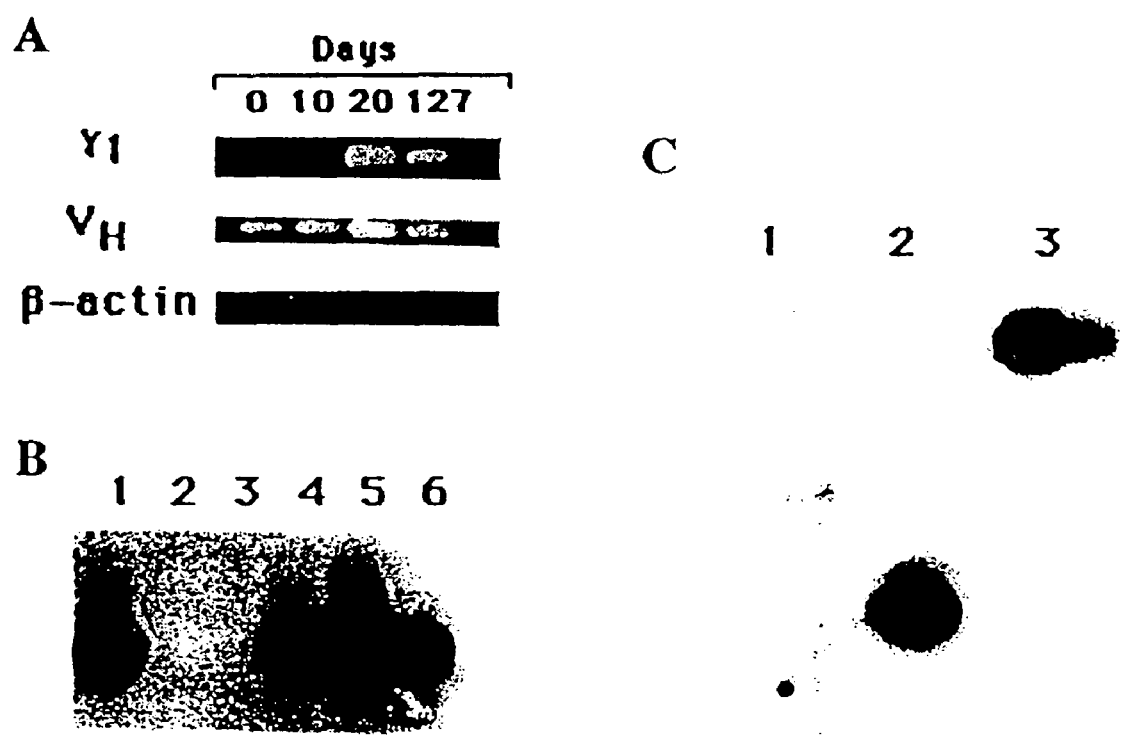
FIG. 4 shows studies on transgene transcription. Panel A shows semiquantitative analysis of the human γ1 C (466 bp) and murine $V_H^{62}$ (198 bp) region genes at sequential times (0, 10, 20 and 127 days) after intraspleen DNA inoculation. cDNA was reverse-transcribed from mRNA, extracted from equal amounts (11 mg) of frozen spleen tissue, and used as a template DNA for further amplification by PCR. β-actin DNA served as a control for mRNA content. Panel B shows Southern blot analysis of the PCR-amplified product from spleen of animals inoculated with plasmid DNA γ1WT and harvested at successive times (0, 10, 20 and 127 days) after intraspleen DNA inoculation. The PCR product was probed with a specific synthetic oligonucleotide for the human γ1 C region probe. Lane 1 shows the 466 bp gene segment of the human γ1 C region amplified from the plasmid pNeoγ1, which was used as a positive control. Lane 2 shows the amplified 198 bp murine $V_H^{62}$ gene used as negative control; lane 3-6: DNA amplified with human γ1 C region-specific primers at different times (0, 10, 20 and 127 days) after intraspleen DNA inoculation. Panel C shows Southern blot analysis of the PCR-amplified $V_H$ product (240 bp) from the spleen of a mouse inoculated with γ1NANP DNA and harvested on day 15. The PCR product was probed with a specific synthetic oligonucleotide for the NANP coding sequence in CDR3. Lane 1 shows DNA from a naive mouse. Lane 2 shows cDNA amplified with murine $V_H$ region-specific primers. Lane 3 shows plasmid DNA γ1NANP (positive control).

*Priming and booster injections refer to FIG. 4. Sera were tested as pools of four mice each. Values shown represent the reciprocal of the last positive dilution.

Figure 12:
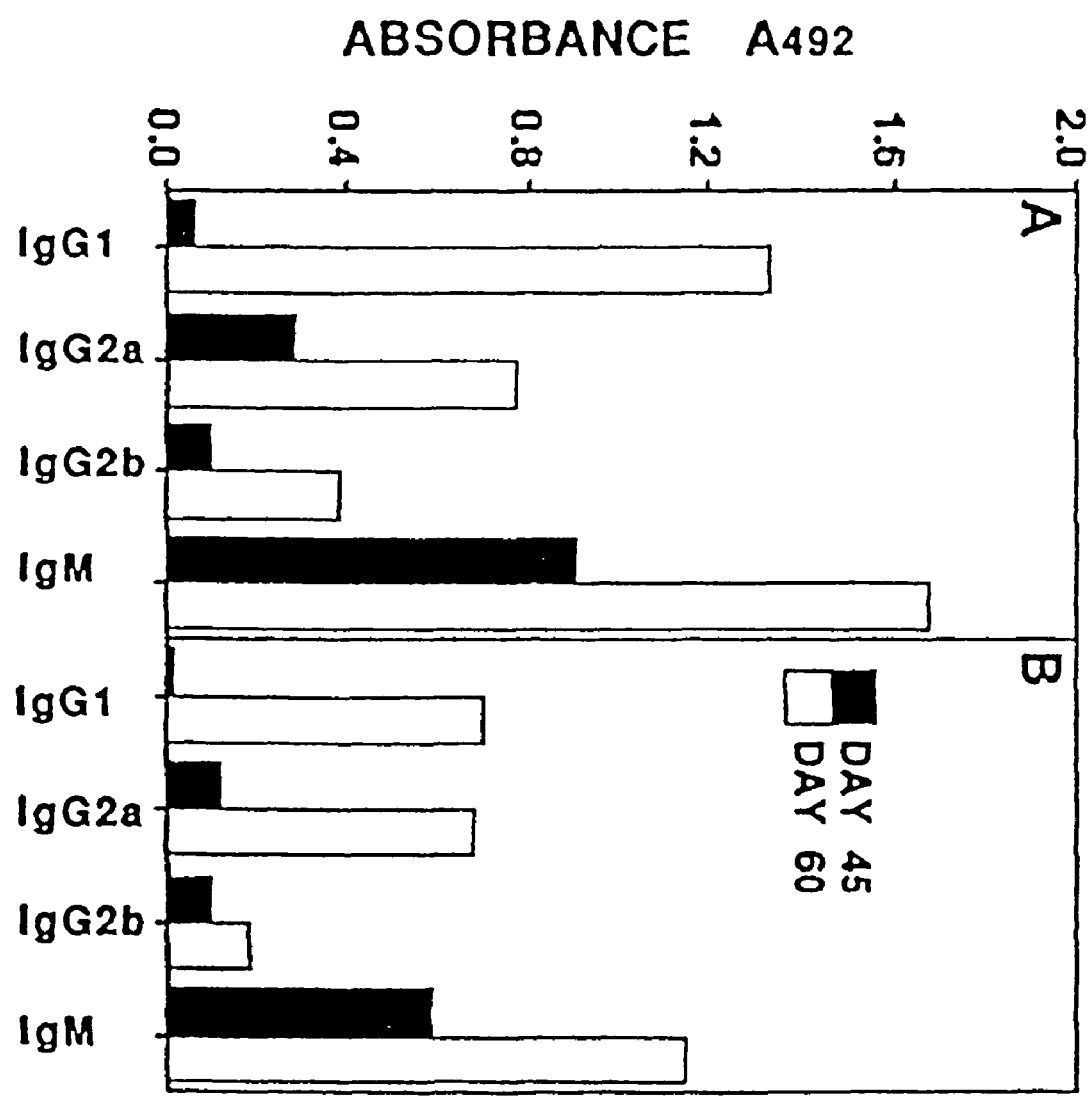
FIG. 12 shows isotype analysis of the primary and secondary antibody response against the (NANP)n peptide in mice primed intrasplenically with plasmid γ1NANP DNA. Mice received a booster immunization with 10$^5$ *P. falciparum* sporozoites (Panel A) or antigenized antibody γ1NANP (50 μg) in incomplete Freunds' adjuvant (Panel B) on day 45. Columns refer to determinations made in pool of sera from four individual mice. The time of blood collection is indicated. Values represent the absorbance ($A_{492}$) of tests done in duplicate on sera used at 1:1600 dilution.

Analysis of antibody isotype responses after priming showed that mice inoculated i.s. with plasmid γ1NANP DNA produced IgM and, to a lesser extent, IgG2a antibodies (FIG. 12). Booster with *P. falciparum* sporozoites enhanced specific antibodies of all isotypes, in particular IgG1 antibodies. Similarly, booster with the γ1NANP protein promoted the formation of IgG1 antibodies and a minor but significant rise in IgG2a and IgM antibodies. By comparison, booster with sporozoites yielded proportionally higher isotype responses in mice primed with the γ1NANP DNA than in mice primed with the γ1NANP protein in complete Freunds' adjuvant.

These results demonstrate that immunity to *P. falciparum* can be induced by administration of a nucleic acid molecule encoding a *P. falciparum* epitope.

EXAMPLE IV

Engineering Vaccines with Heterologous B and T Cell Epitopes Using Immunoglobulin Genes This example describes the insertion of heterologous B and T cell epitopes into the CDRs of an immunoglobulin to enhance the immunologic response when administered as plasmid DNA.

The experimental procedures are described below (Xiong et al., Nature Biotechnology, 15:882-886 (1997)).

Plasmid $γ1NV^2NA^3$ was engineered as described below. The EcoRI fragment of the productively rearranged murine $V_H$ (2.3 Kb) was cloned in vector pBluescript II KS to yield plasmid pVH. Site-directed mutagenesis was performed using two 21 mer oligonucleotide primers, one (5'-CAAGAAAGGTACCCTACTCTC-3') annealing in CDR3 to introduce 3 bp (TAC, in bold) for the creation of an Asp718 site, and another (5'-AGTAATGGCCATGGTAGCACC-3') annealing in CDR2 to introduce 3 bp (CCA, in bold) for the creation of a NcoI site. These primers were annealed to the uracylated, complementary strand of pVH and the mutant strands were synthsized and ligated in the presence of T4 DNA polymerase and ligase. Plasmid pVH-TAC/CCA, containing two unique sites, one in CDR3 (Asp718) and the other in CDR2 (NcoI), was obtained after transformation, screening of individual colonies and confirmation by DNA sequencing (SEQUENASE 2.0 DNA Sequencing Kit; USB; Cleveland Ohio). A pair of complementary oligonucleotides, 5'-GTACCCAATGCAAACCCAAATGCAAAC-CCAAATGCAAACCCA-3' (sense) and 5'-GTACTGGGTTTGCATTTGGGTTTG-CATTTGGGTTTGCATTGG-3' (antisense) coding for the (NANP)3 sequence was synthesized, annealed and cloned in the Asp718 site. A pair of complementary oligonucleotides 5'-CATGGTAATGCAAACCCAAATGTAGATC-CCAATGCCAACCCA-3' (sense) and 5'-CATGTGGGTTG-GCATTGGGATCTACATTTGGGTTTGCATTAC-3' (antisense) coding for the NANPNVDPNANP sequence was similarly cloned into the NcoI site. The insertions and the proper orientation were verified by dideoxy sequencing (SEQUENCASE 2.0 DNA Sequencing Kit; USB). The 2.3Kb EcoRI fragment carrying the engineered CDR3 and CDR2 was then subcloned in the expression vector pNγ1 (Sollazzo et al., supra, 1989) upstream from the human γ1 constant (C) region using the unique EcoRI site to yield plasmid $γ1NV^2NA^3$. Plasmid γ1NANP carries a productively-rearranged murine V region gene in which only the CDR3 was modified by introducing the nucleotide sequence coding for three NANP repeats (Sollazzo et al., supra, 1990a). The promoter and enhancer elements in these plasmids are those constitutively existing in Ig H chain genes (Sollazzo et al., supra, 1989).

Plasmid DNA was prepared from transformed DH5α *Escherichia coli* according to procedures described in Example I. Eight week old C57Bl/6 ($H-2^b$) female mice were purchased from the Jackson Laboratories (Bar Harbor Me.). Mice were maintained in the animal facility of the University of California, San Diego, throughout the duration of the experiments. Mice were inoculated with 100 μg of plasmid DNA in 50 μl volume of sterile saline solution as in Example I.

The recombinant antibodies γ1WT and γ1NANP were produced and purified as described previously (Billetta and Zanetti, supra, 1992; Sollazzo et al., supra, 1989) and stored at −20° C. until use. The synthetic peptide containing multiple repeats of the NANP sequence was the kind gift of Dr. A. Verdini (Monterotondo, Italy) and peptide NANPNVDPNANP was synthized in the peptide synthesis facility of the University of California, San Diego.

Antibodies to the (NANP)3 and NANPNVDPNANP peptides were detected by ELISA on 96-well polyvinyl microtiter plate (Dynatech, Gentilly, Va.) coated with synthetic peptide (2.5 μg/ml) in 0.1 M carbonate buffer, pH 8.6, by incubation overnight at 4° C. After coating, wells were blocked with 1% BSA in PBS and then incubated overnight at 4° C. with mice sera diluted in phosphate buffered saline (PBS), 0.15 M, pH 7.3, containing in 1% bovine serum albumin (BSA) and 0.05% TWEEN-20. The bound antibodies were revealed using a HP-conjugated goat antibody to mouse Ig absorbed with human Ig (Sigma) (1:10,000 dilution). The bound peroxidase was revealed by adding o-phenylenediamine dihydrochloride and $H_2O_2$. Plates were read after 30 min in a micro-plate reader (VMAX; Molecular Devices) at 492 nm.

Detection of antigenized antibodies in culture supernatants and transgene H chain Ig in mice sera was performed by a capture ELISA assay (Billetta and Zanetti, supra, 1992).

Briefly, culture supernatants or individual mouse sera (1:10 dilution) in PBS-BSA containing 0.05% TWEEN-20, were incubated overnight at 4° C. on 96-well plates coated with goat antibody to human IgG1 (10 µg/ml). The concentration of the transgene H chain Ig was calculated by plotting O.D. values of test samples against a standard curve constructed with known amount of human IgG1 spiked into PBS-BSA 0.05% TWEEN-20 containing 10% normal mouse serum. The bound antibodies were revealed using a HP-conjugated goat antibody to human Ig (Sigma) (1:1,000 dilution). The assay was continued as described above. Tests were done in duplicate.

Detection of κ and λ light chains in circulating transgene H chain Ig was done with a modification of the above assay. Briefly, serum transgene H chain Ig were captured on 96-well plates coated with goat antibody to human IgG1 (10 µg/ml) by incubation overnight at 4° C. The presence of murine light chains was assessed using a 1:2000 dilution of HP-conjugated goat antibodies to murine κ or λ light chains adsorbed with human Ig (Caltag; San Francisco Calif.). The assay was continued as described above. Tests were done in duplicate.

The engineering of two distinct epitopes in the same Ig V region gene was performed in the CDR3 and the CDR2 which contain a Asp718 (Sollazzo et al., supra, 1990b) and NcoI site, respectively. In the expressed proteins, both CDRs are loops interconnecting β-strands on the same β-sheet of the V domain. A modification of these two CDRs was expected to be compatible with proper VH/VL scaffolding, whereas engineering of the CDR1, which connects two different sheets of the V domain, could result in misfolding of the polypeptide. The B cell epitope used consisted of three repeats of the tetrapeptide Asn-Ala-Asn-Pro (NANP) from the CS antigen of *P. falciparum* parasite (Zavala et al., supra, 1985).

The Th cell epitope used is the peptide Asn-Ala-Asn-Pro-Asn-Val-Asp-Pro-Asn-Ala-Asn-Pro (NANPNVDPNANP), a conserved peptide sequence located in the 5' region of the CS antigen of *P. falciparum*. This peptide is recognized by immune human CD4+ T lymphocytes (Nardin, et al., Science 246:1603-1606 (1989), is immunogenic for several MHC haplotypes in the mouse (Munesinghe et al., supra, 1991) and has been included in multiple-antigen-peptide vaccines for malaria.

Figure 15:
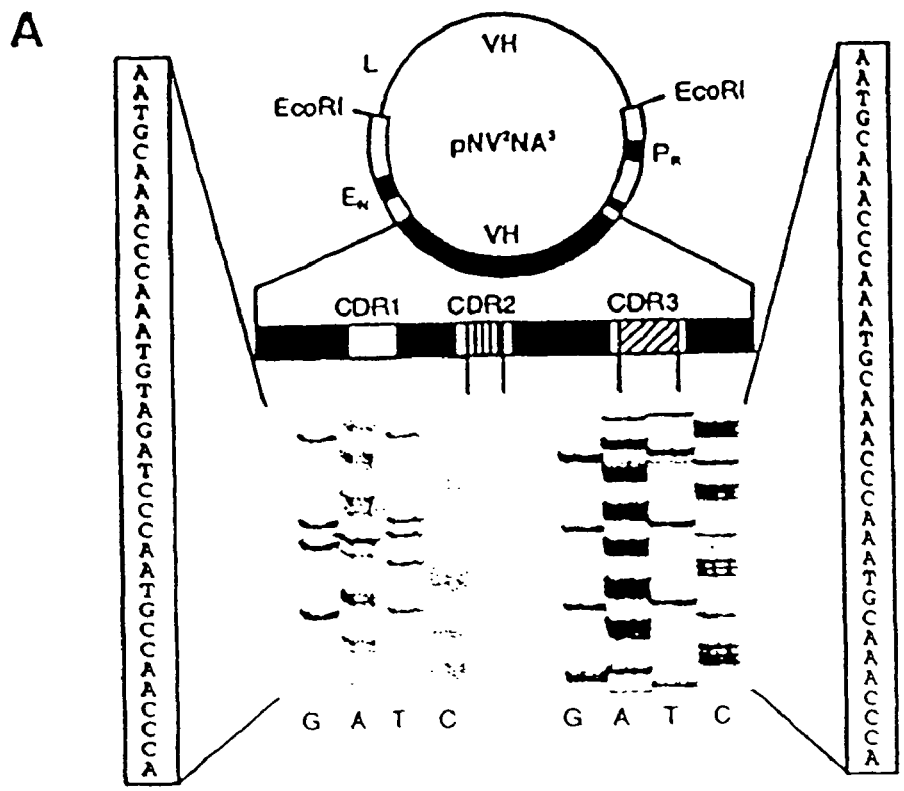
FIG. 15 shows engineering and expression of an immunoglobulin H chain gene with two heterologous epitopes. Panel A shows a schematic representation of the mutagenesis vectors, introduction of the (NANP)3 and NANPNVDPNANP coding sequences and partial, nucleotide sequence of CDR2 and CDR3 after insertion. The synthetic oligonucleotides and the mutagenesis steps for the creation of pVH-TAC/CCA are detailed in the Experimental Protocol. Two pairs of complementary synthetic oligonucleotides coding for (NANP)3 and NANPNVDPNANP, were cloned in the Asp718 site in CDR3 and in the NcoI site in CDR2 of pVH-TAC/CCA. The insertions were verified by dideoxy-chain-termination sequencing. Panel B shows a schematic representation of plasmid DNA γ1NV$^2$NA$^3$ carrying the coding sequences for the two heterologous epitopes in CDR3 and CDR2, respectively. The human γ1 constant (C) region gene is in genomic configuration. CH1, CH2, and CH3 refers to the corresponding domains in the C region of the γ1 gene. Promoter (Pr) and enhancer (En) elements for tissue-specific expression and the neomycin (Neo$^r$) and ampicillin (Amp$^r$) resistance genes are indicated. Panel C shows a schematic representation of antigenized H chain gene product paired with a light chain. The engineered epitopes in CDR3 and CDR2 are as indicated (not to scale).
Figure 15:
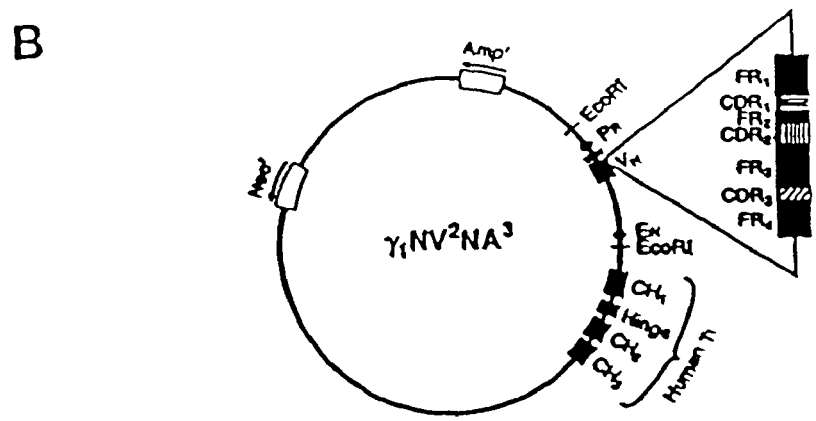

The CDR3 and CDR2 of pVH were engineered as illustrated in FIG. 15. The 2.3 Kb EcoRI DNA fragment carrying a productively-rearranged murine $V_H$ cloned into pBluescript (pVH) was modified by oligonucleotide site-directed mutagenesis to introduce two unique cloning sites, Asp 718 site in CDR3 (Sollazzo et al., supra, 1990a) and NcoI in CDR2 (pVH-TAC/CCA). A pair of complementary synthetic oligonucleotides coding for three NANP repeats was cloned into the Asp 718 site whereas the pair coding for the NANP-NVDPNANP sequence was cloned into the NcoI site of pVH-TAC/CCA. Nucleotide insertion and the correct orientation were checked by PCR and confirmed by sequencing (FIG. 15A). The engineered 2.3 Kb EcoRI fragment was then cloned into the unique EcoRI site of the expression vector pNγ1 to yield plasmid γ1NV²NA³ (FIG. 15B). The V region gene of plasmid γ1NV²NA³ codes, therefore, for two distinct epitopes of the CS antigen, one in CDR3 and the other in CDR2.

Figure 16:
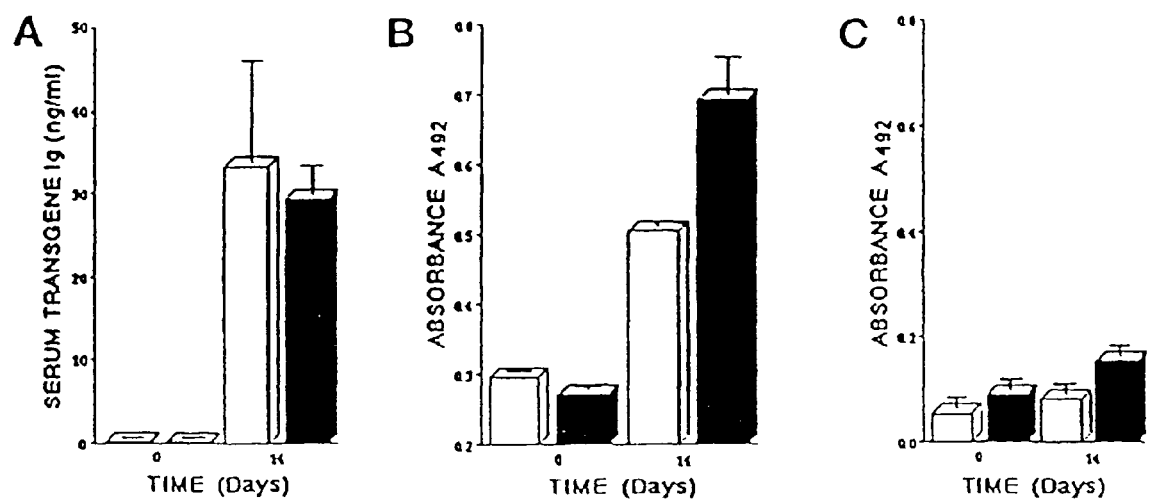
FIG. 16 shows in vivo expression of antigenized antibodies γ1NV$^2$NA$^3$. Panel A shows detection of transgene H chain Ig in the serum of mice inoculated with plasmid DNA γ1NANP (hatched columns) or γ1NV$^2$NA$^3$ (grey columns). Sera were tested at 1:10 dilution. Values (ng/ml) are expressed as the mean (±standard deviation) of four mice/group. Panel B shows detection of κ light chain associated with secreted transgene H chain Ig. Results are expressed as absorbance at 492 nm of sera tested at 1:1,600 dilution. Panel C shows detection of λ light chain associated with secreted transgene H chain Ig. Results are expressed as absorbance at 492 nm of sera tested at 1:1,600 dilution. Time refers to days after DNA inoculation.

In vivo expression of transgene H chain antibodies was determined. As described in Example I, following intraspleen inoculation of plasmid DNA coding an Ig H chain gene, transgenic Ig were invariably detected in the circulation in amounts ranging between 15 and 30 ng/ml 10. Similar amounts were detected in mice inoculated with the antigenized H chain gene coding for the NANP epitope in CDR3 (see Example III). Mice inoculated with plasmid γ1NV²NA³ secreted transgene H chain Ig in amounts comparable to those secreted by mice inoculated with plasmid DNA γ1NANP (29.4 vs. 33.3 ng/ml) (FIG. 16A). These results indicate that, as observed in vitro, the modifications in the two CDR loops did not impact folding and secretion of transgene H chain Ig associated with endogenous γ light chains (FIG. 16B versus 16C). Collectively, these results suggest that transgene H chains with insertion of heterologous dodecapeptides in two CDRs are handled in vivo as conventional Ig H chain genes and pass quality control mechanisms in the endoplasmic reticulum similarly to endogenous Ig molecules.

Figure 17:
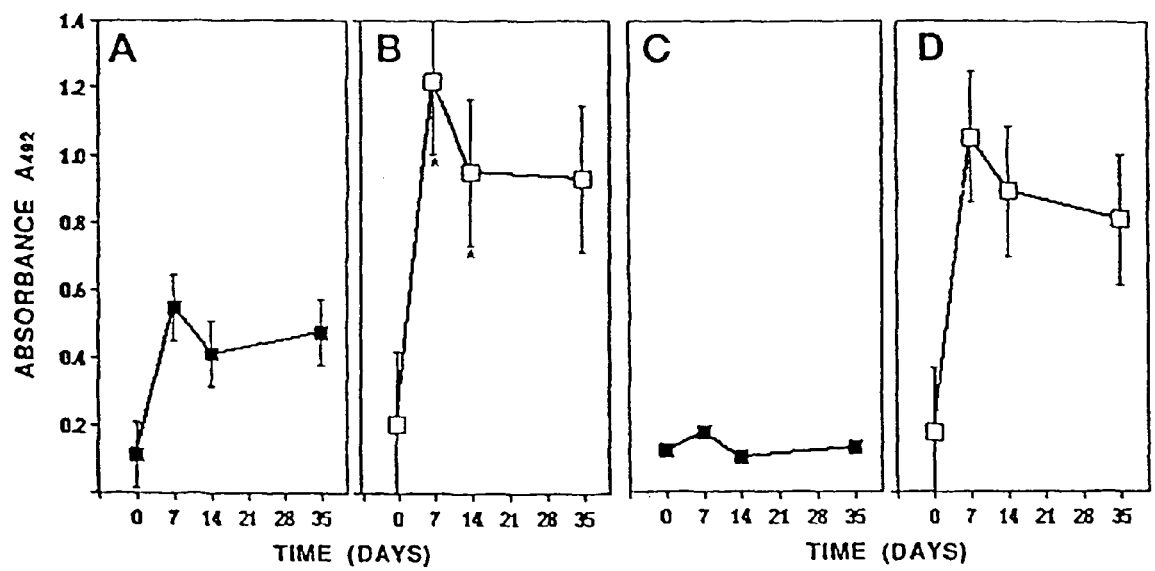
FIG. 17 shows in vivo immunogenicity of CDR3 and CDR2 epitopes. Mice were immunized with plasmid DNA γ1NANP (black squares) or γ1NV$^2$NA$^3$ (open squares). Their sera were tested by ELISA on synthetic peptide (NANP)n (panels A and B) or NANPNVDPNANP (panels C and D). Values refer to absorbance (492 nm) of sera tested at 1:1600 dilution and are expressed as the mean (±standard error). Each group consisted of four mice. (*) indicates statistical significance between the values shown in panel B versus panel A. Significance was p<0.01 on day 7, and p<0.05 on day 14. Time refers to days after DNA inoculation.
Figure 18:
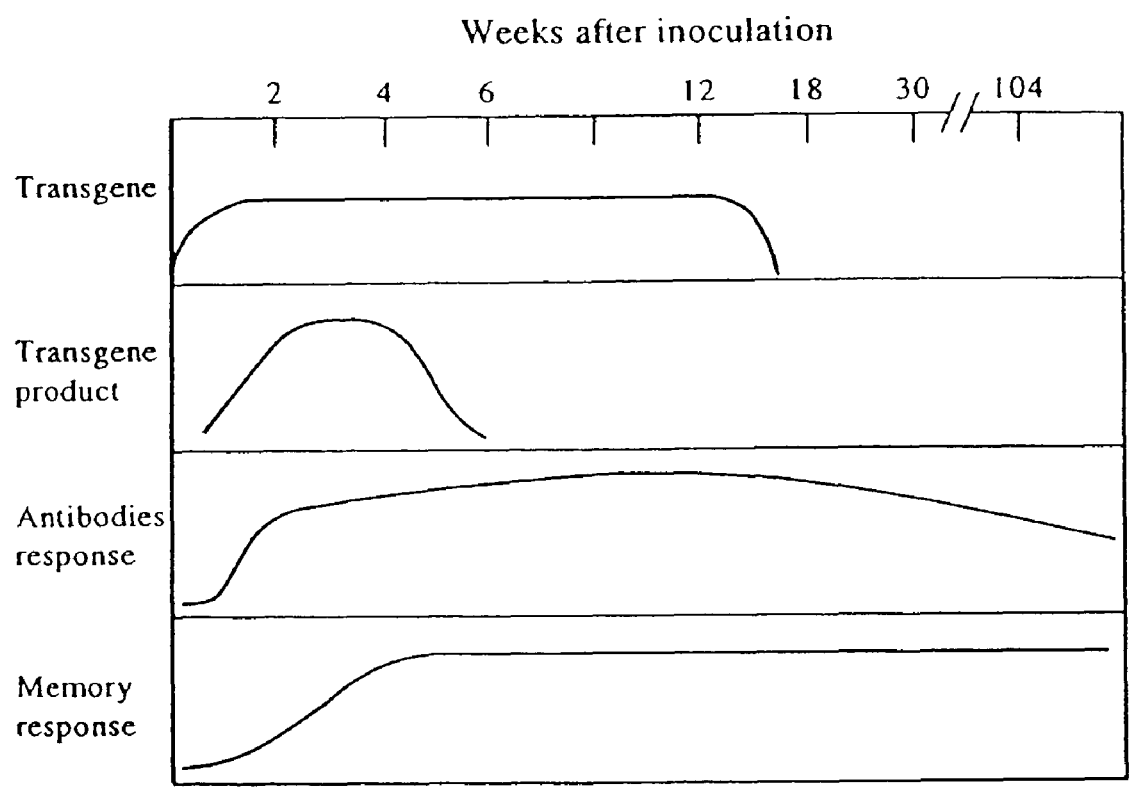
FIG. 18 shows a schematic view of the temporal relationship between detection of the transgene in vivo, detection of transgene product and respective antibodies in the circulation, and presence of immunologic memory during STI.

To determine in vivo immunogenicity, immunogenicity of secreted transgene H chain Ig carrying the two heterologous epitopes was analyzed by direct intraspleen inoculation of plasmid γ1NV²NA³ and by comparing the antibody response in these mice to that of mice inoculated with plasmid γ1NANP. All mice mounted a humoral antibody response to the human constant region of the transgene product proving that immunization took place. Mice of both groups produced anti-(NANP)3 antibodies, indicating that in both instances, the CDR3 loops were immunogenic (FIG. 17). However, the anti-NANP response in mice inoculated with plasmid γ1NV²NA³ was higher than in mice inoculated with plasmid γ1NANP (FIG. 17A versus 17B). Interestingly, whereas mice inoculated with plasmid γ1NV²NA³ produced antibodies reactive against both (NANP)3 and NANPNVDPNANP peptides (FIGS. 17B and 17D), mice inoculated with plasmid γ1NANP produced antibodies against (NANP)3 only (FIGS. 17A and 17C). Because antibodies to (NANP)3 do not cross-react with NANPNVDPNANP, mice inoculated with plasmid γ1NV²NA³ produced two distinct populations of antibodies, one against the (NANP)3 peptide in CDR3 and the other against the NANPNVDPNANP peptide in CDR2.

These results demonstrate that the two engineered CDRs were independently immunogenic in vivo and that the presence of the Th cell determinant in CDR2 enhanced the production of antibodies against the B cell epitope in CDR3.

EXAMPLE V

Durable Immunity and Immunologic Memory to a Parasite Antigen Induced by Somatic Transgene Immunization This example shows that inoculation of plasmid DNA carrying an immunoglobulin heavy chain gene under the control of tissue-specific regulatory elements leads to immunity and persistent immunologic memory against a peptide epitope.

The protocols used are described below (Gerloni et al., Vaccine 16:293-297 (1998)).

Eight week old C57Bl/6 (H-2$^b$) female mice were purchased from the Jackson Laboratories (Bar Harbor, Me.). Mice were maintained in the animal facility of the University of California, San Diego, throughout the duration of the experiments. Plasmid γNANP (Sollazzo et al., supra, 1990a) and the γ1NANP protein were prepared as in Example I and III.

Mice were inoculated with 100 µg of plasmid DNA per injection. Five basic routes of inoculation were used. These are described under Example I.

Mice were immunized with affinity-purified γ1NANP protein (50 µg per mouse) either emulsified in complete Freunds' adjuvant (CFA), subcutaneously, or adsorbed onto alum, intraperitoneally. The booster immunizations consisted of a single injection of γ1NANP protein (50 µg/mouse) emulsified in incomplete Freunds' adjuvant (IFA), subcutaneously. The times of booster are as indicated in the text and in the legend to FIG. 14. Antibodies to intact γ1NANP protein (NANP)$_n$ were detected by ELISA as in Example II.

Figure 13:
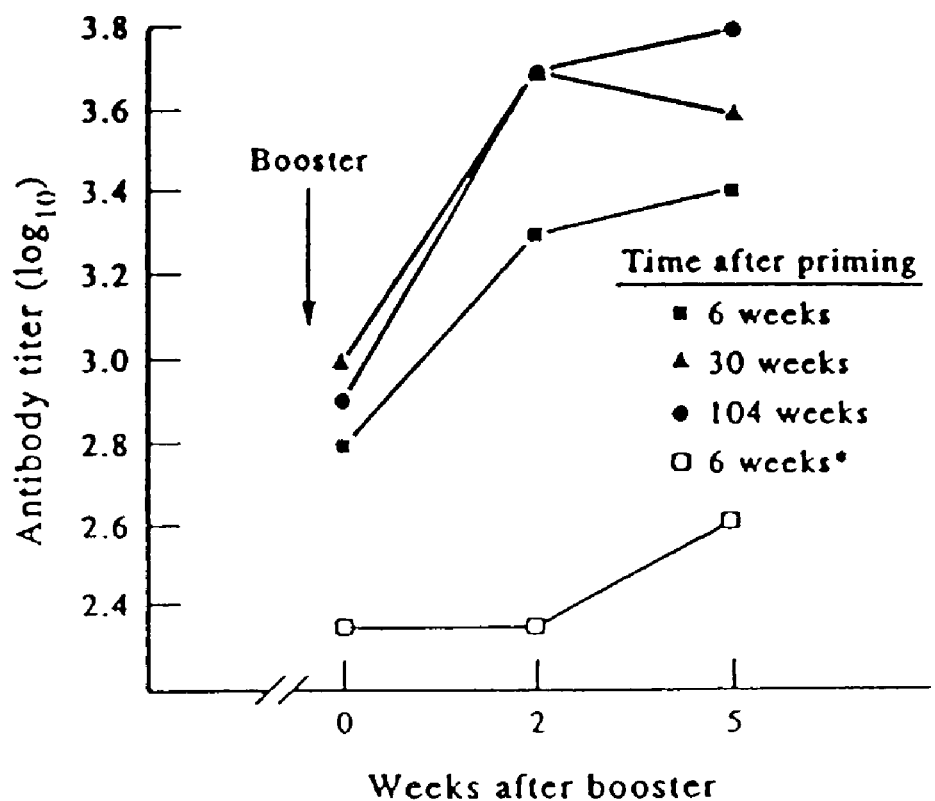
FIG. 13 shows a comparison of the primary antibody response in mice following inoculation with plasmid γ1NANP DNA, or with γ1NANP protein in immunologic adjuvants. Each group of mice consisted of four animals. Mice given γ1NANP DNA were inoculated intraspleen. Mice given γ1NANP protein in alum were injected intraperitoneally. Antibody titers against NANP peptide were measured 6 weeks after inoculation. (Time 0 refers to pre-inoculation bleed.) Data shown represent the mean of individual titers which were determined on the basis of the last value with an absorbance $\geq$ of 0.200 ($A_{492}$).

The immunity induced via STI was compared to conventional immunity using immunologic adjuvants. Immunoglobulins possess unique antigenic determinants clustered primarily in or around the CDRs (Rudikoff, Cont. Top. Mol. Immunol. 9:169-208 (1983); Billetta and Zanetti, Int. Rev. Immunol. 10:251-263 (1993)). The results represented in FIG. 9 show the development of the primary antibody response directed against the (NANP)3 amino acid sequence expressed in the CDR3 of the transgene H chain. Anti-NANP antibodies became detectable by the second week and increased through week 6. No binding to the (NANP)n peptide was detected in mice inoculated with plasmid control pSVneo. The anti-NANP antibody response induced through STI was compared to that elicited by immunization with the γ1NANP protein administered in immunologic adjuvants. As shown in FIG. 13, at week 6, the antibody titer measured in mice inoculated with DNA was higher than that in mice immunized with γ1NANP protein in CFA or in alum, respectively.

Figure 14:
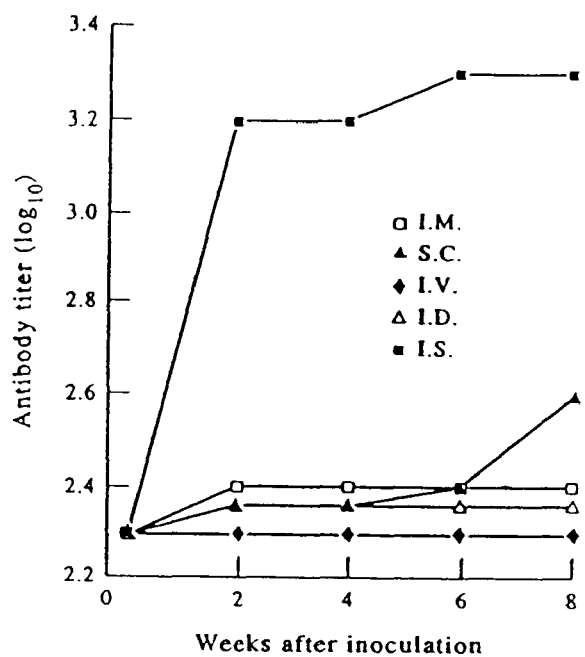
FIG. 14 shows secondary immune response at various time intervals after priming with plasmid γ1NANP DNA inoculated intraspleen. All mice were primed intraspleen with plasmid γ1NANP DNA or control plasmid pSVneo (*) and were boosted s.c. by injection of the γ1NANP protein emulsified in IFA at different times (6-30-104 weeks) after priming. Antibody titers against the NANP peptide were determined 2 and 5 weeks after booster. Among the plasmid γ1NANP DNA primed mice, ten were boosted after 6 weeks, six were boosted after 30 weeks, and four were boosted after 104 weeks, respectively. Four control mice primed with pSVneo DNA (*) were boosted after 6 weeks. Data shown represent the mean of individual titers which were determined on the basis of the last value with an absorbance $\geq$ of 0.200 ($A_{492}$).

STI induced long-lasting immunologic memory. Immunologic memory was tested by investigating the ability of primed mice to respond to a single booster dose of γ1NANP protein in IFA given subcutaneously 6, 30 or 104 weeks after the DNA inoculum. The anamnestic response against the NANP epitope was measured 2 and 5 weeks after booster. As shown in FIG. 14, a specific anamnestic response occurred at all three time points after priming. NANP-reactive antibodies are still detectable after two years from priming. The booster effect was weaker in mice boosted at 6 weeks than in mice boosted at later times. In mice boosted on week 30, circulating antibodies persisted at a high titer ($Log_{10}$ 3.5) for at least an additional 17 months. The booster response was specific since mice inoculated at the time of priming with plasmid DNA pSVneo had a much lower antibody titer. Booster with plasmid DNA intravenously did not yield any memory response.

These results demonstrate administration of a nucleic acid molecule results in persistent immunologic memory up to 2 years.

EXAMPLE VI

DNA Immunization in relB-Deficient Mice Discloses a Role for Dendritic Cells in IgM to IgG1 Switch In Vivo This example describes the role of dendritic cells in the IgM to IgG switch in vivo.

The protocols are described below (Gerloni et al., Eur. J. Immunol. 28:516-524 (1998)).

Eight to ten week old C57BL/6 mice were purchased from the Jackson Laboratories (Bar Harbor Me.) and were kept in the animal facility of the University of California, San Diego. The generation of relB (−/−) and hemizygous (−/+) mice was described previously (Lo et al., supra, 1992). Bone marrow chimeras were constructed using as recipients irradiated (1000R) C57Bl/6J injected with $7 \times 10^6$ bone marrow cells from relB (−/−) or (−/+) mice (Burkly et al. supra, 1995). Inoculation with plasmid DNA was performed eight weeks after bone marrow transfer.

γ1NANP is described in Example I. In plasmid DNA γ1NANP/GM-CSF, the murine GM-CSF coding sequence from plasmid p3159 was cloned at the 3' end of the CH3 domain through a Gly-Gly linker (Tao et al., supra, 1993). In plasmid DNA γ1NANP/IL-2, the murine IL-2 coding sequence from plasmid p3163 was similarly cloned at the 3' end of the CH3 domain. Plasmids DNA were prepared from DH5γ Escherichia coli according to procedures (Sambrook et al., supra, 1989) as detailed in Example I.

The recombinant antibody γ1NANP was produced and purified as described previously (Sollazzo et al., supra, 1989); Billetta and Zanetti, supra, 1992).

Mice were inoculated intraspleen with 100 γg of plasmid DNA in 30 μl of sterile saline solution as described in Example I. Booster injections (C57Bl/6 mice only) were administered on day 35 by a single subcutaneous injection (50 μg per mouse) of affinity-purified γ1NANP protein emulsified in incomplete Freunds' adjuvant.

Antibodies to the intact γ1NANP protein were detected by enzyme-linked immunosorbent assay (ELISA) as in Example II. The isotype of antibodies was determined using rabbit antibodies specific for the various murine Ig classes (Mouse Typer Sub-isotyping kit; Bio-Rad; Hercules, Calif.) as in Example III.

Figure 19:
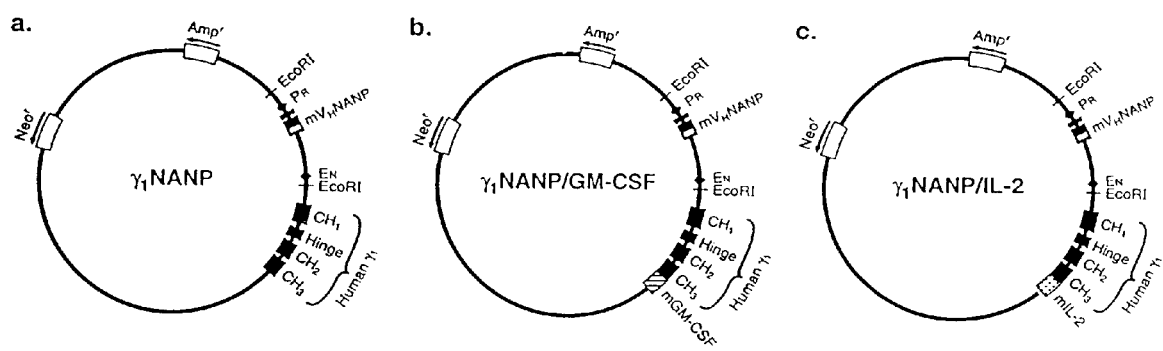
FIG. 19 shows a schematic representation of plasmid DNA γ1NANP, γ1NANP/GM-CSF and γ1NANP/IL-2. Panel A shows γ1NANP is a variant of γ1WT, the product of the fusion between a human γ1 C region gene present in the plasmid vector pNeoγ1 with murine $V_H^{62}$ gene (2.3 kb) (Sollazzo et al., supra, 1989). In this productively rearranged $V_H$ region gene, the CDR3 was modified to code for three repeats of the Asn-Ala-Asn-Pro (NANP) sequence (Sollazzo et al., supra, 1990a). The C region gene is in genomic configuration. Panel B shows that, in plasmid DNA γ1NANP/GM-CSF (granulocyte monocyte-colony stimulating factor), the murine GM-CSF coding sequence was cloned at the 3' end of the CH3 domain. Panel C shows that, in plasmid DNA γ1NANP/IL-2, the murine IL-2 coding sequence was similarly cloned at the 3' end of the CH3 domain. Each plasmid DNA carries the regulatory elements, promoter (Pr) and enhancer (En) needed for tissue-specific expression. Neo$^r$=neomycin and Amp$^r$=ampicillin, are the resistance genes.

A GM-CSF chimeric gene induced isotype switch. STI was induced using plasmid DNA γ1NANP coding for an Ig H chain gene in which the 3' end of the CH3 domain of the human constant region gene was chimerized in one case with murine GM-CSF and in another case with IL-2 cDNA (FIG. 19). GM-CSF has been shown to augment the immunogenicity of tumor cell (Dranoff et al., Proc. Natl. Acad. Sci. USA 90:3539-3543 (1993); Levitsky et al. J. Immunol. 156:3858-3865 (1996)) and DNA (Xiang and Ertl, supra, 1995) vaccines possibly through its action on DC (Inaba et al., J. Exp. Med. 176:1693-1702 (1992)). It has been reported that immunization with tumor-derived idiotype/GM-CSF fusion protein induces a potent anti-idiotype response (Tao et al. supra, 1993), and inoculation with an idiotype/GM-CSF chimeric gene protects against B-cell lymphoma in mice (Syrengelas et al., Nat. Med. 2:1038-1041 (1996)). IL-2 is required for growth of T cells and is a cofactor in activating B cells to secrete Ig (Smith, Science 240:1169-1176 (1988)).

Figure 20:
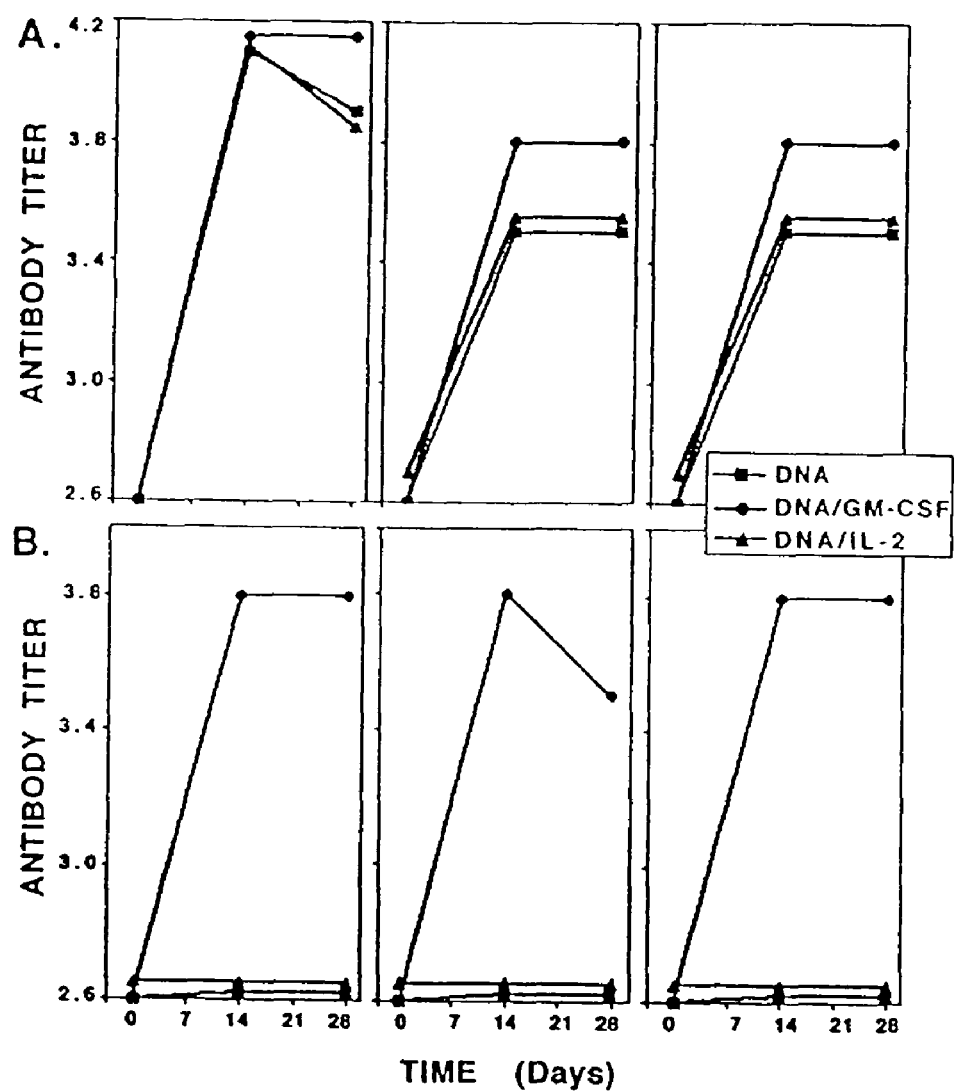
FIG. 20 shows the titer of total (Panel A) and IgG1 (Panel B) antibodies against TgIg in mice during STI induced with plasmid DNAs γ1NANP, γ1NANP/GM-CSF or γ1NANP/IL-2 (primary response). Each panel represents an independent experiment. The left panels show values of pooled sera from 6 mice, while center and right panels refer to values of pooled sera from 4 mice each. Antibody titers were determined on the basis of the last dilution with an absorbance (A492) ≧ of 0.200. Tests were done in duplicate.
Figure 21:
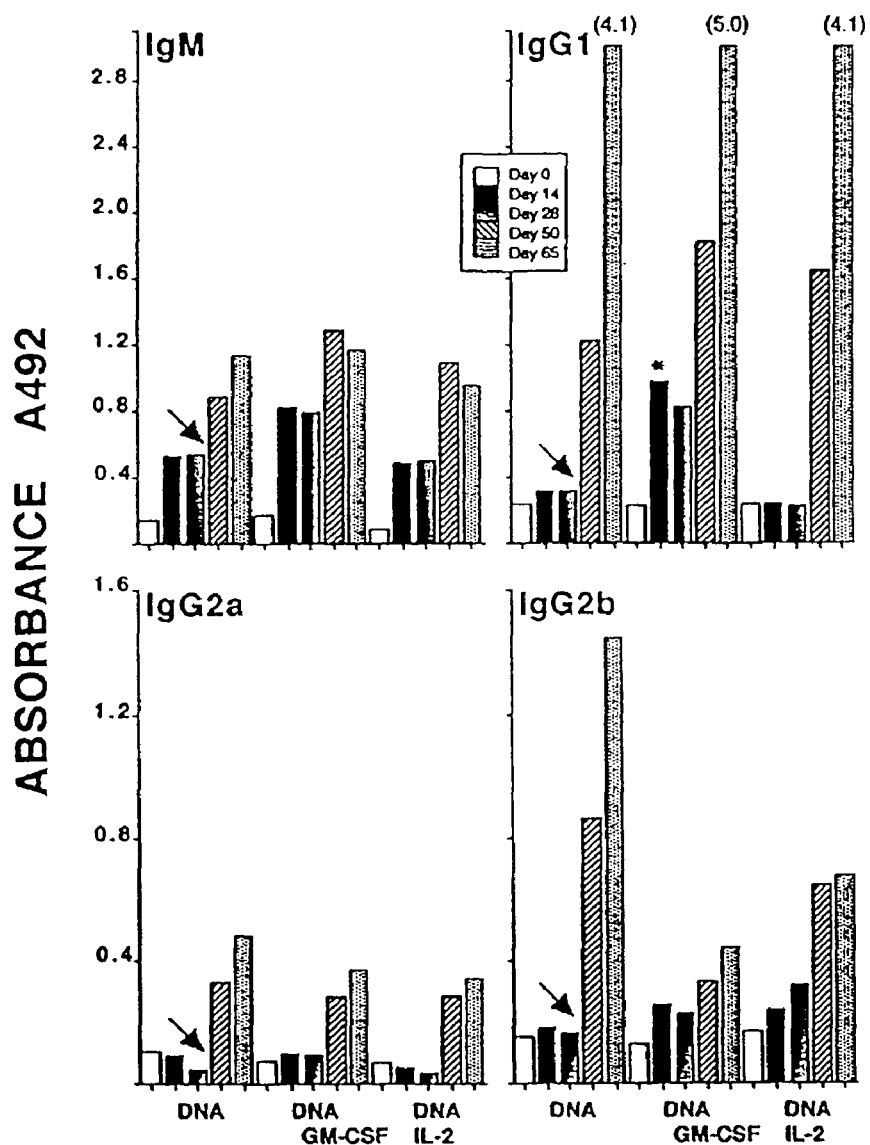
FIG. 21 shows isotype class determination of anti-TgIg antibodies in mice inoculated with plasmid DNAs γ1NANP, γ1NANP/GM-CSF or γ1NANP/IL-2. Values refer to a pool of six mice from one out of the three independent experiments shown in FIG. (29) 19. Mice were bled at the times indicated. The arrow indicates booster immunization (day 35). The asterisk identifies the elevated IgG1 binding induced by DNA/GM-CSF. GM-CSF augmented the titer of IgG1 antibodies during the secondary response (Log titer 5.0 vs. 4.1). Values are expressed as absorbance (A492). IgM, IgG1 and IgG2b were measured on sera diluted 1:1,600; IgG2a were measured on sera diluted 1:400. Tests were done in duplicate.

In three independent experiments, inoculation with DNA/GM-CSF, but not DNA/IL-2, yielded a primary antibody response against TgIg of slightly greater magnitude than in mice inoculated with γ1NANP DNA (FIG. 20A). Mice inoculated with DNA/GM-CSF produced IgG1 antibodies against TgIg readily after priming (FIG. 20B). As described in Example I, booster injection with antigenized antibody in Freunds' adjuvant induced an IgG1 response, indicating that intraspleen inoculation of DNA does not hamper the class switch machinery. Thus, the effect observed with inoculation of DNA/GM-CSF can be attributed to a function mediated by GM-CSF. GM-CSF did not have any detectable effect on IgG2a antibodies but did modify the IgG2b response after booster immunization (FIG. 21) in that it prevented the elevation of antibodies of this isotype upon booster. Since a similar effect was noted in mice receiving the DNA/IL-2, it is possible that down-regulation of IgG2b antibodies is not specific for GM-CSF. Mice inoculated with DNA/GM-CSF produced the highest titer of IgG1 antibodies (FIG. 21). These results indicate that inoculation of plasmid DNA containing an Ig H chain gene chimerized with the GM-CSF gene promoted IgM→IgG1 switch in vivo.

A lack of isotype switch was observed in relB (−/−) mice. Failure to produce IgG1 following inoculation with γ1NANP DNA indicated that neither B cells nor DC presented TgIg peptides to T cells in immunogenic form sufficient to promote secretion of IL-4 and other cytokines required to drive switch to IgG1. Resting B cells are unable to activate naive T cells in vivo due to poor co-stimulation (Fuchs and Matzinger, Science 258:1156-1159 (1992); Ronchese and Hausmann, J. Exp. Med. 177:679-690 (1993)). Moreover, B lymphocytes lack specific receptor(s) for GM-CSF, hence making it difficult to attribute the effect of the DNA/GM-CSF on the IgM to IgG1 switch to activation of B cells by GM-CSF. On the other hand, GM-CSF is known to enhance both viability and function of DC (Heufler et al., J. Exp. Med. 167:700-705 (1988); Witmer et al., J. Exp. Med. 166:1484-1498 (1987)), activate cells of the dendritic lineage in vitro (Inaba et al., supra, 1992; Caux et al., Nature 360:258-261 (1992); Scheicher et al., J. Immunol. Methods 154:253-264 (1992); Sallusto and Lanzavecchia, J. Exp. Med. 179:1109-1118 (1994)), and potentiate antigen presentation in vivo (Jones et al., Eur. J. Clin. Microbiol. Infect. Dis. S47-53 (1994); Disis et al., Blood 88:202-210 (1996)). The role of DC in the IgM to IgG1 switch was tested using mice carrying a mutation in the relB subunit of the NF-γB complex which lack bone-marrow derived mature DC (Burkly et al., Nature 373:531-536 (1995)).

Mice carrying the relB mutation (−/−) were generated as previously described (Burkly et al., supra, 1995) and have a number of defects associated with mature dendritic cell function. First, spleen cells from relB mutant mice show a very poor ability to stimulate T cells in both allogeneic responses and peptide specific responses (Burkly et al., supra, 1995). Second, negative selection of autoreactive T cells in the thymus is impaired (Laufer et al., Nature 383:81-85 (1996); DeKoning et al., J. Immunol. 158:2588-2566 (1997)). Third, secondary lymphoid tissues fail to develop in mutant mice (Burkly et al., supra, 1995; Lo et al., Am. J. Pathol. 141:1237-1246 (1992), a feature in part attributed to the absence of mature interdigitating dendritic cells (IDC) that help organize lymphoid tissues. However, antigen presenting function is not entirely absent as T cell and antibody responses can be generated in vivo against influenza virus infection (Burkly et al., supra, 1995). This residual antigen presenting function is possibly due to macrophages, B lymphocytes, or dendritic cell precursors. Thus, relB mutant mice constitute an ideal model system to test the role of DC in isotype switch during STI.

Figure 22:
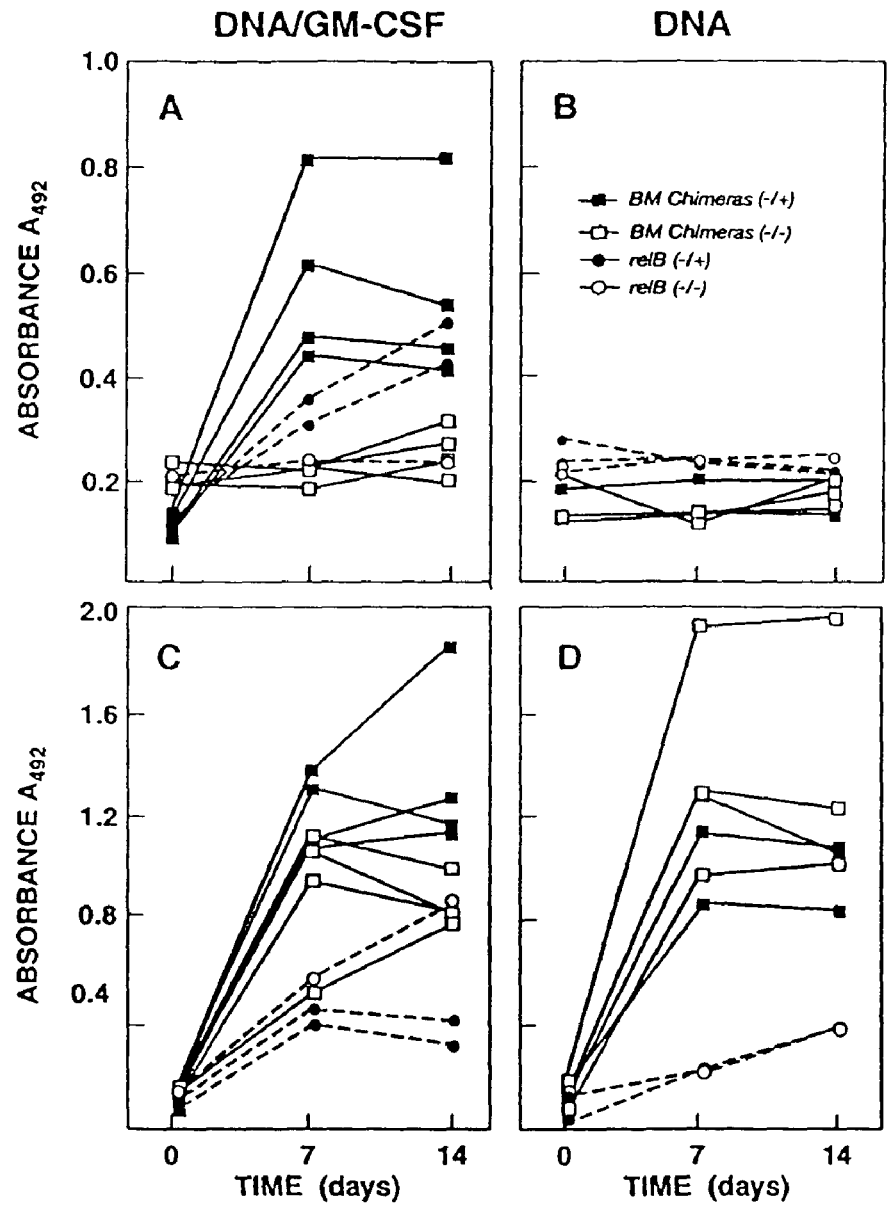
FIG. 22 shows IgG1 and IgM anti-TgIg antibodies in bone marrow chimeras, relB mutants (−/−) and hemizygous (−/+) mice following inoculation with plasmid DNA/GM-CSF or γ1NANP DNA. Eight weeks after reconstitution, bone marrow chimeric mice were inoculated with DNA/GM-CSF (Panels A and C) or with DNA (Panels B and D). IgG1 (Panels A and B) and IgM (Panels C and D) antibodies were monitored. Sera were tested at 1:400 dilution. Symbols identify the following groups: bone marrow chimeras (−/+) (black box); bone marrow chimeras (−/−) (open boxes); relB hemizygotes (−/+) (black circles); and relB mutants (−/−) (open circles). Values shown refer to single mice. Tests were done in duplicate.

STI was induced in relB homozygous mutants (−/−) or hemizygotes (−/+) and in bone-marrow chimeras constructed using mutant bone marrow donors and irradiated normal C57Bl/6 recipients. As seen previously, bone marrow chimeric mice have a less severe form of the mutant syndrome while retaining the impaired antigen-presenting function and immune responsiveness of the homozygous relB (−/−) mutant mice (Burkly et al., supra, 1995). Moreover, in these mice, germinal center formation appears to be normal and FDC are detected with normal distribution. By comparing the outcome of STI induced with DNA/GM-CSF to that induced with γ1NANP DNA, it is possible to determine if DC play any role in the IgM to IgG1 switch. Neither (−/−) bone marrow chimeras nor relB mutant produced IgG1 antibodies following inoculation with DNA/GM-CSF (FIG. 22A). In contrast, all (−/+) bone marrow chimeras and hemizygous (−/+) mice produced IgG1 antibodies as seen in normal C57Bl/6 mice. Not surprisingly, none of the mice inoculated with γ1NANP DNA produced IgG1 antibodies (FIG. 22B). All bone marrow chimeras, relB mutants (−/−) and hemizygotes (−/+) produced IgM antibodies after inoculation with either DNA/GM-CSF or γ1NANP DNA (FIGS. 22C and 22D), confirming that they were immunized and ruling out a possible bias introduced by the bone marrow transfer. The immune response in the relB mutants and hemizygous mice was generally lower than that detected in bone marrow chimeras but its significance is not clear. Thus, in the absence of DC the effect of GM-CSF on the IgM to IgG1 switch was abrogated.

These results demonstrate that administration of a nucleic acid molecule encoding an epitope fused to GM-CSF promotes the IgM to IgG switch.

EXAMPLE VII

Immunological Memory after Somatic Transgene Immunization is Positively Affected by Priming with GM-CSF and Does Not Require Bone Marrow-Derived Dendritic Cells This example describes enhanced immunological memory when an administered nucleic acid molecule is primed with GM-CSF.

The protocols used are described below (Gerloni et al., Eur. J. Immunol. 28:1832-1838 (1998)).

Eight to ten week old C57BL/6 mice were purchased from the Jackson Laboratories (Bar Harbor Me.) and were kept in the animal facility of the University of California, San Diego. Bone marrow chimeras were constructed by injecting $7 \times 10^6$ bone marrow cells from relB (−/−) (Lo et al., supra, 1992) or hemizygous (−/+) mice as donors into irradiated (1100R) C57BL/6J recipients as described (Burkly et al., supra, 1995). Mice were bred and kept in the animal facility of the Scripps Research Institute. Inoculation with plasmid DNA was performed eight weeks after bone marrow transfer.

The construction and purification of plasmids γ1NANP (DNA) and γ1NANP/GM-CSF (DNA/GM-CSF) were generated as described previously in Example VI. Purified plasmids were stored at −20° C. until use. Engineered antibody γ1NANP was produced and purified as described previously (Sollazzo et al., supra, 1989; Billetta and Zanetti, supra, 1992). A synthetic peptide containing multiple (>10) repeats of the NANP sequence, (NANP)n, was the kind gift of Dr. A. Verdini (Monterotondo, Italy). Peptide DENGNYPLQC of the human invariant chain served as control.

DNA vaccination consisted of a single intrasplenic inoculation of 100 µg of plasmid DNA in 30 µl of sterile saline solution as described in Example I. Mice immunized with the affinity-purified γ1NANP protein received a subcutaneous injection of the protein (50 µg/mouse) in complete Freunds' adjuvant (CFA). Booster injections consisted of either a single subcutaneous injection of affinity-purified γ1NANP protein (50 µg per mouse) emulsified in incomplete Freunds' adjuvant (IFA), or $10^5$ irradiated P. falciparum sporozoites injected intraperitoneally in a 0.4 ml of Dulbecco minimal essential medium. Sporozoites were produced in Anopheles freeborni mosquitos infected as described (Wirtz et al., supra, 1987).

Antibodies to synthetic peptide (NANP)n and γ1NANP were done as in Example II. The isotype of antibodies was determined using goat antibodies specific for the murine IgM and IgG1 classes (Caltag; San Francisco Calif.) (see Example III).

Figure 23:
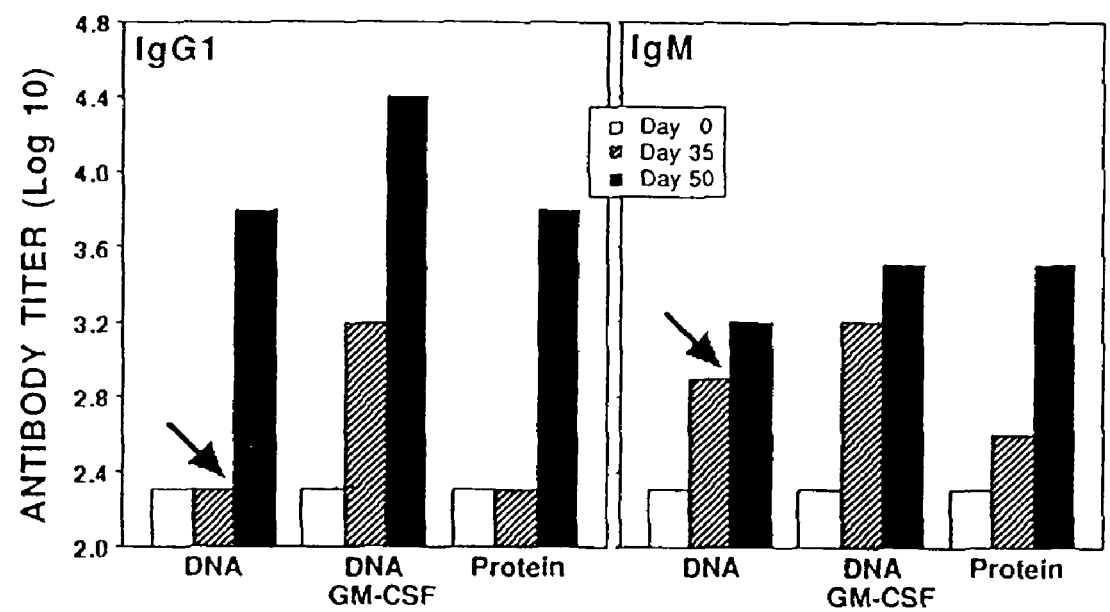
FIG. 23 shows GM-CSF heightens the anamnestic anti-NANP antibody response following booster immunization with antigenized antibody γ1NANP. Columns refer to antibody titers (Log 10) were measured on (NANP)n peptide. Experimental groups are identified at the bottom. The arrow indicates the time (day 35) when the booster immunization was given. Values refer to binding of a pool of sera collected at the same time. Each group consisted of four mice.

GM-CSF heightens the anamnestic response induced by antigenized antibody in IFA. The anti-NANP response was measured in mice primed with DNA/GM-CSF or DNA and subsequently boosted with antigenized antibody γ1NANP in IFA. Inoculation of DNA/GM-CSF but not DNA induced IgG1 antibodies during the primary response (see Example VI). A booster injection with antibody γ1NANP in IFA increased the IgG1 titer in DNA/GM-CSF primed mice and promoted the de novo synthesis of IgG1 antibodies in mice primed with DNA alone (FIG. 23, left panel). In two independent experiments, the antibody titer was on average 4 fold higher (4.1-4.4 vs 3.5-3.8) in mice primed with DNA/GM-CSF than in mice primed with DNA alone (Table 8). Interestingly, the antibody titer measured in mice primed with DNA/GM-CSF was also higher than that of control mice primed and boosted with antigenized antibody γ1NANP in Freunds' adjuvant (FIG. 23, left panel). The titer of IgM antibodies was similar in all groups whether GM-CSF had been used or not (FIG. 23, right panel).

Figure 25:
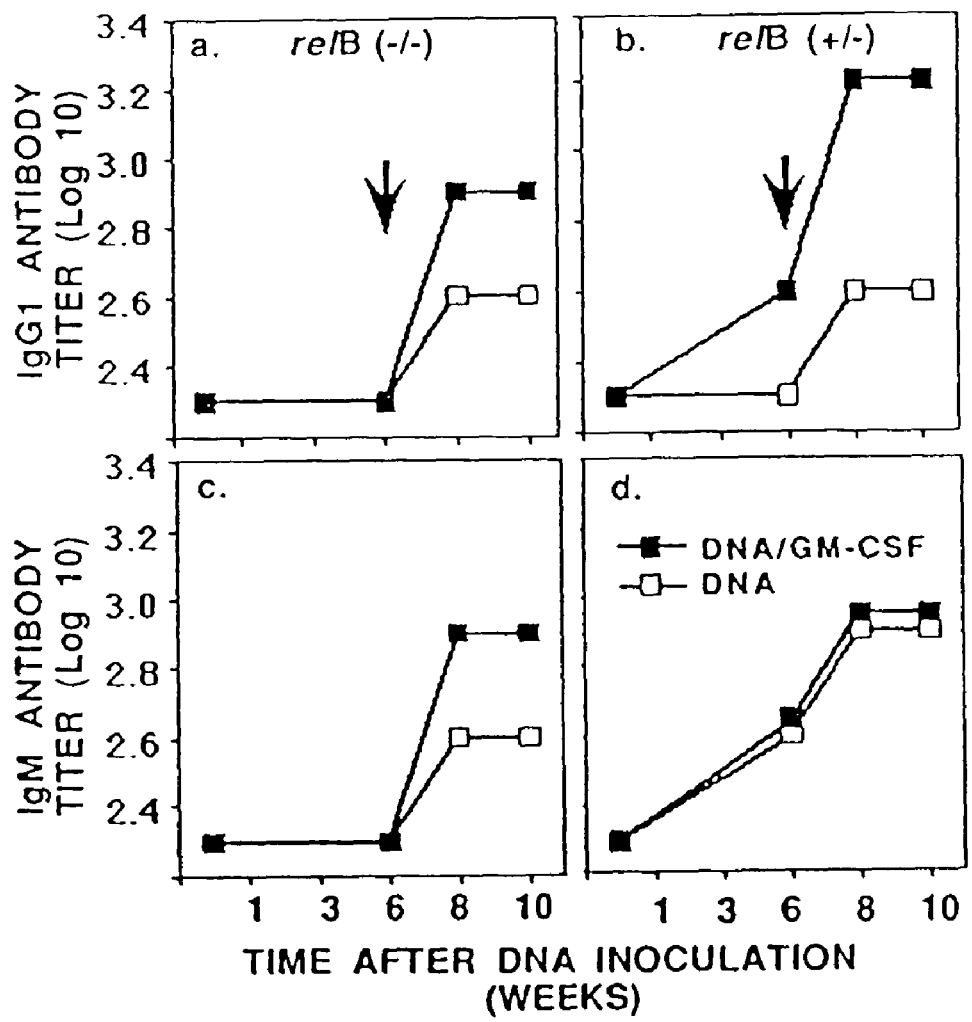
FIG. 25 shows GM-CSF heightens the anamnestic anti-NANP antibody response following booster immunization with antigenized antibody γ1NANP in relB (−/−) mice. Antibody titers (Log 10) were measured on (NANP)n peptide. Mice were primed by inoculation of DNA (open squares) or DNA/GM-CSF (closed squares) as indicated. The arrow indicates the time (day 42) of the booster immunization with γ1NANP antibody. Values refer to binding of a pool of sera collected at the same time. Each group consisted of four mice. Tests were done in duplicate and repeated at least there times.

IgM component, with titers proportionally higher in mice primed with DNA/GM-CSF (FIG. 25). The antibody response in relB (−/+) chimeras was comparable to that generated in adult immunocompetent C57BL/6 mice. During priming, relB (−/−) chimeras did not develop anti-NANP antibodies, irrespective of the type of DNA used for immu-

TABLE 8

Ig G1 responses in mice primed with DNA/GM-CSF and boosted with antigenized antibody protein.

| Experiment No.[a] | Well coating | Primary response Immunogen | | | Secondary response Immunogen | | |
|---|---|---|---|---|---|---|---|
| | | DNA | DNA/GM-CSF | Enhancement (fold) | DNA | DNA/GM-CSF | Enhancement (fold) |
| 1 | NANPn | <200 (2.3) | 1.600 (3.2) | 8 | 3.200 (3.5) | 12.800 (4.1) | 4 |
| 2 | | <200[b] (2.3) | 1.600 (3.2) | 8 | 6.400 (3.8) | 25.600 (4.4) | 4 |
| 1 | γNANP | <200 (2.3) | 12.800 (4.1) | 64 | 102.400 (5.0) | 409.600 (5.6) | 4 |
| 2 | | <200 (2.3) | 6.400 (3.8) | 32 | 51.200 (4.7) | 204.800 (5.3) | 4 |

[a]The two experiments represented were run independently. Each group consisted of four mice. Priming was performed by a single intrasplenic inoculation of DNA or DNA/GM-CSF. The booster immunization was given at day 35 with γ1NANP antibody in IFA. Pooled sera were tested against the synthetic peptide (NANP)n or the whole antigenized antibody as indicated.
[b]Values refer to antibody titers expressed as reciprocal of the last positive dilution. In parentheses are indicated the corresponding log 10 titers.

Figure 24:
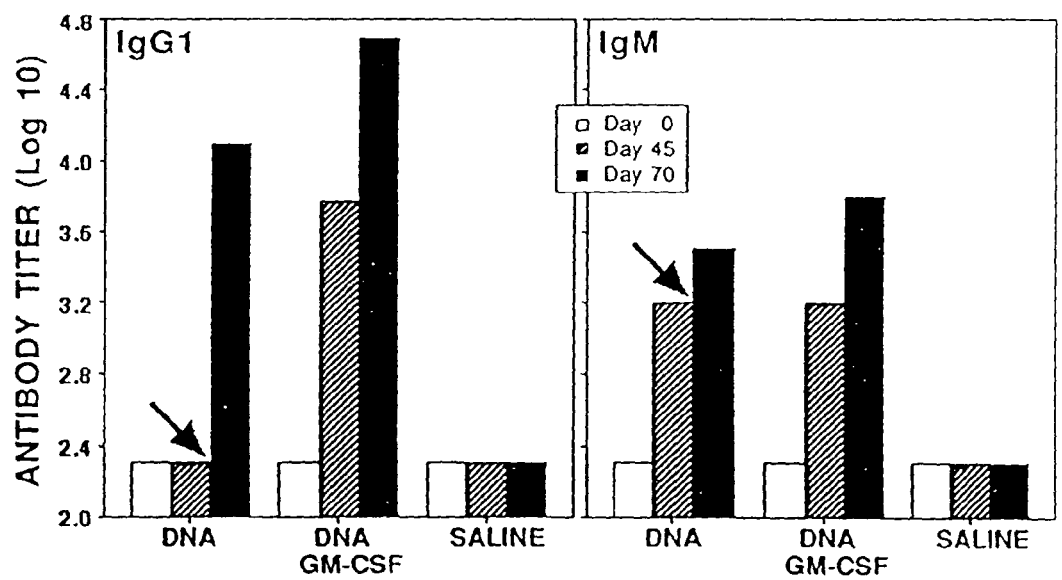
FIG. 24 shows GM-CSF heightens the anamnestic anti-NANP antibody response following booster immunization with *P. falciparum* sporozoites. Columns refer to antibody titers (Log 10) were measured on (NANP)n peptide. Experimental groups are identified at the bottom. The arrow indicates the time (day 45) when the booster immunization was given. Values refer to binding of a pool of sera collected at the same time. Each group consisted of four mice.

GM-CSF heightens the anamnestic response induced by injection of *P. falciparum* sporozoites. Mice primed by inoculation of plasmid DNA respond to a booster immunization by *P. falciparum* sporozoites with a typical secondary response (see Example III). This was determined to be immunologically relevant since booster by parasites is equivalent to a challenge response or restimulation by infection. Booster by parasites yielded 4 fold higher IgG1 anti-NANP antibody titers in mice primed with DNA/GM-CSF as compared with mice primed with DNA only (Log 4.7 vs. 4.1) (FIG. 24, left panel). No antibodies were detected in mice primed with saline and boosted with sporozoites (negative controls). The effect on IgM antibodies was minimal (FIG. 24, right panel). This experiment confirms, therefore, that GM-CSF given during priming heightens the IgG1 memory response irrespective of the composition of the antigen used in the booster immunization.

GM-CSF heightens the anamnestic response in mice lacking bone marrow-derived dendritic cells. The role of bone marrow derived DC (interdigitating dendritic cells, IDC) in the enhancement of memory IgG1 antibodies was studied in mice carrying the relB (−/−) mutation. These mice lack mature IDC and carry a number of defects associated with mature dendritic cell function, including failure to develop secondary lymphoid tissues (Lo et al., supra, 1992; Burkly et al., supra, 1995). As disclosed in Example VI, relB (−/−) mice or relB (−/−) chimeras inoculated with DNA/GM-CSF do not produce IgG1 antibodies. The present experiments were performed with relB (−/−) chimeras only since these mice are more resistant and have a less severe form of the mutant syndrome while retaining the impaired antigen-presenting function of the homozygous relB (−/−) mutant mice (Burkly et al., supra, 1995). In relB (−/−) chimeras, antibody 33D1-reactive IDC are within relatively normal number (Crowley and Lo, in Targeted gene knockouts: insights into dendritic cell biology, Academic Press, London (1998)) but are functionally inactive (DeKoning et al., supra, 1997). Germinal center FDC, which are of host origin, are detected with normal distribution (see Example VI). RelB (−/+) chimeras served as controls.

Figure 26:
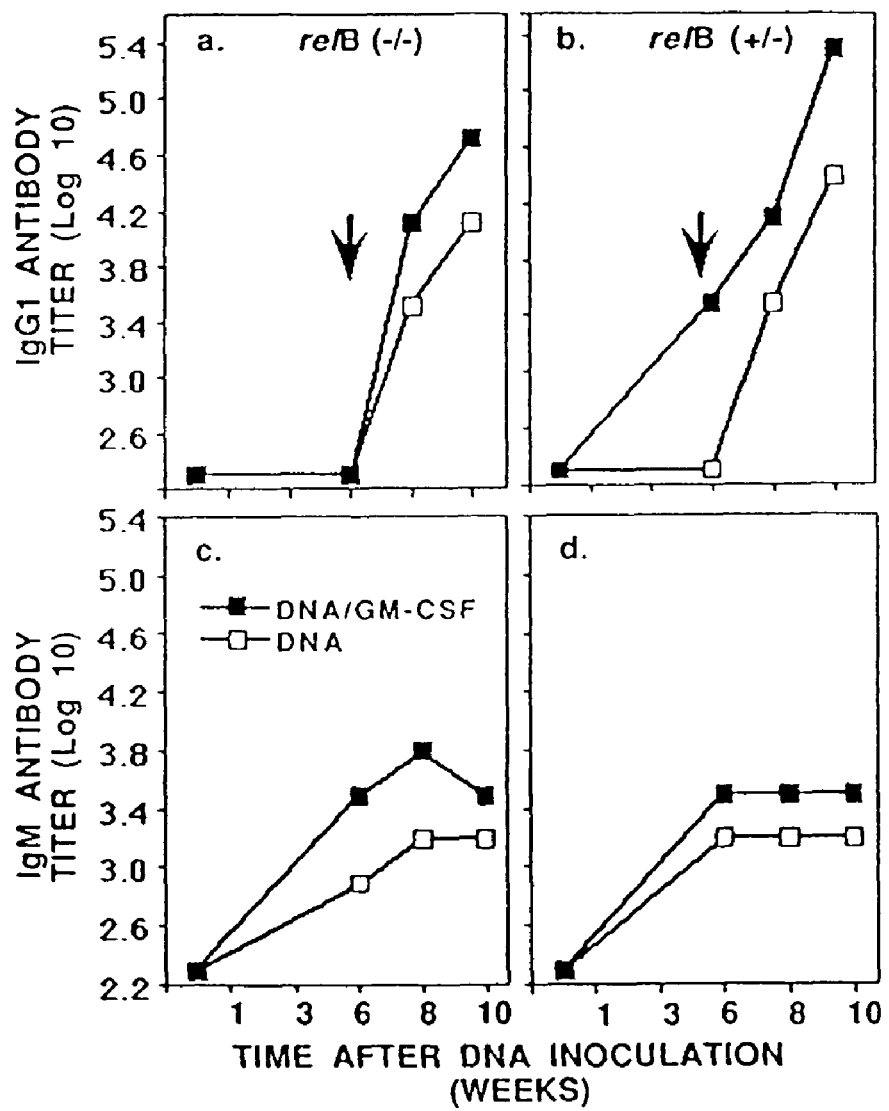
FIG. 26 shows relB (−/−) mice produce IgM antibodies against the whole TgIg following priming with DNA. Antibody titers (Log 10) were measured on γ1NANP antibody. Mice were primed by inoculation of DNA (open squares) or DNA/GM-CSF (closed squares) as indicated. The arrow indicates the time (day 42) of the booster immunization with γ1NANP antibody. Values refer to binding of a pool of sera collected at the same time. Each group consisted of four mice. Tests were done in duplicate and repeated at least there times.

After booster with antigenized antibody γ1NANP in IFA, the anti-NANP response rose sharply, both in the IgG1 and nization or the immunoglobulin isotype considered (FIG. 25, Panels A and C). However, lack of primary response in relB (−/−) chimeras was not due to absence of immune responsiveness since these mice produced IgM antibodies against the whole TgIg (FIG. 26, panel C). It appears, therefore, that the enhancing effect of GM-CSF on the anamnestic response can not be attributed to a summation effect since, as indicated by the relB (−/−) chimeras, enhancement occurs after booster even though no antibodies are produced during the primary response (FIG. 25, panel A; FIG. 26, panel A).

These results demonstrate that inclusion of the cytokine GM-CSF enhances the immune response to a B cell epitope administered as a nucleic acid encoding the epitope. The results also indicate that GM-CSF functions as a modulator of the immune response and immunological memory.

EXAMPLE VIII

Activation of CD4 T Cells by Somatic Transgenesis Induces Generalized Immunity of Uncommitted T Cells and Immunologic Memory This example describes the activation of CD4 T cells with administration of a nucleic acid molecule encoding an epitope.

The protocols used are described below (Gerloni et al., J. Immunol. 162:3782-3789 (1999)).

Eight to ten week old C57BL/6 mice were purchased from the Jackson Laboratories (Bar Harbor Me.) and were kept in the animal facility of the University of California, San Diego.

Plasmids γ1NV$^2$NA$^3$ and γ1NANP were engineered as described in Example IV and Sollazzo et al., supra, 1990a, respectively. pSV2Neo is the original plasmid forming the backbone of the pNeog1 vector without the human γ1 C region gene. Plasmid DNAs were purified using a Qiagen MEGAPREP kit (Qiagen, Chatsworth, Calif.). This plasmid was used as a control in the immunization experiments. The purity of the DNA was monitored using the following equation: % N=(11.1R−6.32)/(2.16−R) where R=260 nm/280 nm, % N=% of Nucleic Acid. Purified plasmids were stored at −20 γC until use.

Recombinant antigenized antibodies γ1NV²NA³ and γ1NANP were produced in transfectoma cells and purified as described in Example IV (Sollazzo et al., supra, 1990a). Synthetic peptides NANPNANPNANP and NANPNVDPNANP were synthesized in the Peptide Chemistry Core Facility of the University of California, San Diego.

Mice were inoculated intraspleen with 100 γg of plasmid DNA in 50 μl of sterile saline solution as previously described in Example I. Booster injections were administered on day 90, 110, 120 and 150 after priming by a single subcutaneous injection (50 μg per mouse) of affinity-purified γ1NV²NA³ antibody emulsified in incomplete Freunds' adjuvant (IFA).

After animals were inoculated, at the time of harvest, mice were sacrificed and the lymph nodes and spleens removed, and crushed in a tissue shredder to remove excess tissues and release cells. Single cell suspensions were treated with red blood cell lysis buffer (Sigma; St. Louis, Mo.) and cultured ($10^6$ cells/ml) in RPMI 1640 medium (Irvine Scientific; Santa Ana Calif.) supplemented with Hepes buffer, glutamine, 7.5% fetal calf serum and 50 μM 2-mercaptoethanol, in the presence or absence of synthetic peptides NANPNVDP-NANP or NANPNANPNANP (50 μg/ml) in triplicate. The cells were incubated at 37° C. in 10% $CO_2$ for 3 days. ($^3H$)-Thymidine was added at 1 μCi/well and the cells were incubated for 16-18 hours at 37° C. Cells were harvested onto glass fiber filter mats using a Tomtec cell harvester and the radioactivity was measured in a liquid scintillation counter (Betaplate; Wallac; Tuku Finland). Results are expressed as Stimulation Index (S.I.) calculated as the ratio of (counts per minute of cells cultured in the presence of synthetic peptide)/(counts per minute of cells cultured in the absence of peptide). Concanavalin A (ConA) stimulation was used as a polyclonal activator and positive control.

$CD4^+$ and $CD8^+$ T cells were isolated by antibody plus complement-mediated depletion from splenocytes of mice immunized 7 days earlier by DNA inoculation. Briefly, cell suspensions ($30 \times 10^6$ cells/ml) were treated with monoclonal antibody to CD8 (3.155) or CD4 (RL172) for 30 minutes on ice. After washing, anti-T cell antibodies were cross-linked with a mouse anti-rat (MAR 18.5) monoclonal antibody for 30 minutes on ice and rabbit complement was added twice for 30 minutes at 37° C. The cell suspension was then washed twice and resuspended at the concentration of $5 \times 10^6$ cells/ml in RPMI (Irvine Scientific). The purity of the separated cell fractions was assessed by analysis on a FACScan with Cellquest software (Becton & Dickinson, Mountain View, Calif.) at the Flow cytometry facility of The La Jolla Institute for Allergy and Immunology, using phycoerythrin (PE)-conjugated anti-CD4 and fluorescein isothiocyanate (FITC)-conjugated anti-CD8 monoclonal antibodies (Pharmingen, San Diego, Calif.).

Culture supernatants were harvested 40 hours after initial seeding and were stored at −20° C. The supernatants from three separate triplicate cultures were pooled for each mouse. IL-2 activity was determined in a bioassay utilizing the IL-2- and IL-4-dependent NK.3 cells in the presence of anti-IL4 (purified from the 11B11 cell line, ATCC). Briefly, 100 μl (1:2 dilution in medium) of 40 hour culture supernatants were added in duplicate to 100 μl of NK.3 cells ($10^6$/ml) and incubated for 36 hours. ($^3H$)-Thymidine was added at 1 μCi/well during the last 12 hours. Cells were harvested as specified above. Results are expressed as counts per minute.

IL-4, IL-5 and IFN-γ were measured in the same 40 hours culture supernatants by ELISA as described previously using the antibodies 11B11 and biotinylated anti-IL-4 (BVD6, Pharmigen), TRFK5 and biotinylated TRFK4 and R46A-2 and biotin-XMG1.2 (Pharmingen), respectively. Standard curves were constructed with purified IL-2, IL-4, IL-5 and IFN-g (supernatants from the respective X63.Ag. cell lines). Tests were done in duplicate.

The presence of transgenic Ig in the serum of mice was detected using a capture enzyme-linked immunosorbent assay (ELISA) as described in Example I.

Antibodies to transgenic Ig (γ1NANP) were detected by ELISA as in Example III. The isotype of antibodies was determined by ELISA in Example III.

As a source of antigen presenting cells (APC), spleen cells from unprimed mice were used and cultured with LPS/Dextran (25 μg/ml) for 24 hours and treated for 30 min at 37° C. with 25 μg/ml mitomycin C (Sigma). Before use, spleen cells from naive, primed, or primed and boosted mice were mixed with $2 \times 10^6$/ml APC in 96-well flat-bottom plates in the presence of 50 μg/ml synthetic peptide (-NVDP-). Each dilution of cells was plated in replicates of 48. Supernatants were harvested after 36 hours and 20 μl from each culture was tested for IL-2 activity using the NK.3 cell line. Single cultures supernatants were considered positive when the value of $^3H$-thymidine incorporation was greater than the mean of the replicate control cultures with no antigen plus two standard deviations. Frequencies of cytokine producing cells were calculated using the program described by Waldman and were calculated using maximum likelihood analysis.

The effects of STI on activation of T lymphocytes was determined. T cell responses were assessed using DNA coding for 12 amino acid determinants of the circumsporozoite (CS) protein of *Plasmodium falciparum* malaria parasite. The plasmid γ1NV²NA³ DNA contains an Ig H chain gene in which the V domain is engineered to code for a Th cell determinant (NANPNVDPNANP) in CDR2 and a B cell epitope (NANPNANPNANP) in CDR3 (antigenized antibody). The Th cell determinant (-NVDP-) and the B cell epitope only differ by two amino acid residues, A to V and N to D in position 5 and 6, respectively. As disclosed in Example IV, an antigenized antibody product of the same gene, when injected in complete Freunds' adjuvant, induces specific T cell proliferation and IL-2 secretion.

Figure 27:
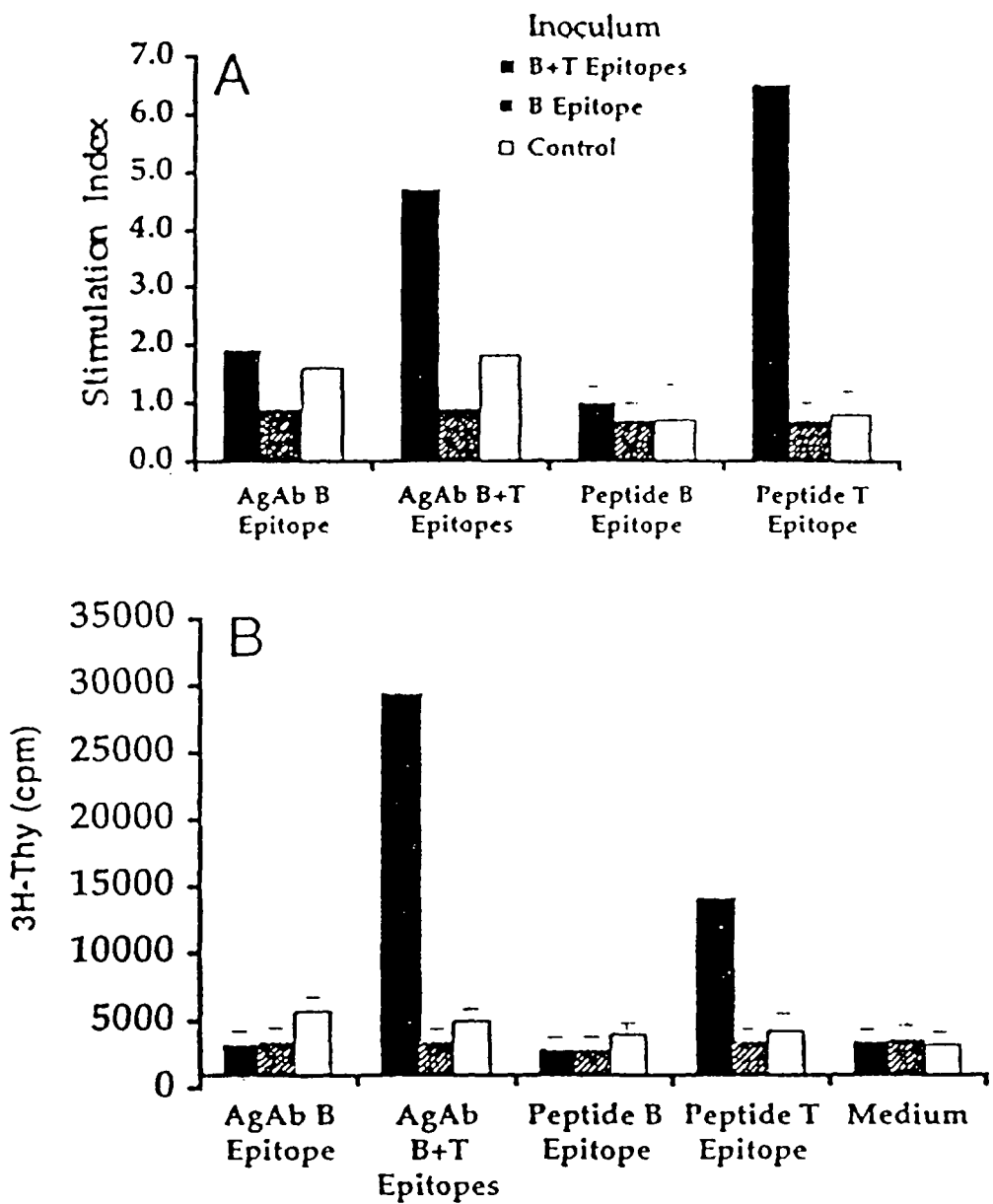
FIG. 27 shows antigen-specific activation of T lymphocytes by STI. Panel A shows the proliferative response of spleen cells from C57Bl/6 mice inoculated with plasmid DNA g1NANP coding for the B cell epitope (4 mice), γ1NV$^2$NA$^3$ coding for the B and T cell epitopes (4 mice), or control plasmid pSV2neo (2 mice), and harvested on day 7. Cells were cultured in the presence of the antigens indicated along the abscissa. Results refer to stimulation index expressed as the mean±S.D. Results correspond to two independent experiments. AgAb=antigenized antibody. Tests were run in triplicate. Panel B shows IL-2 production in spleen cell cultures from the same C57Bl/6 mice shown in panel A. Results are expressed as counts per minute (cpm) of the proliferative response of indicator NK.3 cells and are expressed as the mean±S.D.

Spleen cells harvested 7 days after a single intraspleen inoculation of 100 μg of γ1NV²NA³ DNA proliferated in culture after re-stimulation with the antigenized antibody expressing the Th cell determinant or the corresponding 12 mer Th cell determinant peptide (FIG. 27A). Proliferation occurred when cells were cultured with the T- but not the B-cell peptide demonstrating specific activation by the heterologous peptide in CDR2. Proliferation after culture with the antigenized antibody expressing -NVDP- also suggests that the CDR2 peptide within the antibody molecule is processed and presented by APC. When compared with the proliferative response of cells from mice immunized with the antigenized antibody in CFA, STI induced a response of similar or greater magnitude. Specific activation of T cells was accompanied by marked production of IL-2 (FIG. 27B). The lower amounts of IL-2 measured in cultures re-stimulated in vitro with the -NVDP- peptide most likely reflect a higher consumption as cells in these cultures were proliferating to a greater extent.

Figure 28:
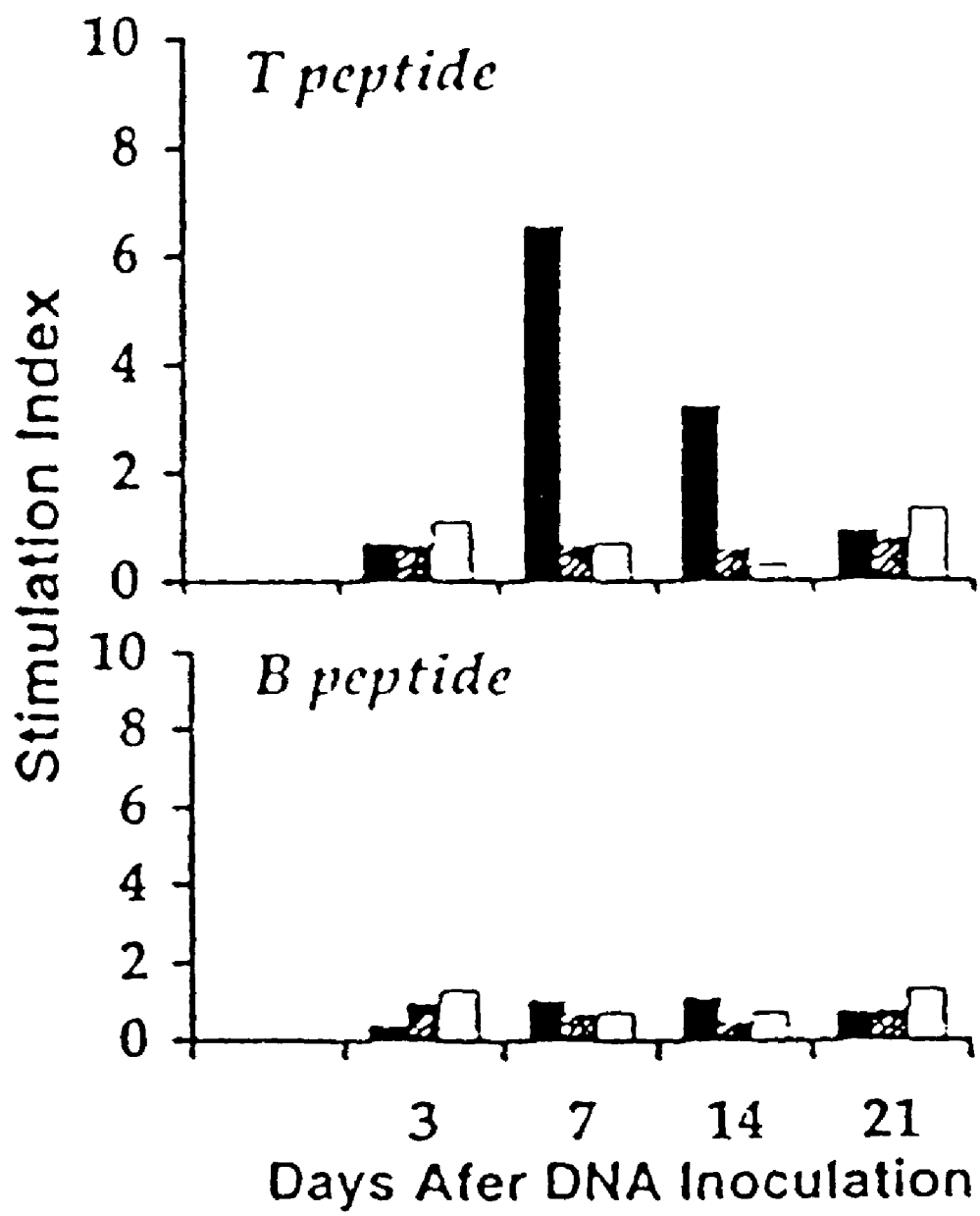
FIG. 28 shows kinetics of T cell activation in vivo. The proliferative response of spleen cells from C57Bl/6 mice inoculated with plasmid DNA was determined. Spleen cells were harvested on day 3, 7, 14 and 21. Cells were cultured in the presence of the synthetic peptide corresponding to the Th cell determinant (upper panel) or the B cell epitope (lower panel), as a control. Results refer to stimulation index. At each time point, groups consisted of 2 mice for the DNA coding for heterologous epitopes and one inoculated with plasmid pSV2neo control.

The kinetics of T cell activation in vivo was monitored in another experiment in which spleen cells were harvested 3, 7, 14 and 21 days after DNA inoculation (FIG. 28). Proliferation was absent on day 3, peaked on day 7, and was minimal by day 21. The response was specific, measured only when cells were re-stimulated in vitro with the Th cell determinant peptide. The production of IL-2 paralleled the proliferative response.

Figure 29:
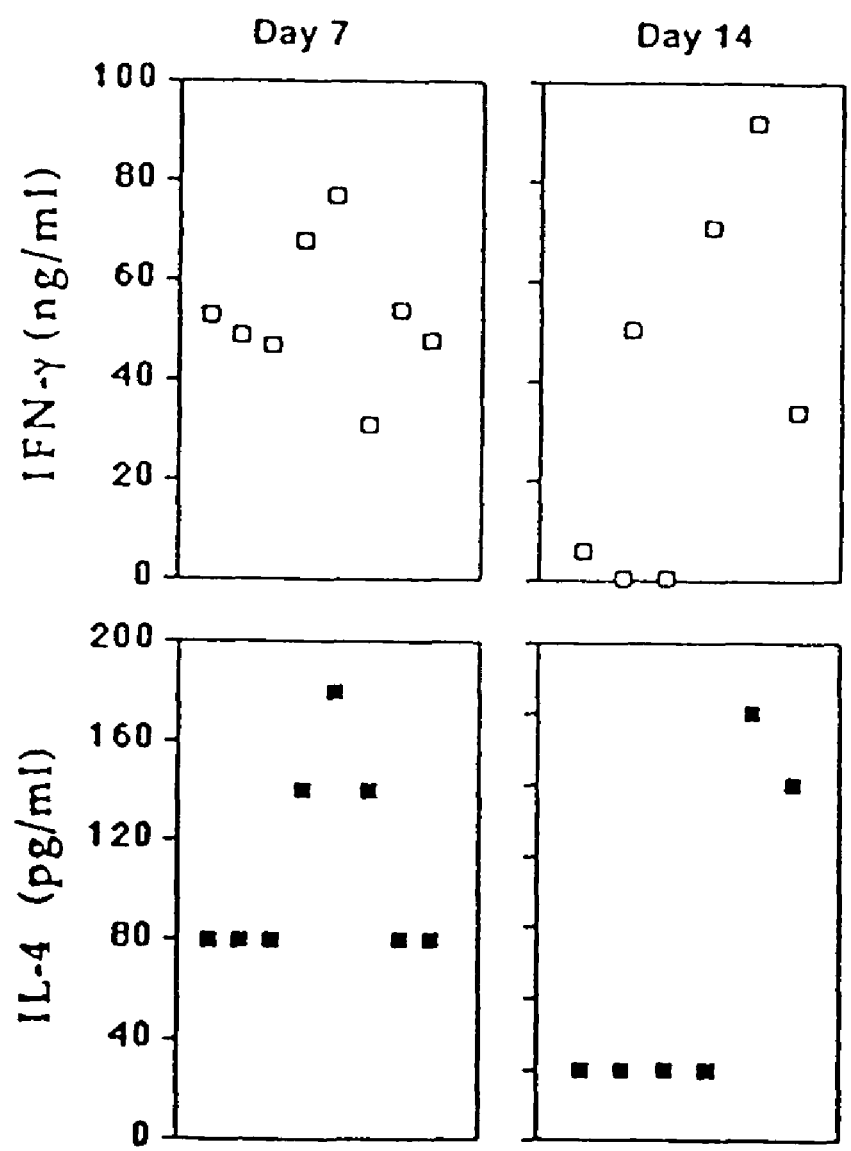
FIG. 29 shows levels of IFN-γ and IL-4 during the primary response. Spleen cells harvested 7 and 14 days after immunization were incubated with synthetic peptide corresponding to the Th cell determinant (50 γg/ml) for 40 hours. Supernatants from triplicate cultures were harvested and tested in capture ELISA specific for IFN-γ or IL-4.

Splenocytes harvested on day 7 and 14 were also assayed for production of IFN-γ, IL-4 and IL-5 to assess whether any polarization to Type 1 and Type 2 phenotype had occurred (FIG. 29). Both IFN-γ and IL-4 were detected, albeit in different amounts and IL-5 was absent. Since IFN-γ specific activity is on average 100 fold lower than IL-4, and IL-4 is typically secreted in much lower quantities than IFN-γ, these results indicate that both cytokines are produced proportionally and that cells activated through STI remain, by and large, uncommitted.

Figure 30:
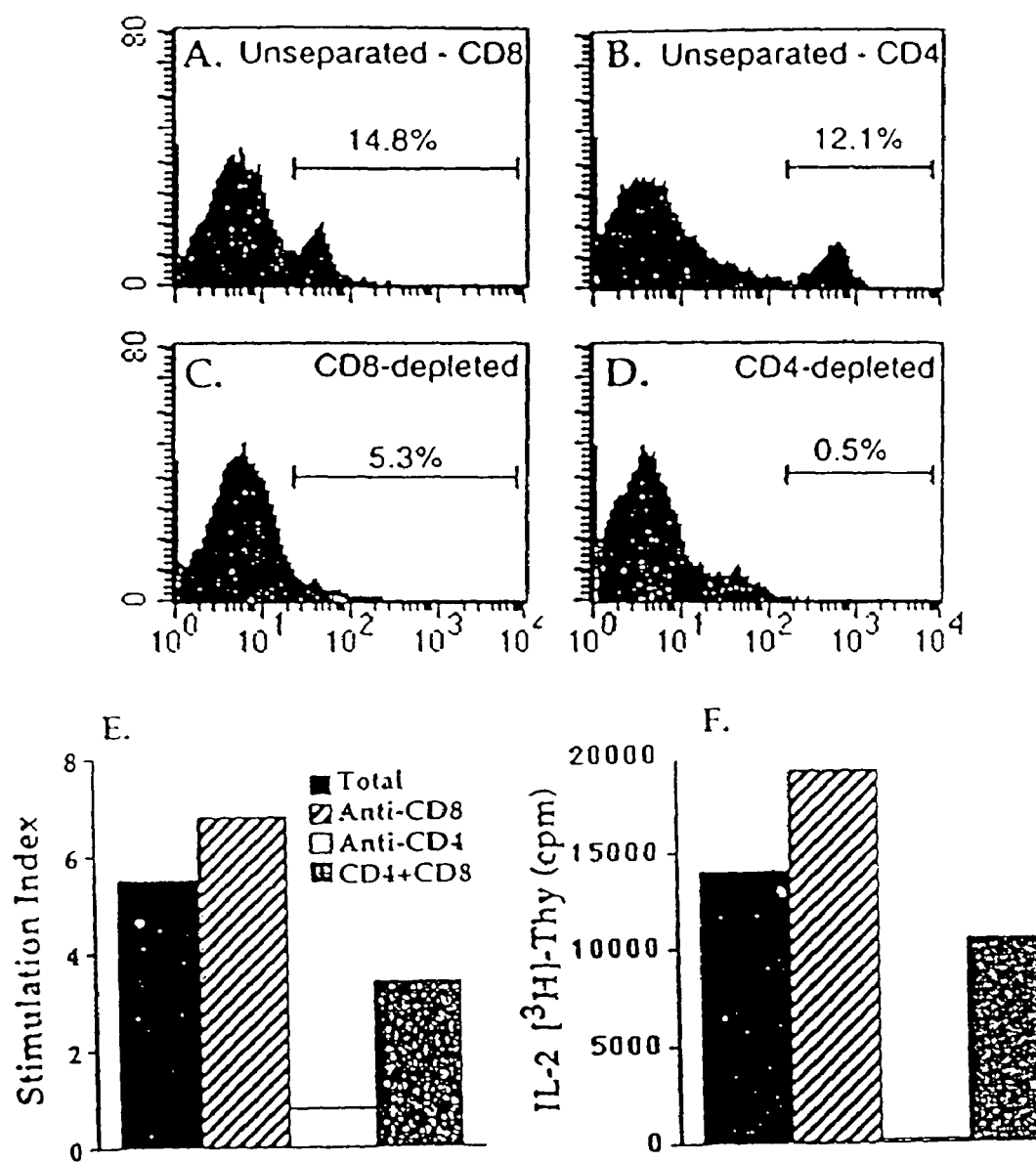
FIG. 30 shows activated cells are CD4+ T cells. Seven days after DNA inoculation, spleen cell populations were prepared and depleted of CD8+ (Panel C) or CD4+ (Panel D) cells by antibody plus complement. Unseparated CD8+ cells (Panel A) and unseparated CD4+ cells (Panel B) are shown as reference. The proliferative response (Panel E) and IL-2 production (Panel F) of unfractionated (total), separated CD4 and CD8, and reconstituted (CD4+CD8) T cell populations are shown. Stimulation indexes and IL-2 production were determined.

Activated cells were determined to be CD4$^+$ T lymphocytes. CD4$^+$ T cells were formally identified as the cell population proliferating and making cytokines. Spleen cells from mice immunized 7 days earlier were depleted of CD4$^+$ and CD8$^+$ cells by treatment in vitro with monoclonal antibodies specific for CD8 or CD4 plus complement. By flow-cytometry the purity of the two populations was 94% (CD4) and 99% (CD8), respectively (FIGS. 30C and 30D). The two cell populations were then cultured in vitro with the addition of fresh APC from naive mice and synthetic peptide -NVDP-. Proliferation occurred in the CD4$^+$ but not in the CD8$^+$ T cell population (FIG. 30E). Similarly, IL-2 production was detected only in the CD4$^+$ T cell population (FIG. 30F). These results demonstrate that STI selectively activates CD4$^+$ T lymphocytes.

Figure 31:
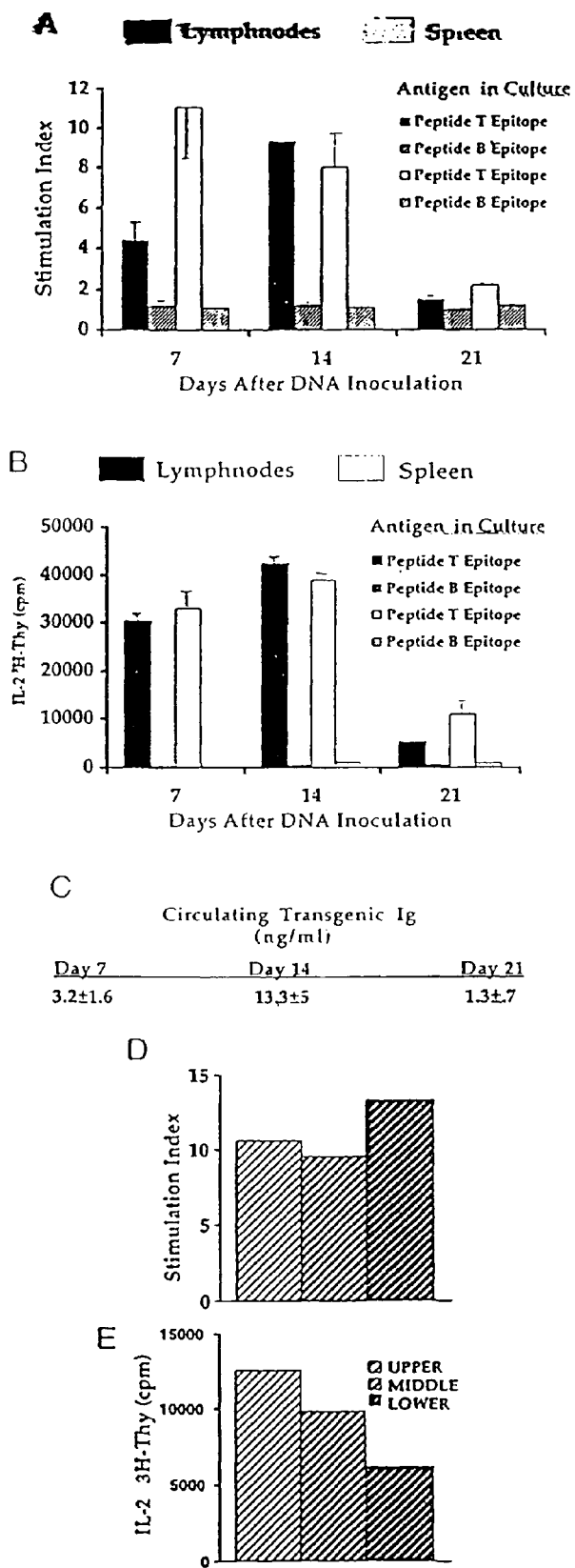
FIG. 31 shows T cell immunity induced by intraspleen DNA inoculation spreads to lymph nodes. Cell proliferation (Panel A) and IL-2 production (Panel B) in a pool of inguinal, mesenteric and cervical lymph node, and spleen cells harvested 7, 14 or 21 days after $\gamma1NV^2NA^3$ DNA inoculation. Lymph nodes were isolated from four mice/experiment. Serum transgenic Ig (ng/ml) in the serum is expressed as the mean±SD of six different mice at each time point (Panel C). Cell proliferation (Panel D) and IL-2 production (Panel E) of lymph nodes collected from (1) axillary, brachial, deep and superficial cervical (upper); (2) mesenteric, renal and epigastric (middle): and (3) popliteal, caudal, sciatic and lumbar (lower), lymph nodes 14 days after DNA inoculation. Lymph control. B) The occurrence of transcription is also documeneted (panel B). The total RNA of $10^5$ transfected cells was extracted in a single-step after 7 day culture using guanidinium thiocyanate phenol-chloroform. RNA coding for the H chain transgene product was detected by RT-PCR in transfected Raji cells.

T cell immunity was found to spread to other secondary lymphoid organs. Germane to the present studies was to determine the extent to which priming induces generalized T cell activation. In a first set of experiments, spreading of immunity to other secondary lymphoid organs was monitored by measuring cell proliferation and IL-2 production in a pool of inguinal, mesenteric and cervical lymph node cells. Seven days after DNA inoculation cells of the lymph node pool proliferated specifically upon re-stimulation in vitro with the -NVDP- but not with the B-cell epitope peptide (FIG. 31A). When compared with spleen cells, proliferation in lymph nodes was of a lesser magnitude. On day 14, the magnitude of the response in lymph node cells increased markedly reaching values comparable to spleen cells. On day 21, only residual proliferative activity existed in both lymph node and spleen cells. The magnitude and specificity of the proliferative responses were reflected by the levels of IL-2 in the corresponding culture supernatants (FIG. 31B). These kinetic analyses revealed that T cell activation in lymph nodes parallels that in the organ in which the process of immunity was initiated.

Analysis of the tempo of these responses in relation to other parameters of STI revealed something interesting. When the ratio between the stimulation indexes in lymph nodes and spleen was calculated, it became evident that, by day 14, T cell responsiveness in lymph nodes was prevalent. Moreover, the peak of the proliferative response in lymph nodes appeared to correlate with the peak values of transgenic Ig in the serum (FIG. 31C). The results indicate that a pattern of proportionality exists between secretion of transgenic Ig and spreading of T cell immunity.

Whether pooled lymph node cells were a true representation of a generalized response was further analyzed in lymph nodes collected according to precise anatomical distribution, lower (popliteal, caudal, sciatic and lumbar), middle (mesenteric, renal and epigastric) and upper (axillary, brachial, deep and superficial cervical) lymph nodes. T cell proliferation and IL-2 production were measured 14 days after DNA inoculation (FIGS. 31D and 31E). As shown both parameters were comparably elevated in all three lymphoid districts.

Figure 32:
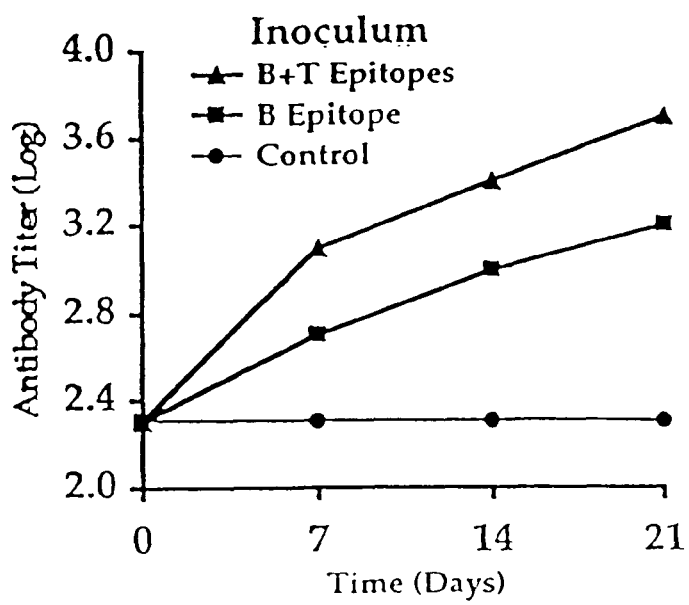
Figure 32:
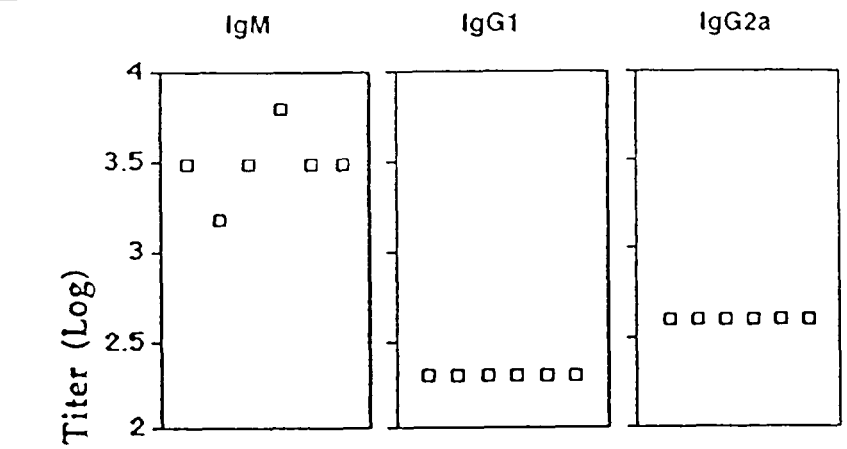
Figure 32:
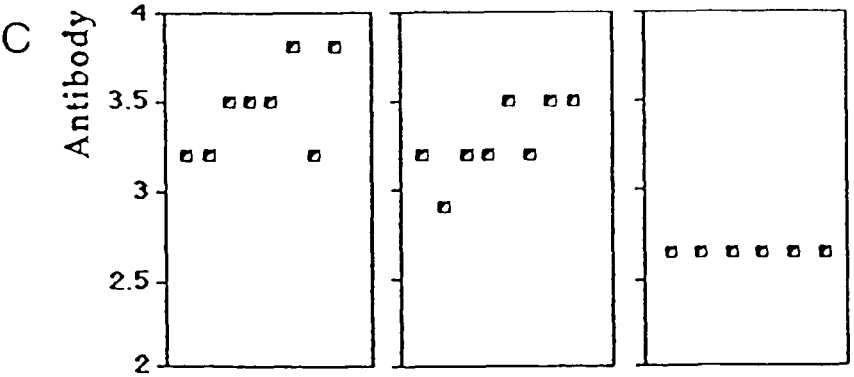

The effects of linked recognition of Th and B cell epitopes on the antibody response was determined. Expression of B and Th cell epitopes in linked association in transgenic Ig is expected to produce quantitative and qualitative effects on the B-cell response. First, antibody titers during priming were determined. Mice given the transgene coding for both the Th cell determinant and the B-cell epitope produced consistently higher antibody titers than mice immunized with the B-cell epitope-containing gene (FIG. 15), a result in agreement with the results described in Example IV. Second, specific activation of Th cells by the -NVDP- determinant was determined to be sufficient to promote the IgM to IgG1 switch. As disclosed in Example I and VI, STI mice produce mainly IgM, low level IgG2a, but no IgG1 unless the transgene is appropriately manipulated to increase the activation of dendritic cells (see Example VI). Mice given the Th/B double-epitope transgene developed IgM and IgG1 antibodies (FIG. 32). Presence of the Th cell determinant in the transgene did not affect the IgG2a response, which was minimal in both groups. These results indicate that the concomitant local activation of CD4$^+$ T cells and B lymphocytes drove secretion of downstream cytokines required for isotype switch in B cells. T cell immunity triggered by the Th cell determinant in linked association with a B-cell epitope optimizes the B-cell response by heightening the antibody titer and by promoting isotype switch. Since similar levels of IgM and IgG2a were observed irrespective of the presence of the Th cell determinant, the increased amount of specific antibodies is likely due to IgG1 antibodies.

The response to secondary exposure to antigen in vivo was determined. Frequencies were determined in mice given a booster immunization with antigenized antibody γ1NV$^2$NA$^3$ (50 μg) in incomplete Freunds' adjuvant (IFA) 90-110 days after DNA priming. In light of the fact that memory T cells are highest in number four days after booster immunization, LDA was performed in spleen cells harvested at this time.

The frequency of antigen-responsive T cells was much higher after booster immunization. The effect was not merely due to expansion of specific T cells by immunization with protein antigen in IFA because, in the absence of DNA priming, the frequency was about three times lower. For comparative purposes, LDA studies were also performed 4 and 7 days after single DNA inoculation (Table 9). On day 4 and 7 the frequency was 1/90,200 (group II) and 1/50,500 (group III), respectively. Four days after priming with protein antigen in IFA, the frequency was 1/60,000 (group VII). The average frequency during the memory response was 1/21,900 that is 2.5-4 times higher. Table 9 also shows that early after DNA priming antigen-responsive T cells were enriched 75 fold over naive precursors but dropped to 1/424,500 (group V) by day 110. Collectively, these results indicate that priming by STI establishes T cell memory. Re-encounter with antigen induced a faster and higher specific response.

TABLE 9

Frequency of CD4 T cells specific for the Th determinant.

| Group | Priming | Days After Priming | Booster | Day of Booster | Frequency of CD4 cells[a] |
|---|---|---|---|---|---|
| I | None | | | | 1/1,558,000[a] |
| II | DNA | 4 | | | 1/90,200 |
| III | DNA | 7 | | | 1/50,500[a] |
| IV | DNA | 14 | | | 1/36,400 |
| V | DNA | 110 | | | 1/424,500[b] |
| VI | DNA | | Protein | 110 | 1/21,900[b,c] |
| VII | None | | Protein | | 1/60,000[b] |

[a]Values represent the average of two independent experiments.
[b]Values represent the average of three independent experiments. The booster immunization was performed on day 90-110.
[c]Spleen cells were harvested and put in culture 4 days after booster immunization.

The level of cytokines produced by re-activated memory T are illustrated in Table 10. IFN-γ was detected in half (2/4) of the animals, IL-4 was produced in all four instances and IL-5 was detected in two cases only.

TABLE 10

Cytokines in the supernatant of memory cell cultures.

| Mouse | Priming | Day of Booster | Type of Booster | IFN-γ (ng/ml) | IL-4 (pg/ml) | IL-5 (ng/ml) |
|---|---|---|---|---|---|---|
| 1 | DNA | 150 | Protein | 7.7 | 230 | ND |
| 2 | DNA | 150 | Protein | ND | 240 | 3.2 |
| 3 | DNA | 150 | Protein | 59.9 | 440 | 7.3 |
| 4 | DNA | 150 | Protein | ND | 190 | ND |

ND, not detected.

Spreading of T cell responsiveness from the spleen to lymph nodes throughout the body is an original feature of the results disclosed herein. As a rule, immunization with antigen in adjuvant activates specific T cells only in the lymph nodes proximal to the site of injection. Recent studies using adoptive transfer of TCR-transgenic T cells clearly showed that subcutaneous immunization with antigen in adjuvant attracts specific T cells only in the draining but not in the non-draining lymph nodes. Thus, under conventional immunization procedures, migrating T cells are sequestered in the draining lymph nodes by antigen transported by dendritic cells or macrophages via the lymphatics. As disclosed herein, T cell responsiveness in distal lymph nodes began approximately at the same time (day 7) as in the spleen and peaked on day 14. Maximal T cell responsiveness occurred when transgenic Ig were most abundant in the serum. The results disclosed herein support a model in which transgenic Ig are released into the circulation, undergo localization in the cortex of distal lymph nodes, and serve as an anchor for T cells. Whether T cells activated in lymph nodes derive from re-circulating effector T cells or from naive $CD4^+$ T lymphocytes undergoing de novo activation, is not known. The first possibility is plausible since the observed kinetics are consistent with the notion that effector T cells leave the site where they encountered antigen within 48 hours and re-circulate through the body in 24 hours. The second possibility, de novo activation, is consistent with the fact that antigenized Ig clearly supported T cell activation in vitro.

The results disclosed herein indicate that STI is an effective way to activate CD4 T cells and establish durable T cell memory. The frequency of antigen-reactive T cells increased 3-4 fold in a long term primed animal and again several fold after booster immunization. In addition, the response was faster than the primary response, consistent with a functional definition of immunologic memory. In all likelihood, early effector T cells gave rise to resting memory cells, which are known to re-circulate as a pool through spleen and lymph nodes until they are sequestered again by antigen 24-48 hours later. The cytokines produced by re-activated memory T cells did not follow the pattern observed during priming. IFN-γ was detected in half (2/4) of the animals, IL-4 was produced in all four instances and IL-5 was detected in two cases only. These results indicate that the characteristics of priming are not maintained during the memory response and that priming does not pre-commit the outcome of a subsequent booster immunization.

These results demonstrate that administration of a nucleic acid molecule encoding an epitope results in T cell responsiveness with long term immunologic memory.

EXAMPLE IX

Activation of CD8 T Cells by Somatic Transgenesis Induces Protection Against Challenge with Influenza Virus This example describes the activation of CD8 T cells with administration of a nucleic acid molecule encoding an epitope from the influenza virus A/PR8.

The protocols used are in part described below (Billetta et al., *Eur. J. Immunol.* 25:776-783 (1995)).

Eight to ten week old C57BL/6 (H-2b) mice were purchased from the Jackson Laboratories (Bar Harbor, Me.). Mice were maintained in the animal facility of the University of California, San Diego, throughout the duration of the experiments.

Figure 33:
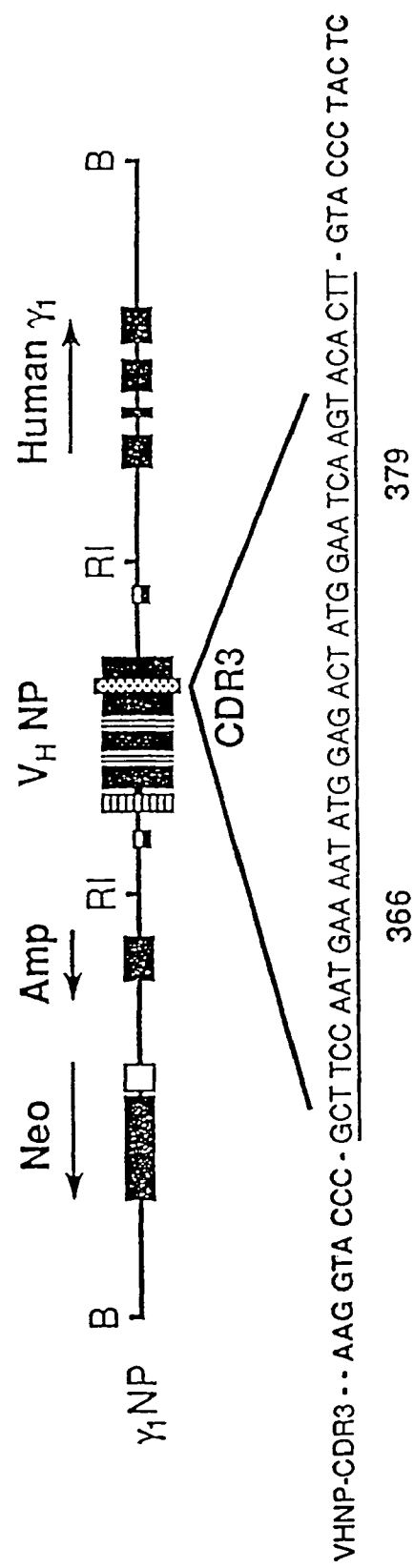

A H-chain gene was engineered to express in the third complementarity-determining region (CDR3) 13 amino acid residues from the sequence of the A/PR/8/34 influenza virus nucleoprotein (NP) antigen (FIG. 33). This NP peptide is presented in association with the Db allele in H-2b mide.

The NP synthetic peptide ASNeNMETM (amino acid residues 366-374) was purchased from Multiple peptide System (San Diego, Calif.) and synthesized on an ABI 430-A automated synthesizer (Applied Biosystems, Inc., Foster City, Calif.).

Mice were inoculated with 100 μg of plasmid DNA per inoculation. All DNA inoculations were done intraspleen as indicated under Example I. Groups of mice were additionally boosted after 12 sddks with 50 μg of NP peptide emulsified in incomplete Freunds' adjuvant. Control groups consisted in mice immunized twice with 50 μg of NP peptide emulsified in concomplete Freunds' adjuvant (positive control) or mice of the same age group that did not receive any treatment (negative control).

Mice were challenged intranasally with 10×LD50 dose of infectious homologous virus. After challenge mice were monitored for loss of weight and survival.

Cytogoxicity was tested on spleen cells using a 4 hour 51Cr release assay. Briefly, RMAS (H2b) target cells were labeled with Na51CrO4 (150 mCi/1×106 cells) for 1 hour at 37° C. in an atmosphere of 5% CO2 with or without NP peptide (10 μg/ml), then washed and resuspended in culture medium supplemented with 10% FCS. One hundred μl of 51Cr-labeled target cells (2.5×105 cells/ml) were mixed with effector cells in 100 μl at various (100:1) effector:target (E:T) ratio. The plates were incubated for 4 hours at 37° C. in 5% CO2, then centrifuged at 500 g for 4 minutes. One hundred μl of supernatant were removed and counted in a gamma counter. Spontaneous and maximal 51Cr releases were determined by incubating target cells in medium alone or in the presence of 1% Triton 100x, respectively. Percent cytotoxicity was calculated from triplicate wells as follows:

[experimental release−spontaneous release/maximal release−spontaneous release]×100.

Early studies in vitro demonstrated that a B cell harboring an If H chain transgene process and present in a T cell peptide to cytotoxic (CD8) T cells, and are lysed with high efficiency (Billetta et al., Eur. J. Immunol. 25:776-783 (1995)). For instance, when B-lymphoma cells (Db) were transfected with the H chain gene engineered to express in the third DCR the NP peptide ASNENNETMESSTL they were efficiently killed by specific CTL in a dose-dependent manner indicating that processing the presentation of the NP peptide at the surface of the cell had occurred. Killing was MHC-restricted and blocked by an anti-class-I MHC monoclonal antibody.

In a series of experiments, it was shown that C57BL6 mice inoculated with this transgene develop a CTL response. Spleen cells from inoculated mice were harvested three weeks after immunization and tested for their ability to kill NP peptide-pulsed RMAS target cells in a conventional cytotoxicity assay. RMAS cells without peptide served as a control. In this assay we found that between 60-75% of mice had generated a cytotoxic T cell response specific for the influenza NP peptide.

Figure 34:
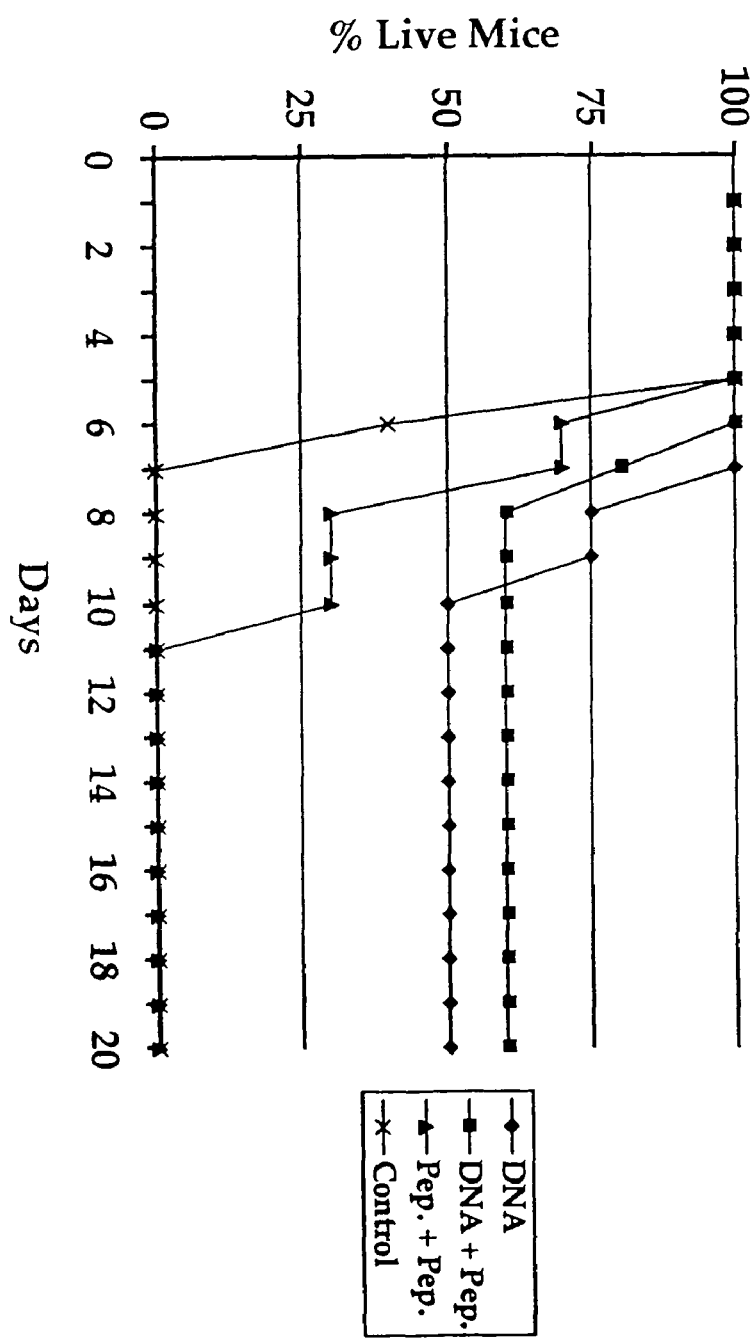

Protection and induction of memory CTL was also documented (see FIG. 34). In the experiment shown, mice (10 per group) were vaccinated wither via STI or with synthetic peptide in incomplete Freunds' adjuvant. A group of mice remained untreated and served as control. Three months after vaccination mice received an intranasal challenge with 10×LK50 dose of infectious influenza virus (i.e. 10 times the lethal dose of r50% of mice). As shown, all untreated mice vaccinated with synthetic peptide in adjuvant died by day 11. As shown, the majority (50 and 60%) of mice vaccinated by somatic transgene immunization survived.

EXAMPLE X

Positive Reciprocal Regulation Between Two Th Cell Epitope During Somatic Transgene Immunization This example describes the activation in vivo of CD4 T cells against determinants of a tumor antigen per se unable to induce a cellular response. This is obtained by immunization with nucleic acid molecule encoding tumor epitopes in linked association with a dominant T cell epitope of the malaria parasite.

Eight to ten week old D57BL/6 (H-2b) mice were purchased from the Jackson Laboratories (Bar Harbor, Me.). Mice were maintained in the animal facility of the University of California, San Diego, throughout the duration of the experiments.

Two H-chain genes were engineered to express in the CDR3 two amino acid sequences (VTSAPDTRPAP and DTRP3) from the tandem repeat of the tumor antigen MUC-1 (Gendler et al., Proc Natl Adad Sci USA, 84:6060-6064 (1987)). Each gene coding for a single epitope of the MUC-1 antigen was also engineered to code in the CDR2 for the Th cell determinant NANPNVDPNANP from the outer coat of the malaria parasite *P. Falciparum* (Nardin et al., Science 246:1603-1606 (1989)). The corresponding plasmid vector is termed γ1NV2VTSA3 (FIG. 35) and γ1NV2DTRP3.

Pilot experiments had shown that plasmid DNA coding for just the MUC-1-derived peptide sequence were unable to induce a proliferative response in vivo. However, when plasmids γ1NV2VTSA3 and γ1NV2DTRP3 were used, a strong response against the respective MUC-1 epitope was measured (see FIG. 35). None of the eight mice immunized with DNA coding for the single MUC-1 epitope alone developed a T cell response. In converse a response occurred in all (10+10) mice immunized with a gene coding in linked association for the MUC-1 epitope and the heterologous Th cell determinant from the malaria parasite (FIG. 1).

These results indicate that weak immunogenic epitopes (such as the ones from MUC-1) can be rendered immunogenic by association with a strong heterologous Th-cell determinant. This finding is relevant for the development of a MUC-1-based vaccine but also for the development of T cell immunity against other tumor antigens. T cells against determinants on tumor antigens are thought to be eliminated in great part during negative selection in the thymus. This leaves the adult organism with only T cells reactive against a minority of determinants, usually weak (cryptic or subdominant) determinants, the residual T cell repertoire. Since the objective of any effort to develop effective strategies of immune therapy against cancer is to expand those residual tumor-specific precursor T cells, it appears that a linked Th/Th association in a gene used for somatic transgene immunization can render immunogenic an otherwise poorly or non-immunogenic Th cell determinant. The significance of this finding reaches beyond tumor antigens, and is applicable to vaccines against self antigens and antigens of exogenous pathogens.

EXAMPLE XI

Somatic Transgenesis Functions In Vitro for Human B Cells

This example describes the spontaneous transfection of human B cells using bacterial plasmid DNA coding for an immunoglobulin gene.

Raji (MHC class II$^+$) and RJ2.2.5 (a MHC class II$^-$ variant) were cultured in RPMI-1640 containing 10% FCS supplemented with 2% glutamine.

Plasmid DNA g1NANP was described in FIG. 1 and Example I. PCR and RT-PCR methodologies are as described in Example II.

Figure 37:
Figure 37:
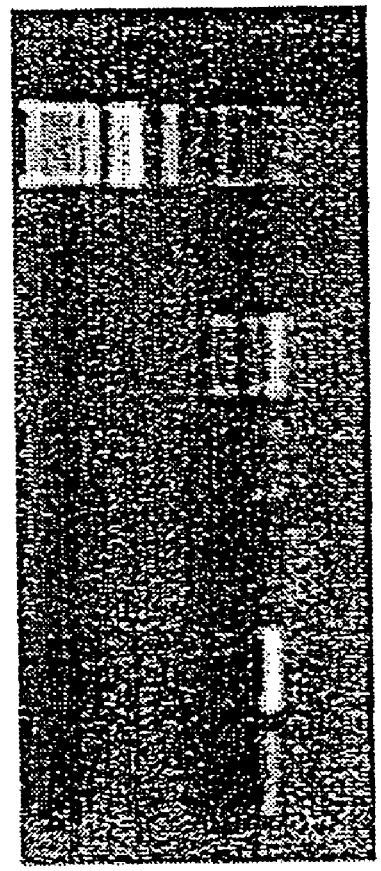

Raji (MHC Class II$^+$) and RJ2.2.5 (a MHC class II$^-$ variant) were harvested and washed thoroughly with sterile saline, counted and redistributed at various concentrations in 300 µl of phosphate buffered saline. 5 µg of plasmid DNA was added to the cell suspension and incubated at 37° C., for 1 hour in a 5% CO2 atmosphere. After the incubation the cells were washed with saline and put in culture medium and grown at 37° C., 5% CO2. Uptake and transfection were assessed on cells harvested 24 hours later. Genomic DNA was extracted using the QIAamp Blood Kit (Qiagen) and subject to two-round of nested PCR using VDJ specific primers (see Example II). The PCR products were analyzed on a 1% agarose gel with ethidium bromide stain. After 24 hours the transgene was detected with PCR in both the Raji and RJ2.2.5 cells (see FIG. 37) suggesting that uptake and integration of the transgene had occurred. Next, we determined that transcription had also occurred. The total RNA of 10$^5$ transfected cells was extracted in a single-step after 7 days of culture using granidinium thicyanate phenol-chloroform. By RT-PCR RNA coding for the H chain transgene product was detected in transfected Raji but not in untransfected Raji cells (see FIG. 37). A corresponding murine transfectoma cell line was used as a positive control.

These data constitute evidence that human B cells the transgene is are capable of taking up bacterial plasmid spontaneously, and translocate the mammalian gene contained in the plasmid to the nucleus for integration and transcription. This in vitro experiment recapitulates, therefore, the essence of somatic transgenesis as documented in vivo in the mouse.

Throughout this application various publications have been referenced. The disclosures of these publications in their entireties are hereby incorporated by reference in this application in order to more fully describe the state of the art to which this invention pertains.

Although the invention has been described with reference to the examples provided above, it should be understood that various modifications can be made without departing from the spirit of the invention. Accordingly, the invention is limited only by the claims.

I claim:

1. A normal B lymphocyte cell comprising a plasmid comprising nucleic acid encoding B cell specific promoter and enhancer elements operationally linked to a nucleic acid encoding a heavy chain immunoglobulin molecule comprising an exogenous epitope comprising a discrete sequence of a heterologous antigen, wherein said exogenous epitope is inserted within a complementarity-determining region (CDR) of said immunoglobulin molecule, wherein said exogenous epitope is a T cell epitope.

2. The B lymphocyte cell of claim 1 wherein said cell induces T-cell immunity.

3. The B lymphocyte cell of claim 1 wherein said immunoglobulin molecule comprises exogenous B-cell and T-cell epitopes.

4. The B lymphocyte cell of claim 3 wherein said cell induces B-cell and T-cell immunity.

5. The B lymphocyte of claim 1 wherein said CDR is CDR3.

6. The B lymphocyte of claim 1 wherein said B lymphocyte is non-proliferative.

* * * * *